US008034588B2

(12) United States Patent
Bergeron et al.

(10) Patent No.: US 8,034,588 B2
(45) Date of Patent: Oct. 11, 2011

(54) SPECIES-SPECIFIC, GENUS-SPECIFIC AND UNIVERSAL DNA PROBES AND AMPLIFICATION PRIMERS TO RAPIDLY DETECT AND IDENTIFY COMMON BACTERIAL AND FUNGAL PATHOGENS AND ASSOCIATED ANTIBIOTIC RESISTANCE GENES FROM CLINICAL SPECIMENS FOR DIAGNOSIS IN MICROBIOLOGY LABORATORIES

(75) Inventors: Michel G. Bergeron, Sillery (CA); François J. Picard, Cap-Rouge (CA); Marc Ouellette, Sillery (CA); Paul H. Roy, Loretteville (CA)

(73) Assignee: Geneohm Sciences Canada Inc., Quebec (CA)

( * ) Notice: Subject to any disclaimer, the term of this patent is extended or adjusted under 35 U.S.C. 154(b) by 1307 days.

(21) Appl. No.: 10/753,169

(22) Filed: Jan. 7, 2004

(65) Prior Publication Data

US 2004/0185478 A1 Sep. 23, 2004

Related U.S. Application Data

(63) Continuation of application No. 10/753,169, filed on Jan. 7, 2004, which is a continuation of application No. 09/989,643, filed on Nov. 20, 2001, now abandoned, which is a continuation of application No. 09/297,539, filed as application No. PCT/CA97/00829 on Nov. 4, 1997, now abandoned.

(51) Int. Cl.
C12P 19/34 (2006.01)
C12Q 1/68 (2006.01)
C07H 21/02 (2006.01)
C07H 21/04 (2006.01)
C07H 21/00 (2006.01)

(52) U.S. Cl. ......... 435/91.2; 435/6; 435/91.1; 536/23.1; 536/24.3; 536/24.33; 536/25.3

(58) Field of Classification Search ............. 435/6, 91.1, 435/183, 91.2; 436/94, 501; 536/23.1, 24.3, 536/24.32, 25.3, 24.33
See application file for complete search history.

(56) References Cited

U.S. PATENT DOCUMENTS

| 4,816,389 | A | 3/1989 | Sansonetti et al. |
| 5,030,556 | A | 7/1991 | Beaulieu et al. |
| 5,041,372 | A | 8/1991 | Lampel et al. |
| 5,084,565 | A | 1/1992 | Parodos et al. |
| 5,089,386 | A | 2/1992 | Stackebrandt et al. |
| 5,162,199 | A | 11/1992 | Stern et al. |
| 5,232,831 | A | 8/1993 | Milliman et al. |
| 5,292,874 | A | 3/1994 | Milliman |
| 5,298,392 | A | 3/1994 | Atlas et al. |
| 5,334,501 | A | 8/1994 | Adams et al. |
| 5,389,513 | A | 2/1995 | Baquero et al. |
| 5,401,631 | A | 3/1995 | Lane et al. |
| 5,437,978 | A | 8/1995 | Ubukata et al. |
| 5,472,843 | A | 12/1995 | Milliman |
| 5,476,929 | A | 12/1995 | Briles et al. |
| 5,523,205 | A | 6/1996 | Cossart et al. |
| 5,523,217 | A | 6/1996 | Lupski et al. |
| 5,541,308 | A | 7/1996 | Hogan et al. |
| 5,574,145 | A | 11/1996 | Barry et al. |
| 5,595,874 | A | 1/1997 | Hogan et al. |
| 5,599,665 | A | 2/1997 | Barbieri et al. |
| 5,627,275 | A | 5/1997 | Roll |
| 5,652,102 | A | 7/1997 | Fratamico et al. |
| 5,708,160 | A | 1/1998 | Goh et al. |
| 5,866,336 | A | 2/1999 | Nazarenko et al. |
| 5,994,066 | A | 11/1999 | Bergeron et al. |
| 6,001,564 | A | 12/1999 | Bergeron et al. |
| 6,037,130 | A | 3/2000 | Tyagi et al. |
| 6,582,908 | B2 | 6/2003 | Fodor et al. |
| 6,610,836 | B1 | 8/2003 | Breton et al. |
| 2004/0185478 | A1 | 9/2004 | Bergeron et al. |
| 2005/0042606 | A9 | 2/2005 | Bergeron et al. |
| 2006/0263810 | A1 | 11/2006 | Bergeron et al. |
| 2007/0009947 | A1 | 1/2007 | Bergeron et al. |
| 2007/0105129 | A1 | 5/2007 | Bergeron et al. |
| 2009/0047671 | A1 | 2/2009 | Bergeron et al. |
| 2009/0053702 | A1 | 2/2009 | Bergeron et al. |
| 2009/0053703 | A1 | 2/2009 | Bergeron et al. |
| 2009/0068641 | A1 | 3/2009 | Bergeron et al. |
| 2010/0267012 | A1 | 10/2010 | Bergeron et al. |

FOREIGN PATENT DOCUMENTS

| CA | 2052822 | 4/1992 |
| EP | 0 133 288 | 2/1985 |
| EP | 0 133 671 | 3/1985 |
| EP | 0 272 009 | 6/1988 |
| EP | 0 277 237 | 8/1988 |
| EP | 0 297 291 | 1/1989 |
| EP | 0 377 896 | 10/1989 |
| EP | 0 364 255 | 4/1990 |
| EP | 0 438 115 | 7/1991 |
| EP | 0 466 251 | 1/1992 |
| EP | 0 527 628 | 2/1993 |

(Continued)

OTHER PUBLICATIONS

Attachment for sequence comparison between 5'-CCAGCTGTA TTAGAAGTA-3' from SEQ ID NO:9 and complete genomes of bacteria *Bacillus Cereus* Q1 and AH187.* Attachment for sequence comparison between 5'-CCAGCTGTA TTTGAGT-3' from SEQ ID NO:10 and complete genome of *Streptococcus mutans* UA159.*
Aminov, et al. "Cloning, sequencing and complementation analysis of the recA gene from *Prevotella ruminicola.*" FEMS *Microbiology Letters.* 144:53-59 (1996).
Berg, et al. Development of an amplification and hybridization assay for the specific and sensitive detection of *Mycoplasma fennentans* DNA. *Molecular and Cellular Probes.* 10:7-14 (1996).
Luneberg, et al. Detection of *Mycoplasma pneumoniae* by Polymerase Chain Reaction and Nonradioactive Hybridization in Microtiter Plates. *Journal of Clinical Microbiology.* 31(5): 1088-1094 (1993).

(Continued)

*Primary Examiner* — Frank W Lu
(74) *Attorney, Agent, or Firm* — Knobbe Martens Olson & Bear LLP

(57) ABSTRACT

Provided herein are methods and kits for the specific and ubiquitous detection of *Streptococcus agalactiae.*

17 Claims, No Drawings

FOREIGN PATENT DOCUMENTS

| | | |
|---|---|---|
| EP | 0 577 523 | 1/1994 |
| EP | 0 630 973 A2 | 12/1994 |
| EP | 0 652 291 | 5/1995 |
| EP | 0 695 803 | 2/1996 |
| EP | 0 761 815 | 3/1997 |
| EP | 0 786 519 | 7/1997 |
| EP | 0 804 616 | 11/1997 |
| FR | 2584419 | 1/1987 |
| FR | 2599743 | 12/1987 |
| FR | 2636075 | 3/1990 |
| FR | 2685334 | 6/1993 |
| FR | 2686604 A1 | 7/1993 |
| FR | 2699539 | 6/1994 |
| JP | 6-54700 | 3/1994 |
| JP | 6-90798 | 4/1994 |
| JP | 6-165681 | 6/1994 |
| JP | 7-67657 | 3/1995 |
| JP | 7-209294 | 8/1995 |
| WO | WO 90/14444 | 11/1990 |
| WO | WO 91/08305 | 6/1991 |
| WO | WO 91/11531 | 8/1991 |
| WO | WO 91/16454 | 10/1991 |
| WO | WO 91/18926 | 12/1991 |
| WO | WO 92/03455 | 3/1992 |
| WO | WO 92/11273 | 7/1992 |
| WO | WO 92/14488 | 9/1992 |
| WO | WO 93/03186 | 2/1993 |
| WO | WO 93/12245 | 6/1993 |
| WO | WO 94/02645 | 2/1994 |
| WO | WO 94/17205 | 8/1994 |
| WO | WO 95/00650 | 1/1995 |
| WO | WO 95/09025 | 4/1995 |
| WO | WO 95/20055 | 7/1995 |
| WO | WO 96/00298 | 1/1996 |
| WO | WO 96/02648 | 2/1996 |
| WO | WO 96/08582 | 3/1996 |
| WO | WO 96/18745 | 6/1996 |
| WO | WO 98/20157 | 5/1998 |
| WO | WO 99/24059 | 5/1999 |
| WO | WO 00/14274 | 3/2000 |
| WO | WO 01/023604 | 4/2001 |
| WO | WO 2004/055205 | 7/2004 |

OTHER PUBLICATIONS

Murakami, et al. "Identification of methicillin-resistant strains of staphylococci by polymerase chain reaction." Journal of Clinical Microbiology. 29(10): 2240-2244 (1991).

An, G. and J.D. Friesen (1980). "The nucleotide sequence of tufB and four nearby tRNA structural genes of *Escherichia coli*". Gene 12:33-39.

Andersson, Siv. G.E. (1995). "Unusual Organization of the rRNA Genes in *Rickettsia prowazekii*". Journal of Bacteriology 177(14):4171-4175.

Birnboim, H.C. and J. Doly (1979). Nucleic Acids Research 7(4):1513-1523.

Bremaud, L., et al., (1995). "Genetic and molecular analysis of the tRNA-tufB operon of the myxobacterium Stigmatella aurantiaca". Nucleic Acids Research 23(10):1737-1743.

Brisson-Noel, A., et al. (1988). "Evidence for Natural Gene Transfer from Gram-Positive Cocci to *Escherichia coli*". Journal of Bacteriology 170(4):1739-1745.

Carlin, N.I.A., et al. (1992). "Monoclonal Antibodies Specific for Elongation Factor Tu and Complete Nucleotide Sequence of the tuf Gene in *Mycobacterium tuberculosis*". Infection and Immunity 60(8):3136-3142.'.

Chamberland, S., et al., (1992). "Antibiotic Susceptibility Profiles of 941 Gram-Negative Bacteria Isolated from Septicemia Patients Throughout Canada". Clinical Infectious Diseases 15:615-628.

Croize, J. (1995). "Les methodes automatisees d'identification des bacteries a l'aube de 1995". La Lettre de l'Infectiologue. 10(4):109-113.

Designer PCR, the advertisement from Research Genetics. Nucleic Acids Res. 22(15), Aug. 11, 1994.

Dieffenback, C.W. and G.S. Dveksler, Eds., (1995. "PCR Primer: A Laboratory Manual" Cold Spring Harbor Laboratory Press, pp. 133-155.

Dutka-Malen, S., et al. (1992). Sequence of the vanC gene of *Enterococcus gallinarum* Bm 4174 encoding a D-alanine:D-alanine ligase-related protein necessary for vancomycin resistance:. Gene 112:53-58.

East, A.K. And K.G.H. Dyke (1989). "Cloning and Sequence Determination of Six a*Staphylococcus aureus* beta-Lactamases and Their Expression in *Escherichia coli* and *Staphylococcus aureus*". Journal of General Microbiology 135:1001-1015.

Ehrlich, G.D. And S.J. Greenberg (1994). "PCR-Based Diagnosis in Infectious Disease," Blackwell Scientific Publications, pp. 3-18 and 665-687.

Emori, T.G. And R.P. Gaynes (1993). "An Overview of Nosocomial Infections, Including the Role of Microbiology Laboratory". Clinical Microbiology Reviews 6(4):428-442.

Evers, S., et al. (1994). "Sequence of the vanB and ddl genes encoding D-alanine:D-lactate and D-alanine:D-alanine ligases in vancomycin-resistant *Enterococcus faecalis* V583". Gene 140:97-102.

Eykyn, S.J., et al. (1990). "The causative organisms of septicaemia and their epidemiology". Journal of Antimicrobial Chemotherapy 25(Suppl. C):41-58.

Fani, R., et al. (1993). "Use of random amplified polymorphic DNA (RAPD) for generating specific DNA probes for microorganisms". Molecular Ecology 2:243-250.

Fleischmann, R.D., et al. (1995). "Whole-Genome Random Sequencing and Assembly of *Haemophilus influenzae* Rd". Science 269:496-498, 507-512.

Flores, N., et al. (1992). "Recovery of DNA from Agarose Gels Stained with Methylene Blue". Biotechniques 13(2):203-205.

Kamla, V. (1994). DATAASE EMPRO. EMBL, AC:Z34275.

Kellogg, D.E., et al. (1994). "TagStart Antibody: "Hot Start" PCR Facilitated by a Neutralizing Monoclonal Antibody Directed Against Taq DNA Polymerase". BioTechniques 16(6):1134-1137.

Koenig, C., et al. (1992). "Analyses of the FlashTrack DNA Probe and UTIscreen Bioluminescence Tests for Bacteriuria". Journal of Clinical Microbiology 30(2):342-345.

Kwok, S. and S. Higuchi (1989). "Avoiding false positive with PCR". Nature 339:237-238.

Lee, H.H., S.A. Morse and O. Olsvik, Eds. (1997). "Nucleic Acid Amplification Technologies: Application to Disease Diagnosis". Biotechniques Books, Div. Eaton Publishing, p. 7.

Loechel, S., et al. (1989). "Nucleotide sequence of the tuf gene from *Mycoplasma genitalium*". Nucleic Acids Research 17(23):10127.

Lewin, B. (1990). "Genes IV". Oxford University Press, pp. 497-517.

Ludwig, W., et al. (1994). Database Empro. EMBL, AC:X76863, X76866, X76867, X76871, X76872.

Monod, M., et al. (1986). "Sequence and Properties of pIM13, a Macrolide-Lincosamide-Streptogramin B Resistance Plasmid from *Bacillus subtilis*". Journal of Bacteriology 167(1):138-147.

Murphy, E., et al. (1986). Database Empro. EMBL, AC:X03216.

Neidhardt, F.C., et al., Eds. (1996). "*Escherichia coli* and *Salmonella* Cellular and Molecular Biology". 2nd Ed., vol. 1. ASM Press, pp. 1432-1457.

Ohama, T., et al., (1987). "Organization and Codon Usage of the Streptomycin Operon in *Micrococcus luteus*, a Bacterium with a High Genomic G+C Content". Journal of Bacteriology 169(10):4770-4777.

Olcen, et al. (1995). "Rapid diagnosis of bacterial meningitis by a seminested PCR strategy". Scand. J. Infect. Dis. 27:537-539.

Ouellette, M., et al. (1987). "Precise insertion of antibiotic resistance determinants into Tn-21-like transposons: Nucleotide sequence of the Oxa-1 beta-lactamase gene". Proc. Natl. Acad. Sci. USA 84:7378-7382.

Perlee, L., et al. (1993). Database Empro. EMBL, CA:L23125.

Persing, D.H., et al., Eds. (1993). "Diagnostic Molecular Microbiology: Principles and Applications". American Society for Microbiology, Washington, D.C., pp. xxi, 51-104.

Pezzlo, M.T., et al. (1992). "Detection of Bacteriuria and Pyuria by URISCREEN, a Rapid Enzymatic Screening Test". Journal of Clinical Microbiology 30:680-684.

Podbielski, *Streptococcus agalactiae* camp gene. Submitted to Genbank database on Mar. 22, 1993, accession No. X72754.

Podzorski, R.P. and D.H. Persing (1995). "Molecular Detection and Identification of Microorganisms" in "Manual of Clinical Microbiology", ASM press, pp. 130-157.

Porcella, S.F., et al. (1996). "Identification of an EF-Tu protein that is periplasm-associated and processed in *Neisseria gonorrhoeae*". Microbiology 142:2481-2489.

Sambrook, J., et al., Eds. (1989). "Molecular Cloning: A Laboratory Manual", 2nd Ed. Cold Spring Harbor Laboratory Press, pp. 1.21-1. 52, 9.31-9.62, 10.1-10.70, 11.1-11.61.

Sanger, F., et al. (1977). "DNA sequencing with chain-terminating inhibitors". Proc. Natl. Acad. Sci. USA 74(12):5463-5467.

Shaw, K.J., et al. (1989). "Isolation, Characterization, and DNA Sequence Analysis of an ACC(6')-II Gene from *Pseudomonas aeruginosa*". Antimicrobial Agents and Chemotherapy 33(12):2052-2062.

Stager, C.E. and J.R. Davis (1992). "Automated Systems for Identification of Microorganisms". Clinical Microbiology Reviews 5(3):302-327.

Stark, R.P. and D.G. Maki. (1984). "Bacteriuria in the catherized patient". The New England Journal of Medicine 311(9):560-564.

Watson, J.D., et al., (1976). "Molecular Biology of the Gene", 4th Ed. The Benjamin/Cummings Publishing Company, Inc., pp. 339-358.

York, M.K., et al. (1992). "Evaluation of the autoSCAN-W/A Rapid System for Identification and Susceptibility Testing of Gram-Negative Fermentation Bacilli". Journal of Clinical Microbiology 30(11):2903-2910.

Yoshikawa, et al., "*Bacillus subtilis* genes for RNA polymerase beta subunit, ribosomal proteins L12 and S7, elongation factors G and Tu and ribosomal proteins S10 and L3". Submitted to DDBJ/EMBL/Genbank database on Apr. 15, 1995.

Yoshikawa, H. (1996). Database Empro. EMBL. AC:D64127.

You-Xun, Z., et al. (1994). "Cloning, Sequencing, and Expression in *Escherichia coli* of the Gene Encoding a 45-Kilodalton Protein, Elongation Factor Tu, from Chlamydia trachomatis Serova F". Journal of Bacteriology 176(4):1184-1187.

Abdulkarim et al., Homologous Recombination between the *tuf* Genes of *Salmonella typhimurium*, J Mol Bio.(1996) 260: 506-522.

Abe et al., A Sensitive Method for the Detection of Enterotoxigenic *Escherichia coli* by the Polymerase Chain Reaction Using Multiple Primer Pairs, Zentralbl Bakteriol. (1992) 277(2): 170-8 (Abstract).

Akaboshi et al., Nucleotide sequence of the recA gene of Proteus mirabilis, Nucleic Acids Res. (1989) 17(11): 4390-4390.

Altschul et al., Basic Local Alignment Search Tool, J Mol Biol. (1990) 215: 403-410.

Amann et al., β-Subunit of ATP-Synthase: A Useful Marker for Studying the Phylogenetic Relationship of Eubacteria J Gen Microbiol. (1988) 134: 2815-2821.

Anborgh et al., New Antibiotic that Acts Specifically on the GTP-Bound Form of Elgonation Factor Tu, Embo J. (1991) 10(4): 779-784.

Ashimoto et al., Molecular epidemiology of *Staphylococcus spp.* contamination in the ward environment: study on mecA and femA genes in methicillin-resistant strains, Kasenshogaku Zasshi (1995) 69: 15-20.

Bäckman et al., Evaluation of an Extended Diagnostic PCR Assay for Detection and Verification of the Common Causes of Bacterial Meningitis in CSF and other Biological Samples, Mol Cell Probes (1999) 13: 49-60.

Balows et al., Eds. The Prokaryotes: A Handbook on the Biology of Bacteria: Ecophysiology, Isolation, Identification, Applications, 2nd Ed., Brenner, Introduction to the Family Enterobacteriaceae, Springer Verlag (1992) Chapter 141, pp. 2673-2695.

Balows et al., Eds. The Prokaryotes: A Handbook on the Biology of Bacteria: Ecophysiology, Isolation, Identification, Applications, 2nd Ed., Brenner, Additional Genera of Enterobacteriaceae, Springer Verlag (1992) Chapter 155, pp. 2922-2937.

Bej et al., Multiplex PCR amplification and immobilized capture probes for detection of bacterial pathogens and indicators in water, Mol. Cell. Probes (1990) 4: 353-365.

Belay et al., Methanogenic Bacteria from Human Dental Plaque, App Environ Microbiol.(1988) 54(2): 600-603.

Belay et al., Methanogenic Bacteria in Human Vaginal Samples, J Clin Microbiol.(1990) 28(7): 1666-1668.

Bell et al., Outer membrane protein H1 of *Pseudomonas aeruginosa*: purification of the protein and cloning and nucleotide sequence of the gene, J Bacteriol. (1989) 171(6): 3211-3217.

Bentley et al., Development of PCR-based Hybridization Protocol for Identification of *Streptococcal* Species, J Clin Microbiol. (1995) 33(5): 1296-1301.

Bercovier et al, Intra and Interspecies Relatedness of *Yersinia pestis* by DNA Hybridization and its Relationship to *Yersinia pseudotuberculosis*, Curr Microbiol. (1980) 4: 225-229.

Bergeron et al., Diagnosing Bacterial Infectious Diseases in One hour: An Essential Upcoming Revolution Infection (1995) 23(2): 69-72.

Bergeron et al., Preventing Antibiotic Resistance through Rapid Genotypic Identification of Bacteria and of Their Antibiotic Resistance Genes in the Clinical Microbiology Laboratory, J Clin Microbiol. (1998) 36(8): 2169-2172.

Berkenkamp et al, Infrared MALDI Mass Spectrometry of Large Nucleic Acids, Science (1998) 281: 260-262; American Association for the Advancement of science.

Black et al., Detection of streptococcal pyrogenic exotoxin genes by a nested polymerase chain reaction, Mol. Cell. Probes, 7 (1993) 255-259.

Brakstad et al., Detection of *Staphylococcusa aureus* by Polymerase Chain Reaction Amplification of the *nuc* Gene, J Clin Microbiol. (1992) 30(7): 1654-1660.

Brakstad et al., Comparison of Various Methods and Reagents for Species Identification of *Staphylococcus aureus* Positive or Negative for the mecA Gene, APMIS (1993) 101(9):651-654.

Brakstad et al., Multiplex Polymerase Chain Reaction for Detection of Genes for *Staphylococcus aureus* Thermonuclease and Methicillin Resistance and Correlation with Oxacilin Resistance, APMIS (1993) 101(9): 681-688.

Brakstad et al., Direct Identification of *Staphylococcus aureus* in blood cultures by detection of the gene encoding the thermostable nuclease or the gene product, APMIS (1995) 103: 209-218.

Brenner et al., Polynucleotide sequence relatedness among three groups of pathogenic *Escherichia coli* strains, Infect Immun. (1972) 6(3): 308-315.

Brenner et al., Polynucleotide sequence divergence among strains of *Escherichia coli* and closely related organisms, J Bacter. (1972) 109(3): 953-965.

Brenner et al., *Enterobacter gergoviae sp nov*.: a new species of Enterobacteriaceae found in clinical specimens and the environment, Int J Syst Bacter. (1980) 30(1): 1-6.

Brenner et al., *Escherichia vulneris*: a New Species of *Enterobacteriaceae* associated with human wounds, J Clin Microbiol. (1982) 15(6): 1133-1140.

Brenner et al., Attempts to classify herbicola group-*Enterobacter* agglomerans strains by deoxyribonucleic acid hybridization and phenotypic tests, Int J Sys Bacter. (1984) 34(1): 45-55.

Brenner et al., *Enterobacter asburiae* sp nov., a new species found in clinical spencimens, and reassignment of ervinia dissolvens and endnia nimipressuralis to the genus *Enterobacter* as *Enterobacter dissolvens* comb nov and *Enterobacter nimipressuralis* comb nov., J Clin Microbiol. (1986) 23(6): 1114-1120.

Brenner et al., Classification of citrobacteria by DNA hybridization: Designation of *Citrobacter farmed* sp nov., *Citrobacter youngae* sp nov., *Citrobacter braakii* sp nov., *Citrrobacter werkmanii* sp nove., *Citrobacter sedlakii* sp nove., and three unnambed citrobacter genomospecies, Int J. System Bacter. (1993) 43(4): 645-658.

Brenner et al., Encoded combinatorial chemistry, Proc Natl Acad Sci. USA (1992) 89: 5381-5383.

Brenner et al., Biochemical identification of *Citrobacter* species defined by DNA hybridization and description of *Citrobacter gillenii* sp nov., J Clin Microbio. (1999) 37(8): 2619-2624.

Buck, et al., Design Strategies and Performance of Custom DNA Sequencing Primers, Biotechniques (1999) 27(3): 528-536.

Caldas et al., Chaperone properties of bacterial elongation factor EF-Tu, J Biol Chem. (1998) 273(19): 11478-11482.

Chen et al., Transcription and expression of the exotoxin a gene of *Pseudomonas aeruginosa*, Gen Microbiol. (1987) 133 (11): 3081-3091.

Chen et al., Broad range DNA probes for detecting and amplifying eubacterial nucleic acids, FEMS Micro Lett. (1989) 57: 19-24.

Chiu et al., Mass spectrometry of nucleic acids, Clin Chem. (1999) 45: 1578-1579.

Aragón et al., Increase in β-lactam-resistant Proteus mirabilis Strains due to CTX-M- and CMY-type as well as New VEB-and Inhibitor-resistant Tem-type R-lactamases, J Antimicro Chemother. (2008) 61: 1029-1032.

Bagley et al., Significance of Fecal Coliform-positive *Klebsiella*, App Environ Microbio. (May 1977) 33(5): 1141-1148.

Duncan, Susceptibility of 1,500 Isolates of *Pseudomonas aeruginosa* to Gentamicin, Carbenicillin, Colistin, and Polymyxin B, Antimicro Agents Chemother. (Jan. 1974) 5(1): 9-15.

Feizabadi, Drug Resistant Patterns of Enterococci Recovered from Patients in Tehran During 2000-2003, *Letters to the Editor, Int J Antimicrob Agents* (2004) 24: 521-522.

Fenoll et al., Serotype Distribution and Antimicrobial Resistance of *Streptococcus pneumoniae* Isolates Causing Systemic Infections in Spain, 1979-1989, (1991) 13: 56-60.

Higashide et al., Methicillin-resistant *Staphylococcus saprophyticus* Isolates Carrying Staphylococcal Cassette Chromosome *mec* Have Emerged in Urogenital Tract Infections, Antimicrob Agents Chemother. (Jun. 2008) 52(6): 2061-2068.

Madico et al., Touchdown Enzyme Time Release-PCR for Detection and Identification of *Chlamydia trachomatic, C. pneumoniae*, and *C. psittaci* Using the 16S and 16S-23S Spacer rRNA Genes, J Clin Microbiol., (Mar. 2000) 38(3): 1085-1093.

Metherell et al., Rapid, sensitive, mircobial detection by gene amplification using restriction endonuclease target sequences, Mol Cell Probes (1997) 11: 297-308.

Paradis et al., The Potential of EF-Tu Sequences for Identification of Clinically Important Enterobacteriaceae Species (Sep. 1999) 39: 227; Abstract 1574, only.

Post et al., Development and Validation of a Multiplex PCR-based Assay for the Upper Respiratory Tract Bacterial Pathogens *Haemophilus influenzae, Streptococcus pneumoniae,* and *Moraxella catarrhalis,* (1996) 1(1): 29-39.

Zhanel et al., Antimicrobial Resistance in *Haemophilus influenzae* and Moraxella catarrhalis Respiratory Tract Isolates: Results of the Canadian Respiratory Organizm Susceptibility Study, 1997 to 2002, Antimicrob Agents Chemother., (Jun. 2003) 47(6): 1875-1881.

Ako-Nai et al., The Characterisation of Clinical Isolates of *Staphylococcus aureus* in Ile-Ife, Nigeria, J Med Microbiol. (1991) 34: 109-112.

Betzl et al., Identification of Lactococci and Enterococci by Colony Hybridization with 23S rRNA-Targeted Oligonucleotide Probes, Appl Environ Microbio., (Sep. 1990) 56(9):2927-2929.

Bongaerts et al., in Vitro Activities of BAY Y3118, Ciprofloxacin, Ofloxacin, and Fleroxacin against Gram-Positive and Gram-Negative Pathogens from Respiratory Tract and Soft Tissue Infections, Antimicro Agents Chemother. (Sep. 1993) 37(9):2017-2019.

Derecola et al., A 5-Year Surveillance Study of 44,691 Isolates of *Haemophilus Influenzae* Project Beta-Alert 1993-1997, Antimicro Agen Chemothera. (Jan. 1999) 43(1):185-186.

Ehrlich et al., Eds. PCR-Based Diagnosis in Infectious Disease, Chapters 1, 3, Blackwell Scientific Publications (1994), pp. 3-18 and 45-55.

GenBANK Accession No. M37185, Enterococcus Faecalis Gelatinase (gelE) Gene, Complete CDS (Apr. 1993).

GenBANK Accession No. Z26902, Phylogenetic Analysis Using 16S rDNA Sequencing of *Staphylococci* (Oct. 1993).

Guzmán et al., Role of Adherence in Pathogenesis of *Enterococcus faecalis* Urinary Tract Infection and Endocarditis, Infect Immun. (Jun. 1989) 57(6): 1834-1838.

Izumiya et al., Characterization of Multidrug-Resistant *Salmonella Enterica* Serovar Typhimurium Isolated in Japan, J Clin Microbio. (Jul. 2001) 39(7):2700-2703.

Jenkins, F. J., Basic Methods for the Detection of PCR Products, Genome Res. (Apr. 1994) 3:S77-S82.

Jordá, et al. Diagnosis of Nosocomial Pneumonia in Mechanically Ventilated Patients by the Blind Protected Telescoping Catheter, Intensive Care Med. (1993) 19:377-382.

Kim et al., Simultaneous Detection by PCR of *Escherichia Coli, Listeria Monocytogenes* and *Salmonella Typhimurium* in Artificially Inoculated Wheat Grain, Inter J Food Microbio. (Apr. 2006) 111:21-25.

Lewis et al., Emergence of Clinical Isolates of *Staphylococcus Aureus* Resistant to Gentamicin and Correlation of Resistance with Bacteriophage Type, J Infect Diseases, (Mar. 1978) 137(3): 314-317.

Miller et al., Community Acquired Lobar Pneumonia in Patients with HIV Infection and Aids, Thorax (Apr. 1994) 49:367-368.

Mitsuhashi M., Technical Report: Part 2. Basic Requirements for Designing Optimal PCR Primers, J Clin Lab Anal., (1996) 10: 285-293.

Neu, Harold C., the Crisis in Antibiotic Resistance, Science (Aug. 1992) 257:1064-1073.

Powers, Robert D., New Directions in the Diagnosis and Therapy of Urinary Tract Infections, (1991) Am J Obstet Gynecol., 164:1387-1389.

Bej et al., Detection of coliform bacteria and *Escherichia coli* by multiplex polymerase chain reaction: Comparison with defined substrate and plating methods for water quality monitoring, Appl Environ Microbio., (Aug. 1991) 57(8): 2429-2432.

Buck, et al., Design Strategies and Performance of Custom DNA Sequencing Primers, Biotechniques (1999) 27(3): 528-536.

Cebula, et al., Simultaneous identification of strains of *Escherichia coli* Serotype O157:H7 and their shiga-like toxin type by mismatch amplification mutation assay-multiplex PCR, J Clin Microbio. (Jan. 1995) 33(1): 248-250.

Frankel et al., Multi-gene amplification: simultaneous detection of three virulence genes in diarrhoeal stool, Mol Microbio. (1989) 3(12): 1729-1734.

GenBank Accession No. FJ858146, *Enterococcus* Faecium Strain QSE32 fsr Operon, Complete Sequence; and GelE (gelE) and SprE (sprE) Genes, Complete CDS, (Nov 2009) http://ncbi.nlm.nih.gov/nuccore/226938234.

GenBank Accession No. AP000565, Homo Sapiens Genomic DNA, Chromosome 210Q22, clone:f79A10, D21S226-Aml Region, Complete Sequence, (Nov. 1999) http://.ncbi.nlm.nih.gov/nuccore/6015482.

Haas et al., Universal PCR primers for detection of phytopathogenic *Agrobacterium* strains, App Environ Microbio., (Aug. 1995) 61(8): 2879-2884.

Harth et al., Epidemiology of *Vibrio parahaemolyticus* Outbreaks, Southern Chile, Emerg Infect Dis., (Feb. 2009) 15(2): 163-168 and GenBank Accession No. EU185084 downloaded from http://ncbi.nlm.nih.gov/nuccore/158524083.

Kaltenboeck et al., Two-step polymerase chain reactions and restriction endonuclease analyses detect and differentiate *ompA* DNA of *Chlamydia* spp., J Clin Microbio. (May 1992) 30(5): 1098-1104.

Lucotte et al., A multiple primer pairs polymerase chain reaction for the detection of human genital papillomavirus types, Mol Cell Probes (1993) 7: 339-344.

Opposition Brief by Infectio Diagnostic (I.D.I.) Inc. dated Sep. 14, 2007 from EP Application No. 95931109.3, filed Sep. 12, 1995.

Opposition Brief by Roche Diagnostics GmbH dated Sep. 21, 2007 from EP Application No. 95931109.3, filed Sep. 12, 1995.

Reply Brief by Roche Diagnostics GmbH dated Jan. 29, 2008 to Opposition Brief by I.D.I. from EP Application No. 95931109.3, filed Sep. 12, 1995 (w/English translation).

Reply Brief by I.D.I. dated Apr. 1, 2008 to Roche's Appeal Brief from EP Application No. 95931109.3, filed Sep. 12, 1995.

EPO Notice of Summons to Oral Proceedings and Preliminary Opinion dated May 20, 2010 from EP Application No. 95931109.3, filed Sep. 12, 1995.

Reply Brief by I.D.I. dated Sep. 6, 2010 to Summons/Preliminary Opinion from EP Application No. 95931109.3, filed Sep. 12, 1995.

Reply Brief by Roche dated Sep. 6, 2010 to Summons/Preliminary Opinion from EP Application No. 95931109.3, filed Sep. 12, 1995 (w/English translation).

EPO Notice of Decision of Appeal dated Oct. 6, 2010 from EP Application No. 95931109.3, filed Sep. 12, 1995.

Christensen et al., Phylogenetic relationships of *Salmonella* based on DNA sequence comparison of atpD encoding the 3 subunit of ATP synthase, FEMS Micro Lett. (1998) 161: 89-96.

Cilia et al., Sequence heterogeneities among 16S Ribosomal RNA sequences, and their effect on phylogenetic analyses at the species level, Clin Chem. ((1999) 45: 451-461.

Clayton et al., Intraspecific variation in small-subunit rRNA sequences in GenBank: Why single sequences may not adequately represent prokaryotic taxa, Int J System Bacteriol. (1995) 45(3): 595-599.

Cleuziat et al., Specific detection of Escherichia coli and Shigella species using fragments of genes coding for b-glucuronidase, FEMS Microbiol. Letters, (1990) 72: 315-322.

Cormican et al., Multiplex PCR for identifying mycobacterial isolates, J Clin Pathol. (1995) 48: 203-205.

Cote et al. Molecular Typing of Haemophilus influenzae Using a DNA Probe and Multiplex PCR, Mol Cell Probes, (1994) 8(1): 23-37.

Cousineau et al., on the Origin of Protein Synthesis Factors: A Gene Duplication/Fusion Model, J Mol Evol (1997) 45: 661-670.

Deneer et al., Species-Specific Detection of Listena Monocytogens by DNA amplification, Appl. Envion Mircobiol. (1991) 57(2): 606-609.

Dickey et al., Emended description of Enterobacter cancerogenus comb nov. Int J System Bacteriol. (1988) 38(4): 371-374.

Dieffenbach et al., General concepts for PCR primer design, Genome Research (1993) 3: 30-37.

Dieffenbach et al. Eds. PCR Primer: A laboratory manual, Kwok et al., Design and use of mismatched and degenerate primers, Cold Spring Harbor Laboratory Press (1995) pp. 143-155.

Dopazo, et al., A Computer Program for the Design of PCR Primers for Diagnosis of Highly Variable Genomes, J Virol Meth. (1993) 41:157-165.

Drmanac et al., DNA Sequence Determination by Hybridization: A strategy for efficient large-scale sequencing, Science (1993) 260: 1649-1652.

Dutilh et al., Specific Amplifications of a DNA Sequence Common Toall Chylamydia Trachomatis Serovars using the Polymerase Chain Reaction, Res Microbiol., (1989),140: 7-16.

Dutka-Malen et al., Detection of Glycopeptide Resistance Genotypes and Identification to the Species Level of Clinically Relevant Enterococci by PCR, J Clin Microbiol. (1995) 31(1): 24-27.

Edwards et al., Multiplex PCR: Advantages, Development, and Applications, PCR Meth. Appl. (1994) 3: 565-575.

Egholm et al., PNA hybridizes to complementary oligonucleotides obeying the Watson-Crick hydrogen-bonding rules, Nature (1993) 365(10): 566-568.

Experimental Protocol concerning Enablement of EP-B1 804 616 signed by Martin Gagnon/Marc Ouellette on Mar. 24, 2004.

Farmer III et al., Enterobacter sakazakii: A new species of "Enterobacteriaceae" isolated from clinical specimens, Int J System Bacter. (1980) 30(3): 569-584.

Farmer III et al., Biochemical identification of new species and biogroups of Enterobacteriaceae isolated from clinical specimens, J Clin Microbiol. (1985) 21(1); 46-76.

Farmer III et al., Escherichia fergusonii and Enterobacter taylorae, two new species of Enterobacteriaceae isolated from clinical specimens, J Clin Microbiol. (1985) 21(1): 77-81.

Farmer III, Proposed Rewording of Rule 10C of the Bacteriological Code, Int J Syst Bacter. (1985) 35(2): 222.

Figueroa et al., Multiplex Polymerase Chain Reaction based Assay for the Detection of Babesia bigemina, Babesia bovis and Anaplasma marginale DNA in Bovine Blood, Vet Parasit., (1993) 50: 69-81.

Filer et al., Duplication of the tufGene, which encodes peptide chain elongation factor Tu, is widespread in gram-negative bacteria, J Bacter. (1981) 148(3): 1006-1011.

Fischer et al., Mannitol-specific Phosphoenolpyruvate-dependent Phosphotransferase System of Enterococcus faecalis: Molecular Cloning and Nucleotide Sequences of the Enzyme III$^{Mt1}$ Gene and the Mannitol-1-phosphate Dehydrogenase Gene, Expression in Escherichia coli, and Comparison of the Gene Products with Similar Enzymes, J Bacteriol. (1991) 173(12): 3709-3715.

Fischer et al., Predicting structures for genome proteins, Curr Opin Struct Biol. (1999) 9: 2008-211.

Fox et al., How Close is Close: 16S rRNA sequence identity may not be sufficient to guarantee species identity, Int J Syst Bacter. (1992) 42(1): 166-170.

Fratamico et al., Detection of Escherichia coli 0157:H7 by multiplex Pcr, J Clin Microbiol., (1995) 33(8): 2188-2191.

Friedland et al., Development of a Polymerase Chain Reaction Assay to Detect the Presence of Streptococcus pneumoniae DNA, Diagn Microbio Infect Dis. (1994) 20(4): 187-193.

Gannon et al., Rapid and Sensitive Method for Detection of Shiga-like Toxin-producing Escherichia coli in Ground Beef Using the Polymerase Chain Reaction, Appl Env Microbiol. (1992) 58(12): 38093815.

Gavini et al., Transfer of Enterobacter agglomerans (Beijerinck 1999) Ewing and Fife 1972 to Pantoea gen. nov. as Pantoea agglomerans comb. Nov. And description of Pantoea dispersa sp nov., Int J System Bacteriol. (1989) 39(3): 337-345.

Geha et al., Multiplex PCR for Identification of Methicillin-Resistant Staphylococci in the Clinical Labortory, J Clin Microbiol. (1994), 32(7): 1768-72.

GenBANK Gi:147581 [online] Sep. 14, 1992 [retrieved on Oct. 12 2008], retrieved from htip://ncbi.nlm.nik.gov/entrez/viewer.fcgi?147581:OLDID:114614 (4 pages).

Gillespie et al., Detection of Streptococcus pneumoniae in sputum samples by PCR, J Clin Microbial. (1994) 32(5): 1308-11.

Gogarten et al., Evolution of the vacuolar $H^+$-ATPase: Implications for the origin off eukaryotes, Proc Natl Acad Sci. USA, 86: 6661-6665.

Gray et al., Cloning, Nucleotide Sequence, and Expression in Escherichia coli of the Exotoxin a Structural Gene of Pseudomonas aeruginosa, Proc Natl Acad Sci USA. (1984) 81(9): 2645-2649.

Greer, Comparative modeling of homologous proteins, Methods in Enzymology, (1991) 202: 239- 252.

Greisen et al., PCR Primers and Probes for the 16S rRNA Gene of Most Species of Pathogenic Bacteria, Including Bacteria Found in Cerebospinal Fluid, J Clin Microbiol. (1994) 32(2): 335-351.

Griffin et al., Eds PCRTechnology—Current Innovations; Sharrocks, Chapter 2: the Design of Primers for PCR; CRC Press (1994) 5-11.

Guay et al., Detection of the Pathogenic Parasite Toxoplasma gondii by Specific Amplification of Ribosomal Sequences Using Comultiplex Polymerase Chain Reaction, J Clin Microbiol. (1993) 31(2): 203-207.

Guex et al., Protein modelling for all (Swiss-Model), TIBS 24 Computer Corner (1999) pp. 364-367.

Gupta et al., Protein phylogenies and signature sequences: a reappraisal of evolutionary relationships among Archaebacteria, Eubacteria, and Eukaryotes, Micro Mol Bio Rev. (1998) 62(4): 1435-1491.

Gutierrez et al., Point Mutations that Reduce the Expression of malPQ, a Positively Controlled Operon of Escherichia coli, J Mol Biol. (1984) 177(1): 69-86.

Harrison et al., Eds Micro Total Analysis Systems '98, Anderson et al., Advances in Integrated Genetic Analysis, Proceedings of the uTAS '98 Workshop, Banff, Canada Oct. 13-16, 1998; Kluwer Academic Publishers, Dordrecht, the Netherlands (1998) pp. 11-16, Heller et al., an integrated microelectronic hybridization system for genomic research and diagnostic applications, pp. 221-224.

Hartl et al., The Population Genetics of Escherichia Coli, Ann Rev Genet. (1984) 18: 31-68.

Hedegaard et al., Identification of Enterobacteriaceae by partial sequencing of the gene encoding translation initiation factor 2, Int J System Bacter. (1999) 49: 1531-1538.

Hill et al., Inversions between ribosomal RNA genes of Escherichia coli, Proc Natl Acad Sci. USA (1981) 78(11): 7069-7072.

Horii et al., Organization of the recA Gene of Escherichia coli, Proc Nati Acad Sci USA. (1980) 77(1): 313-317.

Hotomi et al., Detection of Haemophilus influenzae in Middle Ear of Otitis Media with Effusion by Polymerase Chain Reaction, Int J Pediatr Otorhinolaryngol. (1993) 27(2): 19-26.

Houard, et al. Specific Identification of Bordetella pertussis by the Polymerase Chain Reaction, Res Microbio. (1989) 140: 477-487.

Hynes et al., PCR Amplification of Streptococcal DNA Using Crude Cell Lysates, FWMS Microbiol Lett. (1992) 94: 139-142.

Ibrahim et al., the phylogeny of the genus Yersinia based on 16S rDNA sequences, FEMS Micro Lett. (1993) 114: 173-178.

Innis et al., Eds. Statistical Refinement of Primary Design Parameters, PCR Applications; Beasley et al., Statistical refinement of primer design parameters, Academic Press (1999) Chapter 5: 55-71.

Iwabe et al., Evolutionary relationship of archaebacteria, eubacteria, and eukaryotes inferred from phylogenetic trees of duplicated genes, Proc Natl Acad Sci. USA (1989) 86: 9355-9359.

Izard et al., Deoxyribonucleic acid relatedness between *Enterobacter cloacae* and *Enterobacter amnigenussp* nov., Int J System Bacter. (1981) 31(1): 35-42.

Janda et al., Prototypal diarrheagenic strains of *Hafnia alvei* are actually members of the genus *Escherichia*, J Clin Microbiol. (1999) 37(8): 2399-2401.

Johnson, et al. Urinary Tract Infections in Women: Diagnosis and Treatment, Ann Intern Med. (1989) 111: 906-917.

Kaper et al., Pathogenicity islands and Other Mobile Genetic Elements of Diarrheagenic *Escherichia Coli*, Am Soc Microbio. (1999) 3: 33-58.

Kaufhold et al., Identical Genes Confer High-Level Resistance to Gentamicin upon *Enterococcus faecalis, enterococcus faecium*, and *Streptococcus agalactiae*, Antimicrob Agents Chemother. (1992) 36(6): 1215-1218.

Kearns et al., Rapid Detection of Methicillin-Resistant *Staphylococci* by Multiplex Pcr, J Hosp Infect. (1999) 43: 33-37.

Khan et al.. Detection of *Pseudomonas aeruginosa* from Clinical and Environmental Samples by Amplification of the Exotoxin a Gene Using PCR, Appl Environ Microbiol. (1994) 60(10): 3739-3745.

Kimura, A simple method for estimating evolutionary rates of base substitutions through comparative studies of nucleotide sequences, J Mol Evol (1980) 16: 111-120.

Kitch et al., Evaluation of RApID onE system for identification of 379 strains in the family *Enterobacteriaceae* and oxidase negative, gram-negative nonfermenters, J Clin Microbiol. (1994) 32(4): 931-934.

Kloos et al., Siplified scheme for routine identification of human *Staphylococcus* species, J Clin Microbiol. (1975) 1(1): 82-88.

Kong et al., Co-detection of Three Species of Water-borne Bacteria by Multiplex PCR, Marine Pollution Bulletin, (1995) 31 (4-12): 317-324.

Koshkin et al.; LNA (Locked Nucleic Acids): Synthesis of the Adenine, Cytosine, Guanine, 5-Methylcytosine, Thymine and Uracil bicyclonucleoside monomers, oligomerisation, and unprecedented nucleic acid recognition, Tetrahedron (1998) 54: 3607-3630.

Lawrence et al., Molecular and Evolutionary Relationships Among Enteric Bacteria, J Gen Microbiol. (1991) 137(8): 1911-1921.

Le Bouguenec et al., Rapid and Specific Detection of the pap, afa, and sfa Adhesin-encoding Operons in Uropathogenic *Escherichia coli* Strains by Polymerase Chain Reaction, J Clin Microbiol. (1992) 30(5): 1189-1193.

Lewin, Benjamin, Genes IV, Chapter 3: Genes are mutable units; Oxford University Press (1990) pp. 41-56.

Li et al., Identification of *Bordetella pertussis* Infection by Shared-primer PCR, J Clin Microbiol., (1994) 32(3): 783-789.

Livak et al., Oligonucleotides with fluorescent dyes at opposite ends provide a quenched probe system useful for detecting PCR product and nuclei acid hybridization, PCR Methods & Applications, (1995) Cold Spring Harbor Laboratory Press, 4: 357-362.

Lowe et al., Nucleotide Sequence of the Aliphatic Amidase Regulator Gene (amiR) of *Pseudomonas aeruginosa*, Febs Lett. (1989) 246 (1-2): 39-43.

Ludwig et al., Complete nucleotide sequences of seven eubacterial genes coding for the elongation factor Tu: functional, structural and phylogenetic evaluations, Arch Microbiol. (1990) 153: 241-247.

Ludwig et al., Phylogenetic relationships of *Bacteria* based on comparative sequence analysis of elongation factor Tu and ATP-synthase β-subunit genes, Antonie von Leeuwenhoek (1993) 64: 285-305.

Malloy et al., Detection of Borrelia Burgdorferi Using Polymerase Chain Reaction, J Clin Microbiol. (1990), 28(6): 1089-1093.

McCabe et al., Bacterial species identification after DNA amplification with a universal primer pair, Mol Gen Metabol. (1999) 66: 205-211.

McINTOSH et al., Detection of *Pseudomonas aeruginosa* in Sputum from Cystic Fibrosis Patients by the Polymerase Chain Reactions, Mol Cell Probes (1992) 6(4): 299-304 Abstract.

McMillin et al., Simultaneous Detection of Toxin a and Toxin B Genetic Determinants of *Clostridium difficile* Using the Multiplex Polymerase Chain Reaction, Can J Microbiol., (1992) 38: 81-83.

Miller et al., General microbiology of *recA*: Environmental and evolutionary significance, Ann Rev Microbial. (1990) 44: 365-394.

Mollet et al., *rpoB* sequence analysis as a novel basis for bacterial identification, Mol Microbiol. (1997) 26(5): 1005-1011.

Murray et al., Eds. Manual of Clinical Microbiology; Tang et al., Molecular detection and identification of microorganisms, ASM Press, 7th Ed, (1999) Chapter 13, pp. 215-244.

Neidhardt et al., Eds. *Escherichia coli* and *Salmonella Cellular* and Molecular Biology, Selander et al., Evolutional Genetics of *Salmonella enterica*, ASM Press (1996) 2nd Ed., Chapt: 147: 2691-2707.

Nelson et al., The Evolution of $H^+$-ATPases, TIBS (1989) 14: 113-116.

Nichols et al., A universal nucleoside for use of ambiguous sites in DNA primers, Letters to Nature (1994) 369: 492-493.

Nikiforov et al., The use of 96-well Polystyrene plates for DNA hybridization-based assays: An evaluation of different approaches of oligonucleotide immobilization, Anal. Biochem. (1995) 227: 201209.

Nikiforov et al., The use of phosphorothioate primers and exonuclease hydrolysis for the preparation of single-stranded Pcr products and their detection by solid-phase hybridization, PCR Methods and Applications, (1994) 3: 285-291.

O'Callaghan et al., Development of a PCR Probe Test for Identifying *Pseudomonas aeruginosa* and *Pseudomonas* (*Burkholderia*) *cepacia*, J Clin Pathol. (1994) 47(3): 222-226.

Persing et al., Eds. Diagnostic Molecular Microbiology: Principles and Applications, Nucleic Acid Probes for Detection and Identification of Infectious Agents by Tenover, et al., American Society for Microbiology (1993) pp. 3-25.

Persing et al., Eds. Suppl to Diagnostic Molecular Microbiology: Principles and Applications, Genotypic Methods for microbial identification by Reiman et al., American Society for Microbiology (1996) pp. 3-31.

Pezzlo, Detection of Urinary Tract Infections by Rapid Methods, Clin Microbiol Rev. (1988) 1(2): 268-280.

Pollard et al., a Polymerase Chain Reaction (PCR) Protocol for the Specific Detection of Chlamydia spp., Mol Cell Probes., (1989) 3: 383-389.

Post et al., Molecular Analysis of Bacterial Pathogens in Otitis Media with Effusion, JAMA (1995) 273(20): 1598-1604.

Priebe, et al., Nucleotide Sequence of the *hexA* Gene for DNA Mismatch Repair in *Streptococcus pneumoniae* and Homology of *hexA* to *mutS* of *Escherichia coil* and *Salmonella typhimurium*. J. Bacteriol. (1988) 170: 190-196.

Pritchard et al., Possible Insertion Sequences in a Mosaic Genome Organization Upstream of the Exotoxin a Gene in *Pseudomonas aeruginosa*, J Bacteriol. (1990) 172(4): 2020-2028.

Radstrom et al., Detection of Bacterial DNA in Cerebrospinal Fluid by an Assay for Simultaneous Detection of *Neisseria meningitidis, Haemophilus influenzae*, and *Streptococci* Using a Seminested PCR Strategy, J Clin Microbiol. (1994) 32(11): 2738-2744.

Reeve, Archaebacteria then . . .archaes now (Are there really no. archaeal pathogens? J Bacter. (1999) 181(12): 3613-3617.

Rosa et al., A Specific and Sensitive Assay for the Lyme Disease Spirochete *Borrelia burgdorferi* Using the Polymerase Chain Reaction, J Infect Dis. (1989) 160(6): 1018-1028.

Rosa et al., Polymerase Chain Reaction Analyses Identify Two Distinct Classes of *Borrelia Burgodorferi*, J Clin Microbiol., (1991) 29(3): 524-532.

Rudolph et al., Evaluation of Polymerase Chain Reaction for Diagnosis of Pneumococcal Pneumonia, J Clin Microbiol. (1993) 31(10): 2661-2666.

Ryffel et al., Sequence Comparison of mecA Genes Isolated from Methicillin-resistant *Staphylococcus aureus* and *Staphylococcus epidermidis*, Gene (1990) 94(1): 137-8 (Abstract).

Sali, Modelling mutations and homologous proteins, Curr Opin Biotech. (1995) 6: 437-451.

Sambrook et al., Eds. Molecular Cloning: a Laboratory Manual, 2nd Ed. Cold Spring Harbor Laboratory Press, (1989) pp. pp. 18.35-18.39.

Sànchez et al., Advances in comparative protein-structure modelling, Curr Opin Struct Biol. (1997) 7: 206-214.

Saraste et al., The atp operon: nucleotide sequence of the genes for the γ, β, and ε subunits of *Escherichia coli* ATP synthase, Nucl Acids Res. (1981) 9(20): 5287-5296.

Schaechter et al., Mechanisms of Microbial Disease. The Enteric Bacteria: Diarrhea and Dysentery, Dept Microbial Immunol., (1989), 17: 256-265.

Seta et al., Duplication of the *tuf* Gene: a new insight into the Phylogeny of Eubacteria, J Bacteriol. (1989) 171(1): 581-584.

Sharma et al., Identification of *Yersinia* species by the API 20E, J Clin Microbio. (1990) 28(6): 1443-1444.

Silvestrini et al., Nitrite Reductase from *Pseudomonas aeruginosa*: Sequence of the Gene and the Protein, FEBS Lett. (1989) 254(1-2): 33-38.

Spierings et al., Characterization of the *Citrobacter freundii* phoE Gene and Development of C. freundii-*specific Oligonucleotides*, FEMS Microbiol. Letters (1992) 99:199-204.

Sproer et al., The phylogenetic position of *Serratia*, Buttiauxella and some other genera of the family Enterobacteriaceae, Int J System Bacterial. (1999) 49: 1433-1438.

Stackebrandt et al., Taxonomic note: a place for DNA-DNA reassociation and 16S rRNA sequence analysis in the present species definition in bacteriology, Int J System Bacteriol. (1994) 44(4): 846-849.

Stacy-Phipps et al. Multiplex PCR Assay and Simple Preparation Method for Stool Specimans Detect Enterotoxigenic *Escherichia Coli* DNA during Course of Infection, J Clin Microbio. (1995) 33(5): 1054-1059.

Steigerwalt et al., DNA relatedness among species of *Enterobacter* and *Serratia*, Can J Microbiol. (1976) 22: 121-137.

Su et al., Nucleotide Sequence of the Gelatinase Gene (gelE) from *Enterococcus faecalis* subsp. Liquefaciens, Infect. Immun. (1991) 59(1): 415-420.

Takezaki et al. Phylogenetic test of the molecular clock and linearized trees, Mol Biol Evol. (1995) 12(5): 823-833.

Taylor, Remotely related sequences and structures: analysis and predictive modelling, Trends Biotechnol. (1994) 12(5): 154-158.

Tyagi et al., Molecular beacons: probes that fluoresce upon hybridization, Nature Biotech. (1996) 14: 303-308.

Tyler et al., *Streptococcal* Erythrogenic Toxin Genes: Detection by Polymerase Chain Reaction and Association with Disease in Strains Isolated in Canada from 1940 to 1991, J Clin Microbiol. (1992) 30(12): 3127-3131.

Ubukata et al., Rapid Detection of the mecA Gene in Methicillin-resistant *Staphylococci* by Enzymatic Detection of Polymerase Chain Reaction Products, J Clin Microbiol. (1992) 30(7): 1728-1733.

Ueyama et al., High Incidence of *Haemophilus influenzae* in Nasopharyngeal Secretions and Middle Ear Effusions as Detected by PCR, J Clin Microbiol. (1995) 33(7): 1835-1838.

ÜNal et al., Detection of Methicillin-Resistant *Staphylococci* by Using the Polymerase Chain Reaction, J Clin Microbio., (1992) 1685-1691.

Van Burik et al., Panfungal PCR Assay for Detection of Fungal Infection in Human Blood Specimens, J Clin Microbiol. (1998) 36(5): 1169-1175.

van Ketel, Detection of *Haemophilus influenzae* in Cerebrospinal Fluids by Polymerase Chain Reaction DNA Amplification, J Med Microbiol., (1990) 33: 271-276.

Vannuffel et al., Specific Detection of Methicillin-Resistant *Staphylococcus* Species by Multiplex PCR, J Clin Microbiology, (1995) 2864-2867.

Vijgenboom et al., Three *tuf*-like genes in the Kirromycin producer *Strept myc s ramocissimus*, Microbiol. (1994) 140: 983-998.

Wang et al., a 16S rDNA-based PCR Method for Rapid and Specific Detection of Clostridium perfringens in Food, Mol Cell Probes (1994) 8(2): 131-137.

Wang et al., Phylogenetic analysis and identification of *Shigeo spp* by molecular probes, *Mol Cell Probes* (1997) 11: 427-432.

Watson et al., Molecular Biology of the Gene, Vol. I - Geneial Principles; 4th Ed. The Benjamin/Cummings Publishing Company, Inc., (1987) pp. 431-462.

Way et al., Specific Detection of *Salmonella spp*. By Multiplex Polymerase Chain Reaction, App Environ Microbiol. (1993) 59(5): 1473-1479.

Wayne et al., Report of the Ad Hoc Committee on Reconciliation of approaches to bacterial systematics, Int J Sys Bacter. (1987) 37(4): 463-464.

Weaver et al., Incidence of methanogenic bacteria in a sigmoidoscopy population: an association of methanogenic bacteria and diverticulosis, Gut 27: 698-704. .

Weickmann and Weickmann, Reference D34, European Opposition for EP 0804616Spezifität der Primer, ANNEX II: Specific and ubiquitous primers for DNA amplification, 11 pages, (Sep. 13, 2007).

Weickmann and Weickmann, Reference D35, European Opposition for EP 0804616, Vergleich: Bacterial species: *Escherichia coli* (Sep. 13, 2007).

Weickmann and Weickmann, Reference D40, European Opposition for EP 0804616, Comparison of Sequences TRP.OO3 and TRP.004 of WO 93/12245 with SEQ ID No. 5 of EP 804616 (Sep. 13, 2007).

Weickmann and Weickmann, Reference D43, European Opposition for EP 0804616Comparison of Sequence E. coli malPQ operon, 5'-end of Gutierrez et al., J. Mol. Biol. 177(1) (1984) 69-86 with SEQ ID No: 6 (glycogen phosphorylase) of EP 804616; of Sequence *E.coli* recA gene, 5'-region of Zhao et al., Mol.Gen.Genet. 222(2-3) (1990) 369-376 with SEQ ID No: 7 of EP 804616, and of exotoxin a gene of Chen et al., J. Gen. Microbial. 133(11) (1987) 3081-3091 with SEQ ID No:18 of EP 804616 (Sep. 13, 2007).

Weickmann and Weickmann, Reference D49, European Opposition for EP 0804616, Vergleich der SEQ ID No. 26 (*Haemophilus influenzae* omp P1 gene) aus EP804616 und Sonde 106b aus EP804616 mit Primer Homp1 und Homp3 aus Cote S. Et al., Mol. Cell. Probes (Feb. 1994) 8:23-37 (Sep. 13, 2007).

Weickmann and Weickmann, Reference D50, European Opposition for EP 0804616, Vergleich der SEQ ID No. 27 (*Haemophilus influenzaetransformation* gene cluster) und Primer 154 bzw 155b Lind Sonde 107b aus EP804616 mit Primer Htra3 aus Cote S. Et al., Mol. Cell. Probes (Feb. 1994) 8:23-37.

Weickmann and Weickmann, Reference D52, European Opposition for EP 0804616, Comparison of SEQ ID No. 8 to 21 of EP577523 with neuraminidase nanA of *Streptococcus pneumoniae* (cf. SEQ ID No. 35 of EP804616).

Weickmann and Weickmann, Reference D54, European Opposition for EP 0804616, Comparison of SEQ ID No. 1 and Primers YR2 and YR6 of FR2686604 with primers SEQ ID No. 141 and 142 of EP804616 (Sep. 13, 2007).

Weickmann and Weickmann, Reference 056, European Opposition for EP 0804616, Vergleich der SEQ ID No. 33 (*Streptococcus pyogenes* Exotoxin a gene) aus EP804616 und Primern SEQ ID Nos. 143 bzw. 144b (EP804616) mit speA-Primern P1-P4 aus Black C.M. et al., Mol. Cell. Probes (1993) 7: 255-259 und speA-primem Spea-1, Spea-2 aus Tyler S.D. et al., J.Clin.Microbiol.Dis. (1992) 30:31273131 (Sep. 13, 2007).

Weickmann and Weickmann, Reference D58, European Opposition for EP 0804616, References for target genes (Sep. 13, 2007).

Weickmann and Weickmann, Reference D72, European Opposition for EP 0804616Vergleich der SEQ ID Nos. 18 und 20 (*Pseudomonas aeruginosa*) aus EP804616 und der entsprechenden Probesequenzen SEQ ID Nos. 87-90 und 94+95 mit Primer und Probesequenzen ETA1-ETA7 aus Khan et al., Appl. Environment. Microbial. Oct. 1994.

Westin et al., Anchored multiplex amplification on a microelectronic chip array, Nature Biotech. (2000) 18: 199-204.

Whitcombe et al., Detection of PCR products using self-probing amplicons and fluorescence, Nature Biotech. (1999) 17: 804-807.

White et al., The Polymerase Chain Reaction: Clinical Applications, Adv Clin Chem. (1992) 29: 161-196.

Wilson et al., Detection of Enterotoxigenic *Staphlococcus aureus* in Dried Skimmed Milk: Use of the Polymerase Chain Reaction for Amplification and Detection of *Staphylococcal Enterotoxin* Genes entB and entC1 and the Thermonuclease Gene nuc. Appl Environ Microbiol., (1991) 1793-1798.

Wittwer et al., Rapid Cycle DNA Amplification: Time and Temperature Optimization, Biotechniques (1991) 10(1): 76-83.

Wittwer et al., The LightCycler™: a microvolume multisample fluorimeter with rapid temperature control, Bio Techniques (1997) 22: 176-181.

Yanofsky et al., the Complete Nucleotide Sequence of the Tryptophan Operon of *Escherichia coli*. Nucleic Acids Res. (1981) 9(24): 6647-6668.

Zakrewska-Czerwinska et al., Identification of *Staphylococcus epidermidis* Using a 16S rRNA-directed Oligonucleotide Probe, FEMS Microbiol Lett. (1992) 100: 51-58.

Zambardi et al., Laboratory Diagnosis of Oxacillin Resistance in *Staphylococcus aureus* by a Multiplex-polymerase Chain Reaction Assay, Diagn Microbiol Infect Dis. (1994) 19: 25-31.

Zhao et al., DNA Sequence Analysis of the recA Genes from *Proteus vulgaris, Erwinia carotovora, Shigella flexneri* and *Escherichia coli* B/r, Mol Gen Genet. (1990) 222(2-3): 369-376.

* cited by examiner

SEQUENCE LISTING

<160> NUMBER OF SEQ ID NOS: 174

<210> SEQ ID NO 1
<211> LENGTH: 22
<212> TYPE: DNA
<213> ORGANISM: Enterococcus faecium

<400> SEQUENCE: 1

```
tgctttagca acagcctatc ag                                              22

<210> SEQ ID NO 2
<211> LENGTH: 21
<212> TYPE: DNA
<213> ORGANISM: Enterococcus faecium

<400> SEQUENCE: 2
taaacttctt ccggcacttc g                                               21

<210> SEQ ID NO 3
<211> LENGTH: 21
<212> TYPE: DNA
<213> ORGANISM: Listeria monocytogenes

<400> SEQUENCE: 3
tgcggctata aatgaagagg c                                               21

<210> SEQ ID NO 4
<211> LENGTH: 21
<212> TYPE: DNA
<213> ORGANISM: Listeria monocytogenes

<400> SEQUENCE: 4
atccgatgat gctatggctt t                                               21

<210> SEQ ID NO 5
<211> LENGTH: 21
<212> TYPE: DNA
<213> ORGANISM: Neisseria meningitidis

<400> SEQUENCE: 5
ccagcggtat tgtttggtgg t                                               21

<210> SEQ ID NO 6
<211> LENGTH: 21
<212> TYPE: DNA
<213> ORGANISM: Neisseria meningitidis

<400> SEQUENCE: 6
caggcggcct ttaataattt c                                               21

<210> SEQ ID NO 7
<211> LENGTH: 30
<212> TYPE: DNA
<213> ORGANISM: Staphylococcus saprophyticus

<400> SEQUENCE: 7
agatcgaatt ccacatgaag gttattatga                                      30

<210> SEQ ID NO 8
<211> LENGTH: 30
<212> TYPE: DNA
<213> ORGANISM: Staphylococcus saprophyticus

<400> SEQUENCE: 8
tcgcttctcc ctcaacaatc aaactatcct                                      30

<210> SEQ ID NO 9
<211> LENGTH: 23
<212> TYPE: DNA
<213> ORGANISM: Streptococcus agalactiae

<400> SEQUENCE: 9
```

```
tttcaccagc tgtattagaa gta                                              23

<210> SEQ ID NO 10
<211> LENGTH: 23
<212> TYPE: DNA
<213> ORGANISM: Streptococcus agalactiae

<400> SEQUENCE: 10
gttccctgaa cattatcttt gat                                              23

<210> SEQ ID NO 11
<211> LENGTH: 26
<212> TYPE: DNA
<213> ORGANISM: Candida albicans

<400> SEQUENCE: 11
caagaaggtt ggttacaacc caaaga                                           26

<210> SEQ ID NO 12
<211> LENGTH: 26
<212> TYPE: DNA
<213> ORGANISM: Candida albicans

<400> SEQUENCE: 12
aggtcttacc agtaacttta ccggat                                           26

<210> SEQ ID NO 13
<211> LENGTH: 22
<212> TYPE: DNA
<213> ORGANISM: Enterococcus sp.

<400> SEQUENCE: 13
tactgacaaa ccattcatga tg                                               22

<210> SEQ ID NO 14
<211> LENGTH: 21
<212> TYPE: DNA
<213> ORGANISM: Enterococcus sp.

<400> SEQUENCE: 14
aacttcgtca ccaacgcgaa c                                                21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 15
ctggcgcggt atggtcggtt                                                  20

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 16
gccgacgttg gaagtggtaa ag                                               22

<210> SEQ ID NO 17
```

```
<211> LENGTH: 25
<212> TYPE: DNA
<213> ORGANISM: Staphylococcus sp.

<400> SEQUENCE: 17
ccgtgttgaa cgtggtcaaa tcaaa                                          25

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 18
trtgtggtgt ratwgwrcca ggagc                                          25

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 19
acaacgtggw caagtwttag cwgct                                          25

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 20
accatttcwg taccttctgg taagt                                          25

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: synthetic
      DNA
<220> FEATURE:
<221> NAME/KEY: modified_base
<222> LOCATION: (12)
<223> OTHER INFORMATION: i

<400> SEQUENCE: 21
gaaattgcag gnaaattgat tga                                            23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: synthetic
      DNA
<220> FEATURE:
<221> NAME/KEY: modified_base
<222> LOCATION: (12)
<223> OTHER INFORMATION: i

<400> SEQUENCE: 22
ttacgcatgg cntgactcat cat                                            23
```

```
<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: synthetic
      DNA
<220> FEATURE:
<221> NAME/KEY: modified_base
<222> LOCATION: (3)
<223> OTHER INFORMATION: i
<220> FEATURE:
<221> NAME/KEY: modified_base
<222> LOCATION: (6)
<223> OTHER INFORMATION: i
<220> FEATURE:
<221> NAME/KEY: modified_base
<222> LOCATION: (9)
<223> OTHER INFORMATION: i
<220> FEATURE:
<221> NAME/KEY: modified_base
<222> LOCATION: (12)
<223> OTHER INFORMATION: i
<220> FEATURE:
<221> NAME/KEY: modified_base
<222> LOCATION: (15)
<223> OTHER INFORMATION: i

<400> SEQUENCE: 23
acnkknacng gngtngarat gtt                                              23

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: synthetic
      DNA
<220> FEATURE:
<221> NAME/KEY: modified_base
<222> LOCATION: (6)
<223> OTHER INFORMATION: i
<220> FEATURE:
<221> NAME/KEY: modified_base
<222> LOCATION: (9)
<223> OTHER INFORMATION: i
<220> FEATURE:
<221> NAME/KEY: modified_base
<222> LOCATION: (12)
<223> OTHER INFORMATION: i
<220> FEATURE:
<221> NAME/KEY: modified_base
<222> LOCATION: (18)
<223> OTHER INFORMATION: i

<400> SEQUENCE: 24
ayrttntcnc cnggcatnac cat                                              23

<210> SEQ ID NO 25
<211> LENGTH: 10
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 25
tcgcttctcc                                                             10

<210> SEQ ID NO 26
<211> LENGTH: 600
<212> TYPE: DNA
```

<213> ORGANISM: Enterococcus faecium

<400> SEQUENCE: 26

| | | | | | |
|---|---|---|---|---|---|
| ttcttagaga | cattgaatat | gccttatgtc | ggcgcaggcg | tattgaccag | tgcatgtgcc | 60 |
| atggataaaa | tcatgaccaa | gtatatttta | caagctgctg | gtgtgccgca | agttccttat | 120 |
| gtaccagtac | ttaagaatca | atggaaagaa | aatcctaaaa | aagtatttga | tcaatgtgaa | 180 |
| ggttcttgc | tttatccgat | gtttgtcaaa | cctgcgaata | tgggttctag | tgtcggcatt | 240 |
| acaaaggcag | aaaaccgaga | gagctgcaa | aatgctttag | caacagccta | tcagtatgat | 300 |
| tctcgagcaa | tcgttgaaca | aggaattgaa | gcgcgcgaaa | tcgaagttgc | tgtattagga | 360 |
| aatgaagatg | ttcggacgac | tttgcctggc | gaagtcgtaa | aagacgtagc | attctatgat | 420 |
| tatgaagcca | atatatcaa | taataaaatc | gaaatgcaga | ttccagccga | agtgccggaa | 480 |
| gaagtttatc | aaaaagcgca | agagtacgcg | aagttagctt | acacgatgtt | aggtggaagc | 540 |
| ggattgagcc | ggtgcgattt | cttttttgaca | aataaaaatg | aattattcct | gaatgaatta | 600 |

<210> SEQ ID NO 27
<211> LENGTH: 1920
<212> TYPE: DNA
<213> ORGANISM: Listeria monocytogenes

<400> SEQUENCE: 27

| | | | | | |
|---|---|---|---|---|---|
| gtgggattaa | acagatttat | gcgtgcgatg | atggtggttt | tcattactgc | caattgcatt | 60 |
| acgattaacc | ccgacataat | atttgcagcg | acagatagcg | aagattctag | tctaaacaca | 120 |
| gatgaatggg | aagaagaaaa | aacagaagag | caaccaagcg | aggtaaatac | gggaccaaga | 180 |
| tacgaaactg | cacgtgaagt | aagttcacgt | gatattaaag | aactagaaaa | atcgaataaa | 240 |
| gtgagaaata | cgaacaaagc | agacctaata | gcaatgttga | agaaaaagc | agaaaaaggt | 300 |
| ccaaatatca | ataataacaa | cagtgaacaa | actgagaatg | cggctataaa | tgaagaggct | 360 |
| tcaggagccg | accgaccagc | tatacaagtg | gagcgtcgtc | atccaggatt | gccatcggat | 420 |
| agcgcagcgg | aaattaaaaa | aagaaggaaa | gccatagcat | catcggatag | tgagcttgaa | 480 |
| agccttactt | atccggataa | accaacaaaa | gtaaataaga | aaaagtggc | gaaagagtca | 540 |
| gttgcggatg | cttctgaaag | tgacttagat | tctagcatgc | agtcagcaga | tgagtcttca | 600 |
| ccacaacctt | taaagcaaa | ccaacaacca | ttttcccta | agtatttaa | aaaaataaaa | 660 |
| gatgcgggga | atgggtacg | tgataaaatc | gacgaaaatc | ctgaagtaaa | gaaagcgatt | 720 |
| gttgataaaa | gtgcagggtt | aattgaccaa | ttattaacca | aaaagaaaag | tgaagaggta | 780 |
| aatgcttcgg | acttcccgcc | accacctacg | gatgaagagt | taagacttgc | tttgccagag | 840 |
| acaccaatgc | ttcttggttt | taatgctcct | gctacatcag | aaccgagctc | attcgaattt | 900 |
| ccaccaccac | ctacggatga | agagttaaga | cttgctttgc | cagagacgcc | aatgcttctt | 960 |
| ggttttaatg | ctcctgctac | atcggaaccg | agctcgttcg | aatttccacc | gcctccaaca | 1020 |
| gaagatgaac | tagaaatcat | ccgggaaaca | gcatcctcgc | tagattctag | ttttacaaga | 1080 |
| ggggatttag | ctagtttgag | aaatgctatt | aatcgccata | gtcaaaattt | ctctgatttc | 1140 |
| ccaccaatcc | caacagaaga | agagttgaac | gggagaggcg | gtagaccaac | atctgaagaa | 1200 |
| tttagttcgc | tgaatagtgg | tgattttaca | gatgacgaaa | acagcgagac | aacagaagaa | 1260 |
| gaaattgatc | gcctagctga | tttaagagat | agaggaacag | gaaaacactc | aagaaatgcg | 1320 |
| ggttttttac | cattaaatcc | gtttgctagc | agcccggttc | cttcgttaag | tccaaaggta | 1380 |
| tcgaaaatac | gcgaccgggc | tctgataagt | gacataacta | aaaaacgcc | atttaagaat | 1440 |

-continued

```
ccatcacagc cattaaatgt gtttaataaa aaaactacaa cgaaaacagt gactaaaaaa      1500
ccaacccctg taaagaccgc accaaagcta gcagaacttc ctgccacaaa accacaagaa      1560
accgtactta gggaaaataa aacacccttt atagaaaaac aagcagaaac aaacaagcag      1620
tcaattaata tgccgagcct accagtaatc caaaagaag ctacagagag cgataaagag       1680
gaaatgaaac cacaaaccga ggaaaaatg gtagaggaaa gcgaatcagc taataacgca       1740
aacggaaaaa atcgttctgc tggcattgaa gaaggaaaac taattgctaa agtgcagaa       1800 gacgaaaaag cgaaggaaga accagggaac catacgacgt taattcttgc aatgttagct      1860
attggcgtgt tctctttagg ggcgtttatc aaaattattc aattaagaaa aaataattaa      1920

<210> SEQ ID NO 28
<211> LENGTH: 415
<212> TYPE: DNA
<213> ORGANISM: Neisseria meningitidis

<400> SEQUENCE: 28
taccggtacg ctaaatattg gtgatgtatt ggatattatg atttgggaag cgccgccagc        60
ggtattgttt ggtggtggcc tttcttcgat gggctcgggt agtgcgcaac aaaccaagtt       120
gccggagcaa ctggtgacgg cacgtggtac ggtttctgtg ccgtttgttg gcgatatttc       180
ggtggtcggt aaaacgcctg gtcaggttca ggaaattatt aaaggccgcc tgaaaaaaat       240
ggccaatcag ccgcaagtga tggtgcgctt ggtgcagaat aatgcggcaa atgtatcggt       300
gattcgcgca gcaatagtg tgcgtatgcc gttgacggca gccggtgagc gtgtgttgga       360
tgcggtggct gcggtaggtg gttcaacggc aaatgtgcag gatacgaatg tgcag           415

<210> SEQ ID NO 29
<211> LENGTH: 438
<212> TYPE: DNA
<213> ORGANISM: Staphylococcus saprophyticus

<400> SEQUENCE: 29
tcgcttctcc agaagaaatt ttagaaacat atctagaaaa tcccaaatta gataaaccgt         60
ttatattatg tgaatacgca catgcaatgg gaaattcacc aggagatctt aatgcatatc       120
aaacattaat tgaaaatat gatagtttta ttggcggttt tgtttgggaa tggtgtgatc       180
atagcattca ggttgggata aaggaaggta accaatttt tagatatggt ggagattttg       240
gtgaggcctt acatgacggt aattttttgtg ttgatggtat tgtttcgcca gatcgaattc      300
cacatgaagg ttattatgag tttaaacatg aacatagacc tttgagattg gttaacgaag      360
aggattatcg gtttacattg aagaatcaat ttgattttac aaatgcggag gatagtttga      420
ttgttgaggg agaagcga                                                      438

<210> SEQ ID NO 30
<211> LENGTH: 768
<212> TYPE: DNA
<213> ORGANISM: Streptococcus agalactiae

<400> SEQUENCE: 30
atgaacgtta cacatatgat gtatctatct ggaactctag tggctggtgc attgttattt         60
tcaccagctg tattagaagt acatgctgat caagtgacaa ctccacaagt ggtaaatcat       120
gtaaatagta ataatcaagc ccagcaaatg gctcaaaagc ttgatcaaga tagcattcag       180
ttgagaaata tcaaagataa tgttcaggga acagattatg aaaaaccggt taatgaggct       240
attactagcg tggaaaaatt aaagacttca ttgcgtgcca accctgagac agtttatgat       300
```

```
ttgaattcta ttggtagtcg tgtagaagcc ttaacagatg tgattgaagc aatcactttt    360
tcaactcaac atttaacaaa taaggttagt caagcaaata ttgatatggg atttgggata    420
actaagctag ttattcgcat tttagatcca tttgcttcag ttgattcaat aaagctcaa     480 gttaacgatg taaaggcatt agaacaaaaa gttttaactt atcctgattt aaaaccaact    540
gatagagcta ccatctatac aaaatcaaaa cttgataagg aaatctggaa tacacgcttt    600
actagagata aaaagtact taacgtcaaa gaatttaaag tttacaatac tttaaataaa     660
gcaatcacac atgctgttgg agttcagttg aatccaaatg ttacggtaca acaagttgat    720
caagagattg taacattaca agcagcactt caaacagcat aaaataa                 768
```

<210> SEQ ID NO 31
<211> LENGTH: 421
<212> TYPE: DNA
<213> ORGANISM: Neisseria meningitidis

<400> SEQUENCE: 31

```
atgaaagtag gtttcgtcgg ctggcgcggt atggtcggtt cggttttgat gcagcgtatg     60
aaagaagaaa acgacttcgc ccacattccc gaagcgtttt tctttaccac ttccaacgtc    120
ggcggcgcac gccctgattt cggtcaggcg gctaaaacat tattggacgc gaacaacgtt    180
gccgagctgg caaaaatgga catcatcgtt acctgccaag gcggcgacta caccaaatcc    240
gtcttccaag ccctgcgcga cagcggctgg aacggctact ggattgacgc ggcatcctcg    300
ctgcgtatga agacgacgc gattatcgtc ctcgaccccg tcaaccgcaa cgtcatcgac    360
aacggcctca aaacggcgt gaaaaactac atcggcggca actgtaccgt ttccctgatg    420
c                                                                    421
```

<210> SEQ ID NO 32
<211> LENGTH: 213
<212> TYPE: DNA
<213> ORGANISM: Streptococcus gordonii

<400> SEQUENCE: 32

```
ttcatagacg ctgagcacgc tttggatcca tcttacgcgg ctgctctagg tgtaaatatt     60
gatgagctgt tgctatctca accagattct ggtgagcaag gtttagaaat tgcaggaaaa    120
ttgattgact ctggggcagt tgatttagtt gtcatcgact ctgttgcagc tcttgtacca    180
cgtgcggaaa tcgatggaga tatcggtgat agc                                 213
```

<210> SEQ ID NO 33
<211> LENGTH: 692
<212> TYPE: DNA
<213> ORGANISM: Streptococcus mutans

<400> SEQUENCE: 33

```
gggccggaat cttctggtaa gacaactgtc gctcttcatg ctgctgctca ggcgcaaaaa     60
gatggcggta ttgccgcttt cattgatgca gaacatgccc ttgatccagc ctatgctgct    120
gctcttggcg ttaatattga tgagcttttg ctttcacaac cagattcagg agaacagggt    180
cttgaaattg cagggaaatt gattgattct ggcgctgttg atttagttgt tgttgactca    240
gtggcagctt tagtaccacg tgcggagatt gacggagata ttggtaatag tcatgttggc    300
ttacaagcac gcatgatgag tcaagcgatg cgtaaattat cagcttcaat caataaaaca    360
aaaaccattg ctatttttat taatcaattg cgggaaaaag ttggtattat gtttggtaat    420
ccagaaacaa cccctggcgg gcgtgccttg aagttttatt cttctgtgcg tcttgatgtc    480
```

| | |
|---|---|
| cgcggcaata ctcaaattaa aggaaccggg gaacaaaaag acagcaatat tggtaaagag | 540 |
| accaaaatta aagttgttaa aaataaagtt gctccaccat ttaaggaagc ttttgtagaa | 600 |
| attatatatg gtgaaggcat ttctcgtaca ggtgaattag ttaagattgc cagtgatttg | 660 |
| ggaattatcc aaaaagctgg agcttggtac tc | 692 |

<210> SEQ ID NO 34
<211> LENGTH: 1204
<212> TYPE: DNA
<213> ORGANISM: Streptococcus pneumoniae

<400> SEQUENCE: 34

| | |
|---|---|
| atggcgaaaa aaccaaaaaa attagaagaa atttcaaaaa aatttggggc agaacgtgaa | 60 |
| aaggccttga tgacgctct taaattgatt gagaaagact ttggtaaagg atcaatcatg | 120 |
| cgtttgggtg aacgtgcgga gcaaaaggtg caagtgatga gctcaggttc tttagctctt | 180 |
| gacattgccc ttggctcagg tggttatcct aagggacgta tcatcgaaat ctatggccca | 240 |
| gagtcatctg gtaagacaac ggttgccctt catgcagttg cacaagcgca aaaagaaggt | 300 |
| gggattgctg cctttatcga tgcggaacat gcccttgatc cagcttatgc tgcggccctt | 360 |
| ggtgtcaata ttgacgaatt gctcttgtct caaccagact caggagagca aggtcttgag | 420 |
| attgcgggaa aattgattga ctcaggtgca gttgatcttg tcgtagtcga ctcagttgct | 480 |
| gcccttgttc ctcgtgcgga aattgatgga gatatcggag atagccatgt tggtttgcag | 540 |
| gctcgtatga tgagccaggc catgcgtaaa cttggcgcct ctatcaataa aaccaaaaca | 600 |
| attgccattt ttatcaacca attgcgtgaa aaagttggag tgatgtttgg aaatccagaa | 660 |
| acaacaccgg gcggacgtgc tttgaaattc tatgcttcag tccgcttgga tgttcgtggt | 720 |
| aatacacaaa ttaagggaac tggtgatcaa aagaaaacca atgtcggtaa agaaactaag | 780 |
| attaaggttg taaaaaataa ggtagctcca ccgtttaagg aagccgtagt tgaaattatg | 840 |
| tacggagaag gaatttctaa gactggtgag cttttgaaga ttgcaagcga tttggatatt | 900 |
| atcaaaaaag caggggcttg gtattcttac aaagatgaaa aaattgggca aggttctgag | 960 |
| aatgctaaga aatacttggc agagcaccca gaaatctttg atgaaattga taagcaagtc | 1020 |
| cgttctaaat ttggcttgat tgatggagaa gaagtttcag aacaagatac tgaaaacaaa | 1080 |
| aaagatgagc caaagaaaga agaagcagtg aatgaagaag ttccgcttga cttaggcgat | 1140 |
| gaacttgaaa tcgaaattga agaataagct gttaaagcag tggagaaatc cgctactttt | 1200 |
| tcga | 1204 |

<210> SEQ ID NO 35
<211> LENGTH: 981
<212> TYPE: DNA
<213> ORGANISM: Streptococcus pyogenes

<400> SEQUENCE: 35

| | |
|---|---|
| atgcgttcag gaagtctagc tcttgatatt gcttggatag ctggtggtta tcctaaagga | 60 |
| cgtatcatcg aaatctatgg tccagagtct tccggtaaaa cgactgtggc tttacatgct | 120 |
| gtagcacaag ctcaaaaaga aggtggaatc gcagccttta tcgatgccga gcatgcgctt | 180 |
| gatccagctt atgctgctgc gcttgggggtt aatattgatg aacttctctt gtctcaacca | 240 |
| gattctggag aacaaggact tgaaattgca ggtaaattga ttgattctgg tgcggttgac | 300 |
| ctggttgttg tcgattcagt agcagcttta gtgccacgtg ctgaaattga tggtgatatt | 360 |
| ggcgatagcc atgtcggatt gcaagcacgt atgatgagtc aggccatgcg taaattatca | 420 |

```
gcttctatta ataaaacaaa aactatcgca atctttatca accaattgcg tgaaaaagtt      480
ggtgtgatgt ttggaaatcc tgaaacaaca ccaggtggtc gagctttgaa attctatgct      540
tctgttcggc tggatgtgcg tggaaacaac caaattaaag gaactggtga ccaaaagata      600
gccagcattg gtaaggagac caaaatcaag gttgttaaaa acaaggtcgc tccgccattt      660
aaggtagcag aagttgaaat catgtatggg aaggtatttc tcgtacaggg gagcttgtg       720 aaaattgctt ctgatttgga cattatccaa aaagcaggtg cttggttctc ttataatggt      780
gagaagattg gccaaggttc tgaaaatgct aagcgttatt tggccgatca tccacaattg      840
tttgatgaaa tcgaccgtaa agtacgtgtt aaatttggtt tgcttgaaga aagcgaagaa      900
gaatctgcta tggcagtagc atcagaagaa accgatgatc ttgctttaga tttagataat      960
ggtattgaaa ttgaagatta a                                                981

<210> SEQ ID NO 36
<211> LENGTH: 312
<212> TYPE: DNA
<213> ORGANISM: Streptococcus salivarius

<400> SEQUENCE: 36
gcgtatgcac gagctctagg tgttaatatc gatgagcttc ttttgtcgca gcctgattct       60
ggtgagcaag gtctcgaaat tgcaggtaag ctgattgact ctggtgcagt ggatttagtt      120
gttgttgact cagttgcggc cttcgtacca cgtgcagaaa ttgatggaga tagtggtgac      180
agtcatgtag gacttcaagc gcgtatgatg agtcaagcca tgcgtaaact ttctgcatct      240
attaataaaa caaaaacgat tgctatcttt attaaccagt tgcgtgaaaa agttggtatc      300
atgtttggta ac                                                         312

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 37
ctatgtggcg cggtattatc                                                  20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 38
cgcagtgtta tcactcatgg                                                  20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 39
ctgaatgaag ccataccaaa                                                  20
```

```
<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 40
atcagcaata aaccagccag                                                 20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 41
ttaccatgag cgataacagc                                                 20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 42
ctcattcagt tccgtttccc                                                 20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 43
cagctgctgc agtggatggt                                                 20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 44
cgctctgctt tgttattcgg                                                 20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 45
tacgccaaca tcgtggaaag                                                 20

<210> SEQ ID NO 46
<211> LENGTH: 20
```

```
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 46
ttgaatttgg cttcttcggt                                              20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 47
gggatacaga aacgggacat                                              20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 48
taaatctttt tcaggcagcg                                              20

<210> SEQ ID NO 49
<211> LENGTH: 25
<212> TYPE: DNA
<213> ORGANISM: Escherichia coli

<400> SEQUENCE: 49
gatggtttga agggtttatt ataag                                        25

<210> SEQ ID NO 50
<211> LENGTH: 25
<212> TYPE: DNA
<213> ORGANISM: Escherichia coli

<400> SEQUENCE: 50
aatttagtgt gtttagaatg gtgat                                        25

<210> SEQ ID NO 51
<211> LENGTH: 21
<212> TYPE: DNA
<213> ORGANISM: Enterococcus faecalis

<400> SEQUENCE: 51
acttcaacac ctgctgcttt c                                            21

<210> SEQ ID NO 52
<211> LENGTH: 21
<212> TYPE: DNA
<213> ORGANISM: Enterococcus faecalis

<400> SEQUENCE: 52
tgaccacttt tatcagcaac c                                            21

<210> SEQ ID NO 53
<211> LENGTH: 20
<212> TYPE: DNA
```

<213> ORGANISM: Artificial Sequence
<220> FEATURE:
<223> OTHER INFORMATION: Description of Artificial Sequence: synthetic
      DNA

<400> SEQUENCE: 53
ggcaatagtt gaaatgctcg                                           20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 54
cagctgttac aacggactgg                                           20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 55
tctatgatct cgcagtctcc                                           20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 56
atcgtcaccg taatctgctt                                           20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 57
cattctcgat tgctttgcta                                           20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 58
ccgaaatgct tctcaagata                                           20

<210> SEQ ID NO 59
<211> LENGTH: 20
<212> TYPE: DNA
<213> ORGANISM: Artificial Sequence
<220> FEATURE:

```
<223> OTHER INFORMATION: Description of Artificial Sequence: synthetic
      DNA

<400> SEQUENCE: 59
ctggattatg gctacggagt                                                  20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 60
agcagtgtga tggtatccag                                                  20

<210> SEQ ID NO 61
<211> LENGTH: 20
<212> TYPE: DNA
<213> ORGANISM: Pseudomonas aeruginosa

<400> SEQUENCE: 61
gactcttgat gaagtgctgg                                                  20

<210> SEQ ID NO 62
<211> LENGTH: 20
<212> TYPE: DNA
<213> ORGANISM: Pseudomonas aeruginosa

<400> SEQUENCE: 62
ctggtctatt cctcgcactc                                                  20

<210> SEQ ID NO 63
<211> LENGTH: 20
<212> TYPE: DNA
<213> ORGANISM: Pseudomonas aeruginosa

<400> SEQUENCE: 63
tatgagaagg caggattcgt                                                  20

<210> SEQ ID NO 64
<211> LENGTH: 20
<212> TYPE: DNA
<213> ORGANISM: Pseudomonas aeruginosa

<400> SEQUENCE: 64
gctttctctc gaaggcttgt                                                  20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 65
gagttgctgt tcaatgatcc                                                  20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: synthetic
```

-continued

<210> SEQ ID NO 66
...
DNA

<400> SEQUENCE: 66
gtgtttgaac catgtacacg                                              20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 67
tgtagaggtc tagcccgtgt                                              20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 68
acggggataa cgactgtatg                                              20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 69
ataaagatga taggccggtg                                              20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 70
tgctgtcata ttgtcttgcc                                              20

<210> SEQ ID NO 71
<211> LENGTH: 20
<212> TYPE: DNA
<213> ORGANISM: Enterococcus faecalis

<400> SEQUENCE: 71
attatcttcg gcggttgctc                                              20

<210> SEQ ID NO 72
<211> LENGTH: 20
<212> TYPE: DNA
<213> ORGANISM: Enterococcus faecalis

<400> SEQUENCE: 72
gactatcggc ttcccattcc                                              20

<210> SEQ ID NO 73

```
<211> LENGTH: 20
<212> TYPE: DNA
<213> ORGANISM: Enterococcus faecalis

<400> SEQUENCE: 73
cgatagaagc agcaggacaa                                              20

<210> SEQ ID NO 74
<211> LENGTH: 20
<212> TYPE: DNA
<213> ORGANISM: Enterococcus faecalis

<400> SEQUENCE: 74
ctgatggatg cggaagatac                                              20

<210> SEQ ID NO 75
<211> LENGTH: 21
<212> TYPE: DNA
<213> ORGANISM: Enterococcus gallinarum

<400> SEQUENCE: 75
gccttatgta tgaacaaatg g                                            21

<210> SEQ ID NO 76
<211> LENGTH: 23
<212> TYPE: DNA
<213> ORGANISM: Enterococcus gallinarum

<400> SEQUENCE: 76
gtgactttwg tgatcccttt tga                                          23

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 77
tccaatcatt gcacaaaatc                                              20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 78
aattccctct atttggtggt                                              20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 79
tcccaagcca gtaaagctaa                                              20

<210> SEQ ID NO 80
<211> LENGTH: 20
```

```
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 80
tggtttttca acttcttcca                                              20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 81
tcatagaatg gatggctcaa                                              20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 82
agctactatt gcaccatccc                                              20

<210> SEQ ID NO 83
<211> LENGTH: 22
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 83
caataagggc ataccaaaaa tc                                           22

<210> SEQ ID NO 84
<211> LENGTH: 22
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 84
ccttaacatt tgtggcatta tc                                           22

<210> SEQ ID NO 85
<211> LENGTH: 22
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 85
ttgggaagat gaagttttta ga                                           22

<210> SEQ ID NO 86
<211> LENGTH: 22
<212> TYPE: DNA
<213> ORGANISM: Artificial Sequence
```

```
<220> FEATURE:
<223> OTHER INFORMATION: Description of Artificial Sequence: synthetic
      DNA

<400> SEQUENCE: 86
cctttactcc aataatttgg ct                                              22

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 87
tttcatctat tcaggatggg                                                 20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 88
ggagcaacat tctttgtgac                                                 20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 89
tgtgcctgaa gaaggtattg                                                 20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 90
cgtgttactt caccaccact                                                 20

<210> SEQ ID NO 91
<211> LENGTH: 23
<212> TYPE: DNA
<213> ORGANISM: Staphylococcus aureus

<400> SEQUENCE: 91
tatcttatcg ttgagaaggg att                                             23

<210> SEQ ID NO 92
<211> LENGTH: 22
<212> TYPE: DNA
<213> ORGANISM: Staphylococcus aureus

<400> SEQUENCE: 92
ctacacttgg cttaggatga aa                                              22
```

```
<210> SEQ ID NO 93
<211> LENGTH: 24
<212> TYPE: DNA
<213> ORGANISM: Escherichia coli

<400> SEQUENCE: 93
ctatctgatt gttgaagaag gatt                                          24

<210> SEQ ID NO 94
<211> LENGTH: 24
<212> TYPE: DNA
<213> ORGANISM: Escherichia coli

<400> SEQUENCE: 94
gtttactctt ggtttaggat gaaa                                          24

<210> SEQ ID NO 95
<211> LENGTH: 22
<212> TYPE: DNA
<213> ORGANISM: Staphylococcus aureus

<400> SEQUENCE: 95
cttgttgatc acgataattt cc                                            22

<210> SEQ ID NO 96
<211> LENGTH: 22
<212> TYPE: DNA
<213> ORGANISM: Staphylococcus aureus

<400> SEQUENCE: 96
atcttttagc aaaccgtat tc                                             22

<210> SEQ ID NO 97
<211> LENGTH: 27
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 97
aacaggtgaa ttattagcac ttgtaag                                       27

<210> SEQ ID NO 98
<211> LENGTH: 27
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 98
attgctgtta atattttttg agttgaa                                       27

<210> SEQ ID NO 99
<211> LENGTH: 19
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 99
gtgatcgaaa tccagatcc                                                19
```

```
<210> SEQ ID NO 100
<211> LENGTH: 19
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 100
atcctcggtt ttctggaag                                                19

<210> SEQ ID NO 101
<211> LENGTH: 19
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 101
ctggtcatac atgtgatgg                                                19

<210> SEQ ID NO 102
<211> LENGTH: 19
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 102
gatgttaccc gagagcttg                                                19

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 103
ttaagcgtgc ataataagcc                                               20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 104
ttgcgattac ttcgccaact                                               20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 105
tttactaagc ttgccccttc                                               20

<210> SEQ ID NO 106
<211> LENGTH: 20
```

```
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 106
aaaaggcagc aattatgagc                                                    20

<210> SEQ ID NO 107
<211> LENGTH: 29
<212> TYPE: DNA
<213> ORGANISM: Artificial Sequence
<220> FEATURE:
<223> OTHER INFORMATION: Description of Artificial Sequence: synthetic
      DNA
<220> FEATURE:
<221> NAME/KEY: modified_base
<222> LOCATION: (9)
<223> OTHER INFORMATION: i
<220> FEATURE:
<221> NAME/KEY: modified_base
<222> LOCATION: (12)
<223> OTHER INFORMATION: i
<220> FEATURE:
<221> NAME/KEY: modified_base
<222> LOCATION: (15)
<223> OTHER INFORMATION: i
<220> FEATURE:
<221> NAME/KEY: modified_base
<222> LOCATION: (18)
<223> OTHER INFORMATION: i
<220> FEATURE:
<221> NAME/KEY: modified_base
<222> LOCATION: (21)
<223> OTHER INFORMATION: i

<400> SEQUENCE: 107 aaytgatna cnggngcngc ncaratgga                                           29

<210> SEQ ID NO 108
<211> LENGTH: 23
<212> TYPE: DNA
<213> ORGANISM: Artificial Sequence
<220> FEATURE:
<223> OTHER INFORMATION: Description of Artificial Sequence: synthetic
      DNA
<220> FEATURE:
<221> NAME/KEY: modified_base
<222> LOCATION: (3)
<223> OTHER INFORMATION: i
<220> FEATURE:
<221> NAME/KEY: modified_base
<222> LOCATION: (6)
<223> OTHER INFORMATION: i
<220> FEATURE:
<221> NAME/KEY: modified_base
<222> LOCATION: (9)
<223> OTHER INFORMATION: i
<220> FEATURE:
<221> NAME/KEY: modified_base
<222> LOCATION: (12)
<223> OTHER INFORMATION: i

<400> SEQUENCE: 108
ccnacngtnc knccrccytc rcg                                                23

<210> SEQ ID NO 109
<211> LENGTH: 29
<212> TYPE: DNA
<213> ORGANISM: Artificial Sequence
<220> FEATURE:
<223> OTHER INFORMATION: Description of Artificial Sequence: synthetic
      DNA
```

```
<220> FEATURE:
<221> NAME/KEY: modified_base
<222> LOCATION: (6)
<223> OTHER INFORMATION: i
<220> FEATURE:
<221> NAME/KEY: modified_base
<222> LOCATION: (12)
<223> OTHER INFORMATION: i
<220> FEATURE:
<221> NAME/KEY: modified_base
<222> LOCATION: (15)
<223> OTHER INFORMATION: i
<220> FEATURE:
<221> NAME/KEY: modified_base
<222> LOCATION: (18)
<223> OTHER INFORMATION: i

<400> SEQUENCE: 109
carytnathg tngcngtnaa yaaratgga                                29

<210> SEQ ID NO 110
<211> LENGTH: 831
<212> TYPE: DNA
<213> ORGANISM: Escherichia coli

<400> SEQUENCE: 110
atgaaaaaca caatacatat caacttcgct atttttttaa taattgcaaa tattatctac    60
agcagcgcca gtgcatcaac agatatctct actgttgcat ctccattatt tgaaggaact   120
gaaggttgtt ttttactttta cgatgcatcc acaaacgctg aaattgctca attcaataaa   180
gcaaagtgtg caacgcaaat ggcaccagat tcaactttca agatcgcatt atcacttatg   240
gcatttgatg cggaaataat agatcagaaa accatattca aatgggataa aaccccaaa    300 ggaatggaga tctggaacag caatcataca ccaaagacgt ggatgcaatt ttctgttgtt   360
tgggtttcgc aagaaataac ccaaaaaatt agattaaata aaatcaagaa ttatctcaaa   420
gattttgatt atggaaatca agacttctct ggagataaag aaagaaacaa cggattaaca   480
gaagcatggc tcgaaagtag cttaaaaatt tcaccagaag aacaaattca attcctgcgt   540
aaaattatta tcacaatctc cccagttaaa aactcagcca tagaaaacac catagagaac   600
atgtatctac aagatctgga taatagtaca aaactgtatg ggaaaactgg tgcaggattc   660
acagcaaata gaaccttaca aaacggatgg tttgaagggt ttattataag caaatcagga   720
cataaatatg tttttgtgtc cgcacttaca ggaaacttgg ggtcgaattt aacatcaagc   780
ataaaagcca agaaaaatgc gatcaccatt ctaaacacac taaatttata a            831

<210> SEQ ID NO 111
<211> LENGTH: 846
<212> TYPE: DNA
<213> ORGANISM: Enterococcus faecalis

<400> SEQUENCE: 111
ttgaaaaagt taatatttttt aattgtaatt gctttagttt taagtgcatg taattcaaac    60
agttcacatg ccaaagagtt aaatgattta gaaaaaaaat ataatgctca tattggtgtt   120
tatgctttag atactaaaag tggtaaggaa gtaaaattta ttcagataaa gagatttgcc   180
tatgcttcaa cttcaaaagc gataaatagt gctattttgt tagaacaagt accttataat   240
aagttaaata aaaagtaca tattaacaaa gatgatatag ttgcttattc tcctatttta   300
gaaaaatatg taggaaaaga tatcacttta aaagcactta ttgaggcttc aatgacatat   360
agtgataata cagcaaacaa taaaattata aagaaatcg gtggaatcaa aaagttaaa    420 caacgtctaa aagaactagg agataaagta acaaatccag ttagatatga gatagaatta   480
```

```
aattactatt caccaaagag caaaaaagat acttcaacac ctgctgcttt cggtaagact      540
ttaaataaac ttatcgcaaa tggaaaatta agcaaagaaa acaaaaaatt cttacttgat      600
ttaatgttaa ataataaaag cggagatact ttaattaaag acggtgttcc aaaagactat      660
aaggttgctg ataaaagtgg tcaagcaata acatatgctt ctagaaatga tgttgctttt      720
gtttatccta agggccaatc tgaacctatt gttttagtca ttttttacgaa taaagacaat      780 aaaagtgata agccaaatga taagttgata agtgaaaccg ccaagagtgt aatgaaggaa      840
tttttaa                                                                846

<210> SEQ ID NO 112
<211> LENGTH: 555
<212> TYPE: DNA
<213> ORGANISM: Pseudomonas aeruginosa

<400> SEQUENCE: 112
atgtccgcga gcaccccccc cataactctt cgcctcatga ccgagcgcga cctgccgatg       60
ctccatgact ggctcaaccg gccgcacatc gttgagtggt ggggtggcga cgaagagcga      120
ccgactcttg atgaagtgct ggaacactac ctgcccagag cgatggcgga agagtccgta      180
acaccgtaca tcgcaatgct gggcgaggaa ccgatcggct atgctcagtc gtacgtcgcg      240
ctcggaagcg gtgatggctg gtgggaagat gaaactgatc aggagtgcg aggaatagac       300 cagtctctgg ctgacccgac acagttgaac aaaggcctag aacaaggct tgtccgcgct       360 ctcgttgaac tactgttctc ggaccccacc gtgacgaaga ttcagaccga cccgactccg      420
aacaaccatc gagccatacg ctgctatgag aaggcaggat tcgtgcggga agatcatc       480 accacgcctg acgggccggc ggtttacatg gttcaaacac gacaagcctt cgagagaaag      540
cgcggtgttg cctaa                                                        555

<210> SEQ ID NO 113
<211> LENGTH: 732
<212> TYPE: DNA
<213> ORGANISM: Staphylococcus aureus

<400> SEQUENCE: 113
atgaaccaga aaaaccctaa agacacgcaa aattttatta cttctaaaaa gcatgtaaaa       60
gaaatattga atcacacgaa tatcagtaaa caagacaacg taatagaaat cggatcagga      120
aaaggacatt ttaccaaaga gctagtcaaa atgagtcgat cagttactgc tatagaaatt      180
gatggaggct tatgtcaagt gactaaagaa gcggtaaacc cctctgagaa tataaaagtg      240
attcaaacgg atattctaaa attttccttc ccaaaacata taaactataa gatatatggt      300
aatattcctt ataacatcag tacggatatt gtcaaaagaa ttacctttga agtcaggct       360 aaatatagct atcttatcgt tgagaaggga tttgcgaaaa gattgcaaaa tctgcaacga      420
gctttgggtt tactattaat ggtggagatg atataaaaa tgctcaaaaa agtaccacca       480
ctatattttc atcctaagcc aagtgtagac tctgtattga ttgttcttga acgacatcaa      540
ccattgattt caaagaagga ctacaaaaag tatcgatctt ttgtttataa gtgggtaaac      600
cgtgaatatc gtgttctttt cactaaaaac caattccgac aggctttgaa gcatgcaaat      660
gtcactaata ttaataaact atcgaaggaa caatttcttt ctattttcaa tagttacaaa      720
ttgtttcact aa                                                           732

<210> SEQ ID NO 114
<211> LENGTH: 738
```

<212> TYPE: DNA
<213> ORGANISM: Escherichia coli

<400> SEQUENCE: 114

```
atgaacaaaa atataaaata ttctcaaaac tttttaacga gtgaaaaagt actcaaccaa      60
ataataaaac aattgaattt aaaagaaacc gataccgttt acgaaattgg aacaggtaaa     120
gggcatttaa cgacgaaact ggctaaaata agtaaacagg taacgtctat tgaattagac     180
agtcatctat tcaacttatc gtcagaaaaa ttaaaatcga atactcgtgt cactttaatt     240
caccaagata ttctacagtt tcaattccct aacaaacaga ggtataaaat tgttgggaat     300
attccttacc atttaagcac acaaattatt aaaaaagtgg ttttttgaaag ccatgcgtct     360
gacatctatc tgattgttga agaaggattc tacaagcgta ccttggatat tcaccgaaca     420
ctagggttgc tcttgcacac tcaagtctcg attcagcaat tgcttaagct gccagcggaa     480
tgctttcatc ctaaaccaag agtaaacagt gtcttaataa aacttacccg ccataccaca     540
gatgttccag ataaatattg gaagctatat acgtactttg tttcaaaatg ggtcaatcga     600
gaatatcgtc aactgtttac taaaaatcag tttcatcaag caatgaaaca cgccaaagta     660
aacaatttaa gtaccgttac ttatgagcaa gtattgtcta ttttttaatag ttatctatta     720
tttaacggga ggaaataa                                                   738
```

<210> SEQ ID NO 115
<211> LENGTH: 735
<212> TYPE: DNA
<213> ORGANISM: Staphylococcus aureus

<400> SEQUENCE: 115

```
atgaacgaga aaatataaa acacagtcaa aactttatta cttcaaaaca taatatagat       60
aaaataatga caaatataag attaaatgaa catgataata tctttgaaat cggctcagga     120
aaagggcatt ttaccccttga attagtacag aggtgtaatt tcgtaactgc cattgaaata     180
gaccataaat tatgcaaaac tacagaaaat aaacttgttg atcacgataa tttccaagtt     240
ttaaacaagg atatattgca gtttaaattt cctaaaaacc aatcctataa atatttggt      300
aatatacctt ataacataag tacggatata atacgcaaaa ttgttttttga tagtatagct     360
gatgagattt atttaatcgt ggaatacggg tttgctaaaa gattattaaa tacaaaacgc     420
tcattggcat tatttttaat ggcagaagtt gatatttcta tattaagtat ggttccaaga     480
gaatatttc atcctaaacc tagagtgaat agctcactta tcagattaaa tagaaaaaaa     540
tcaagaatat cacacaaaga taaacagaag tataattatt tcgttatgaa atgggttaac     600
aaagaataca agaaaatatt tacaaaaaat caatttaaca attccttaaa acatgcagga     660
attgacgatt taaacaatat tagctttgaa caattcttat ctcttttcaa tagctataaa     720
ttatttaata agtaa                                                      735
```

<210> SEQ ID NO 116
<211> LENGTH: 1029
<212> TYPE: DNA
<213> ORGANISM: Enterococcus faecalis

<400> SEQUENCE: 116

```
atgaataaaa taaagtcgc aattatcttc ggcggttgct cggaggaaca tgatgtgtcg       60
gtaaaatccg caatagaaat tgctgcgaac attaatactg aaaaattcga tccgcactac     120
atcggaatta caaaaacgg cgtatggaag ctatgcaaga agccatgtac ggaatgggaa     180
gccgatagtc tccccgccat attctccccg gataggaaaa cgcatggtct gcttgtcatg     240
```

```
aaagaaagag aatacgaaac tcggcgtatt gacgtggctt tcccggtttt gcatggcaaa      300
tgcggggagg atggtgcgat acagggtctg tttgaattgt ctggtatccc ctatgtaggc      360
tgcgatattc aaagctccgc agcttgcatg gacaaatcac tggcctacat tcttacaaaa      420
aatgcgggca tcgccgtccc cgaatttcaa atgattgaaa aaggtgacaa accggaggcg      480
aggacgctta cctaccctgt ctttgtgaag ccggcacggt caggttcgtc ctttggcgta      540
accaaagtaa acagtacgga agaactaaac gctgcgatag aagcagcagg acaatatgat      600
ggaaaaatct taattgagca agcgatttcg ggctgtgagg tcggctgcgc ggtcatggga      660
aacgaggatg atttgattgt cggcgaagtg gatcaaatcc ggttgagcca cggtatcttc      720
cgcatccatc aggaaaacga gccggaaaaa ggctcagaga atgcgatgat tatcgttcca      780
gcagacattc cggtcgagga acgaaatcgg gtgcaagaaa cggcaaagaa agtatatcgg      840
gtgcttggat gcagagggct tgctcgtgtt gatcttttt tgcaggagga tggcggcatc      900
gttctaaacg aggtcaatac cctgcccggt tttacatcgt acagccgcta tccacgcatg      960
gcggctgccg caggaatcac gcttcccgca ctaattgaca gcctgattac attggcgata     1020
gagaggtga                                                             1029

<210> SEQ ID NO 117
<211> LENGTH: 1031
<212> TYPE: DNA
<213> ORGANISM: Enterococcus gallinarum

<400> SEQUENCE: 117
atgaaaaaaa ttgccgttt atttggaggg aattctccag aatactcagt gtcactaacc       60
tcagcagcaa gtgtgatcca agctattgac ccgctgaaat atgaagtaat gaccattggc      120
atcgcaccaa caatggattg gtattggtat caaggaaacc tcgcgaatgt tcgcaatgat      180
acttggctag aagatcacaa aaactgtcac cagctgactt tttctagcca aggatttata      240
ttaggagaaa aacgaatcgt ccctgatgtc ctctttccag tcttgcatgg aagtatggc       300 gaggatggct gtatccaagg actgcttgaa ctaatgaacc tgccttatgt tggttgccat      360
gtcgctgcct ccgcattatg tatgaacaaa tggctcttgc atcaacttgc tgataccatg      420
ggaatcgcta gtgctcccac tttgcttta tcccgctatg aaaacgatcc tgccacaatc       480
gatcgtttta ttcaagacca tggattcccg atctttatca agccgaatga agccggttct      540
tcaaaaggga tcacaaaagt aactgacaaa acagcgctcc aatctgcatt aacgactgct      600
tttgcttacg gttctactgt gttgatccaa aaggcgatag cgggtattga aattggctgc      660
ggcatcttag gaaatgagca attgacgatt ggtgcttgtg atgcgatttc tcttgtcgac      720 ggttttttg attttgaaga gaaataccaa ttaatcagcg ccacgatcac tgtcccagca      780
ccattgcctc tcgcgcttga atcacagatc aaggagcagg cacagctgct ttatcgaaac      840
ttgggattga cgggtctggc tcgaatcgat tttttcgtca ccaatcaagg agcgatttat      900
ttaaacgaaa tcaacaccat gccgggattt actgggcact cccgctaccc agctatgatg      960
gcggaagtcg ggttatccta cgaaatatta gtagagcaat tgattgcact ggcagaggag     1020
gacaaacgat g                                                          1031

<210> SEQ ID NO 118
<211> LENGTH: 809
<212> TYPE: DNA
<213> ORGANISM: Abiotrophia adiacens

<400> SEQUENCE: 118
```

```
tggtgctatc ttagtagtat ctgcagctga tggtccaatg cctcaaacac gtgaacacat    60
cttattatca cgtcaagtag gtgttcctta catcgttgta ttcttaaaca aagttgacat   120
ggttgacgat gaagaattat tagaattagt agaaatggaa gttcgtgact tattatcaga   180
atacgatttc ccaggcgatg acactccagt tgttgcaggt tctgctttac gcgctttaga   240
aggcgacgct tcatacraag aaaaaatctt agaattaatg gctgctgttg acgaatacat   300
tccaactcca gaacgygacg ttgacaaacc attcatgatg ccagttgaag acgtgttctc   360
aatcacaggt cgtggtactg ttgctacagg tcgtgttgaa cgtggacaag ttcgtgttgg   420
tgacgaagtt gaaatcgttg gtatttcaga agaaacttca aaaacaactg taactggtgt   480
tgaaatgttc cgtaaattgt tagactacgc tgaagcaggg gataacattg gtacattatt   540
acgtggtgtt acacgtgaca acatcgaacg tggacaagtt cttgctaaac caggaacaat   600
cactccacat actaaattca aagctgaagt ttacgtatta actaaagaag aaggtggacg   660
tcatactcca ttcttctcta actaccgtcc tcaattctac ttccgtacaa cagacatcac   720
tggtgtttgt gtgttaccag aaggcgttga aatggtaatg cctggtgata acgtaactat   780
ggaagttgaa ttaattcacc cagtagcga                                     809

<210> SEQ ID NO 119
<211> LENGTH: 817
<212> TYPE: DNA
<213> ORGANISM: Abiotrophia defectiva

<400> SEQUENCE: 119
cggcgcgatc ctcgttgtat ctgctgctga cggcccaatg ccacaaactc gtgaacacat    60
cctcttgtct cgtcaagttg gtgttcctta catcgtagta ttcttgaaca aagttgacat   120
ggttgacgac gaagaattgc tcgaattagt tgaaatggaa gttcgtgacc tcttgtctga   180
atacgacttc ccaggcgacg acactccagt tatcgctggt tcagctttga agctttaga   240 aggcgacgct aactacgaag ctaaagtttt agaattgatg gaacaagttg atgcttacat   300
tccagaacca gaacgtgaca ctgacaagcc attcatgatg ccagtcgaag acgtattctc   360
tatcactggt cgtggtactg ttgcaactgg tcgtgttgaa cgtggtcaag ttcgcgttgg   420
tgacgaagtt gaaatcgttg gtatcgaaga agaaacttct aagactaccg ttaccggtgt   480
tgaaatgttc cgtaagttat tggattacgc tgaagctggg gacaacgttg gtaccttgtt   540
acgtggtgta actcgtgacc aaatccaacg tggtcaagta ttatctaaac caggttcaat   600
cactccgyac actaagttcg aagctgaagt gtacgtattg tctaaagaag aaggtggtcg   660
tcacactcca ttcttctcta actaccgtcc acaattctac ttccgtacaa ctgacgtaac   720
tggtgttgtt actttaccag aaggtactga atggttatg ccaggcgaca acgtacaaat   780
ggttgttgaa ttgatccacc caatcgcgat cgaagaa                            817

<210> SEQ ID NO 120
<211> LENGTH: 754
<212> TYPE: DNA
<213> ORGANISM: Candida albicans

<400> SEQUENCE: 120
ctctgtcaaa tgggacaaaa acagatttga agaaatcatc aaggaaacct ccaacttcgt    60
caagaaggtt ggttacaacc caaagactgt tccattcgtt ccaatctctg gttggaatgg   120
tgacaacwtg attgaascat ccaccaactg tccatggtac aagggttggg aaaaggaaac   180
caaatccggt aaagttactg gtaagacctt gttagaagct attgacgcta ttgaaccacc   240
```

```
aaccagacca accgacaaac cattgagatt gccattrcaa gatgtttaca agatcggtgg    300
tattggtact gtgccagtcg gtagagttga aactggtatc atcaaagccg gtatggtwgt    360
tactttcgcc ccagctggtg ttaccactga agtcaartcc gttgaaatgc atcacgaaca    420
attggctgaa ggtgttccag gtgacaatgt trgtttcaac gttaagaacr tttccgttaa    480
agaaattaga gaggtaacg tttgtggtga ctccaagaac gatccaccaa agggttgtga    540
ctctttcaat gcccaagtca ttgttttgaa ccatccaggt caaatctctg ctggttactc    600
tccagtcttg gattgtcacr ctgcccacat tgcttgtaaa ttcgacrctt tggttgaaaa    660
gattgacaga agaactggta agraattgga agaaaatcca aaattcgtca aatccggtga    720
tgctgctatc gtcaagatgg tcccaaccaa acca                                754
```

<210> SEQ ID NO 121  
<211> LENGTH: 753  
<212> TYPE: DNA  
<213> ORGANISM: Candida glabrata

<400> SEQUENCE: 121

```
tctgtcaagt gggatgaatc cagattcgct gaaatcgtta aggaaacctc caacttcatc     60
aagaaggtcg gttacaaccc aaagactgtt ccattcgtcc aatctctgg ttggaacggt     120 gacaacatga ttgaagccac caccaacgct tcctggtaca agggttggga aaaggaaacc    180
aaggctggtg tcgtcaaggg taagaccttg ttggaagcca ttgacgctat cgaaccacca    240
accagaccaa ctgacaagcc attgagattg ccattgcaag atgtctacaa gatcggtggt    300
atcggtacgg tgccagtcgg tagagtcgaa accggtgtca tcaagccagg tatggttgtt    360
accttcgccc cagctggtgt taccactgaa gtcaagtccg ttgaaatgca ccacgaacaa    420
ttgactgaag gtttgccagg tgacaacgtt ggtttcaacg ttaagaacgt ttccgttaag    480
gaaatcagaa gaggtaatgt ctgtggtgac tccaagaacg acccaccaaa ggctgctgct    540
tctttcaacg ctaccgtcat tgtcttgaac cacccaggtc aaatctctgc tggttactct    600
ccagttttgg actgtcacac cgcccacatt gcttgtaagt tcgaagaatt gttggaaaag    660
aacgacagaa gatccggtaa gaagttggaa gactctccaa agttcttgaa gtccggtgac    720
gctgctttgg ttaagttcgt tccatccaag cca                                 753
```

<210> SEQ ID NO 122  
<211> LENGTH: 752  
<212> TYPE: DNA  
<213> ORGANISM: Candida kruisii

<400> SEQUENCE: 122

```
ccgttaagtg ggatgaaaac agatttgaag aaattgtcaa ggaaacccaa aacttcatca     60
agaaggttgg ttacaaccca agactgttc cattcgttcc aatctctggt tggaatggtg    120
acaacatgat tgaagcatcc accaactgtc catggtacaa gggttggact aaggaaacca    180
aggcaggtgt tgttaagggt aagaccttat tagaagcaat cgatgctatt gaaccacctg    240
tcagaccaac cgaaaagcca ttaagattac cattacaaga tgtttacaag attggtggta    300
ttggtactgt gccagtcggt agagtcgaaa ccggtgtcat taagccaggt atggttgtca    360
cttttgctcc agcaggtgtc accaccgaag tcaaatccgt tgaaatgcac catgaacaat    420
tagaacaagg tgttccaggt gataacgttg gtttcaacgt taagaacgty tctgtcaagg    480
atatcaagag aggtaacgtt tgtggtgact ccaagaacga cccaccaatg ggtgcagctt    540 cttttcaatgc tcaagtcatt gtcttgaacc accctggtca aatttccgct ggttactctc    600
```

```
cagtcttgga ttgtcacact gcccacattg catgtaagtt cgacgaatta atcgaaaaga    660
ttgacagaag aactggtaag tctgttgaag accatccaaa gtcygtcaag tctggtgatg    720
cagctatcgt caagatggtc ccaaccaagc ca                                  752
```

<210> SEQ ID NO 123
<211> LENGTH: 754
<212> TYPE: DNA
<213> ORGANISM: Candida parapsilosis

<400> SEQUENCE: 123

```
ctcagtcaaa tgggacaaga rcagatacga agaaattgtc aaggaaactt ccaacttcgt    60
caagaaggtt ggttacaacc ctaaagctgt cccattcgtc ccaatctctg gttggaacgg   120
tgacaatatg attgaaccat caaccaactg tccatggtac aagggttggg aaaaggaaac   180
taaagctggt aaggttaccg gtaagacctt gttggaagct atcgatgcta tcgarccacc   240
aaccagacca actgacaagc cattgagatt gccattgcaa gatgtctaca agattggtgg   300
tattggaact gtgccagttg gtagagttga aaccggtatc atcaaggctg gtatggttgt   360
tacttttgcc ccagctggtg ttaccactga agtcaagtcc gttgaaatgc accacgaaca   420
attgactgaa ggtgtcccag gtgacaatgt tggtttcaac gtcaagaacg tttcagttaa   480
ggaaatcaga gaggtaacg ytgtggtga ctccaagaac gatccaccaa agggatgtga   540
ytccttcaat gctcaagtta ttgtcttgaa ccacccaggt caaatctctg ctggttactc   600
accagtcttg gattgtcaca ctgcccacat tgcttgtaaa ttcgacactt tgattgaaaa   660
gattgacaga gaaccggta agaaattgga agwtgaacca aaattcatca gtccggtga   720 tgctgcyatc gtcaagatgg tcccaaccaa gcca                                754
```

<210> SEQ ID NO 124
<211> LENGTH: 753
<212> TYPE: DNA
<213> ORGANISM: Candida tropicalis

<400> SEQUENCE: 124

```
tctgttaaat gggacaaraa cagatttgaa gaaattatca aggaaacytc taacttcgtc    60
aagaaggttg gttacaaccc taaggctgtt ccattcgttc caatctcwgg ttggaatggt   120
gacaacatga ttgaagcttc taccaactgt ccatggtaca agggttggga aaagaaacc   180 aaggctggta aggttaccgg taagactttg ttggaagcca ttgatgctat tgaaccacct   240
tcaagaccaa ctgacaagcc attgagattg ccattgcaag atgtttacaa gattggtggt   300
attggtactg tgccagtcgg tagagttgaa actggtgtca tcaaagccgg tatggttgtt   360
actttygccc cagctggtgt taccactgaa gtcaaatccg tygaaatgca ccacgaacaa   420
ttggctgaag gtgtcccagg tgacaatgtt ggtttcaacg ttaagaacgt ttctgttaaa   480
gaaattagaa gaggtaacgt tgtggtgac tccaagaacg atccaccaaa gggttgtgac   540
tctttcaacg ctcaagttat tgtcttgaac cacccaggtc aaatytctgc tggttactct   600
ccagtcttgg attgtcacac tgctcatatt gcttgtaaat tcgacacctt ggttgaaaag   660
attgacagaa gaactggtaa gaaattggaa gaaaatccaa aattcgtcaa atccggtgat   720
gctgctattg tcaagatggt tccaaccaaa cca                                 753
```

<210> SEQ ID NO 125
<211> LENGTH: 814
<212> TYPE: DNA
<213> ORGANISM: Corynebacterium accolens

<400> SEQUENCE: 125
cggcgctatc ctggttgttg ctgcaaccga tggcccgatg ccgcagaccc gcgagcacgt 60
tctgcttgct cgccaggttg gcgttcctta catcctcgtt gcactgaaca agtgcgacat 120
ggttgatgat gaggaaatca tcgagctcgt ggagatggag atctccgagc tgctcgcaga 180
gcaggactac gatgaggaag ctcctatcgt tcacatctcc gctctgaagg cactcgaggg 240
tgacgagaag tgggtacagt ccatcgttga cctgatggat gcctgcgaca actccatccc 300
tgatccggag cgcgctaccg atcagccgtt cttgatgcct atcgaggaca tcttcaccat 360
taccggccgc ggtaccgttg ttaccggccg tgttgagcgt ggtcgtctga acgtcaacga 420
ggacgttgag atcatcggta tccaggagaa gtcccagaac accaccgtta ccggtatcga 480
gatgttccgc aagatgatgg actacaccga ggctggcgac aactgtggtc tgcttctgcg 540
tggtaccaag cgtgaggacg ttgagcgtgg ccaggttgtt atcaagccgg gcgcttacac 600
ccctcacacc aagttcgagg gttccgtcta cgtcctgaag aaggaagagg gcggccgcca 660
caccccgytc atgaacaact accgtcctca gttctacttc cgcaccaccg acgttaccgg 720
tgttgtgaac ctgcctgagg gcaccgagat ggttatgcct ggcgacaacg ttgagatgtc 780
tgttgagctc atccagcctg ttgctatgga cgag 814

<210> SEQ ID NO 126
<211> LENGTH: 814
<212> TYPE: DNA
<213> ORGANISM: Corynebacterium diphtheriae

<400> SEQUENCE: 126
cggcgcaatc ctcgttgttg ctgccaccga cggcccaatg cctcagaccc gtgagcacgt 60
tctgctcgct cgccaggtcg gcgttcctta catcctcgtt gctctgaaca agtgcgacat 120
ggttgatgat gaggaaatca tcgagctcgt cgagatggag atccrtgagc tgctcgctga 180
gcaggattac gacgaagagg ctccaatcat ccacatctcc gcactgaagg ctcttgaggg 240
cgacgagaag tggacccagt ccatcatcga cctcatgcag gcttgckatg attccatccc 300
agacccagag cgtgagaccg acaagccatt cctcatgcct atcgaggaca tcttcaccat 360
caccggccgc ggtaccgttg ttaccggccg tgttgagcgt ggctccctga aggtcaacga 420
ggacgtcgag atcatcggta tccgcgagaa kgctaccacc accaccgtta ccggtatcga 480
gatgttccgt aagcttctcg actacaccga ggctggcgac aactgtggtc tgcttctccg 540
tggcgttaag cgcgaagacg ttgagcgtgg ccaggttgtt gttaagccag gcgcttacac 600
ccctcacacc gagttcgagg gctctgtcta cgttctgtcc aaggacgagg gtggccgcca 660
caccccattc ttcgacaact accgcccaca gttctacttc cgcaccaccg acgttaccgg 720
tgttgtgaag cttcctgagg gcaccgagat ggtcatgcct ggcgacaacg tcgacatgtc 780
cgtcaccctg atccagcctg tcgctatgga tgag 814

<210> SEQ ID NO 127
<211> LENGTH: 814
<212> TYPE: DNA
<213> ORGANISM: Corynebacterium genitalium

<400> SEQUENCE: 127
cggcgccatc ctggttgttg ctgcaaccga tggcccgatg ccgcagaccc gtgagcacgt 60
tctgctggct cgccaggttg gcgttccgta catcctagtt gcactgaaca agtgcgacat 120
ggttgatgat gaggagctgc tggagctcgt cgagatggag gtccgcgagc tgctggctga 180

```
gcaggacttc gacgaggaag cacctgttgt tcacatctcc gcactgaagg ccctggaggg    240
cgacgagaag tgggctaagc agatcctgga gctcatggag gcttgcgaca actccatccc    300
ggatccggag cgcgagaccg acaagccgtt cctgatgccg gttgrggaca tcttcaccat    360
taccggccgc ggtaccgttg ttaccggccg tgttgagcgt ggcgtcctga acctgaacga    420
cgaggtcgag atcctgggca tccgcgagaa gtccaccaag accaccgtta cctccatcga    480
gatgttcaac aagctgctgg acaccgcaga ggctggcgac aacgccgcac tgctgctgcg    540
tggcctgaag cgcgaagatg ttgagcgtgg tcagatcgtt gctaagccgg gcagtacac     600 cccgcacacc gagttcgagg ctccgtcta cgttctgtcc aaggacgagg gtggccgcca    660
caccccgttc ttcgacaact accgtccgca gttctatttc cgcaccaccg acgttaccgg    720
tgttgtgaag ctgccggagg gcaccgagat ggttatgccg ggcgacaacg ttgacatgtc    780
cgtcaccctg atccagccgg ttgctatgga cgag                                814

<210> SEQ ID NO 128
<211> LENGTH: 814
<212> TYPE: DNA
<213> ORGANISM: Corynebacterium jeikeium

<400> SEQUENCE: 128
cggcgccatc ctggttgttg ccgcaaccga tggcccgatg ccgcagaccc gcagcacgt      60 tctgctggcy cgccaggttg gcgttccgta catcctggtt gcactgaaca agtgtgacat    120
ggttgacgat gaggagctgc tggagctcgt cgagatggag gtccgcgagc tgctggctga    180
gcaggacttc gacgaggaag ctccggttgt tcacatctcc gcactgaagg ccctggaggg    240
cgacgagaag tgggctaacc agattctcga gctgatgcag gcttgcgacg agtctatccc    300
ggatccggag cgcgagaccg acaagccgtt cctgatgccg gttgwggaca tcttcaccat    360
taccggtcgc ggtaccgttg ttaccggccg tgttgagcgt ggcatcctga acctgaacga    420
cgaggttgag atcctgggta tccgcgagaa gtcccagaag accaccgtta cctccatcga    480
gatgttcaac aagctgctgg acaccgcaga ggctggcrac aacgctgcac tgctgctgcg    540
tggtctgaag cgcgaggacg ttgagcgtgg ccagatcatc gctaagccgg gcgagtacac    600
cccgcacacc gagttcgagg ctccgtcta cgttctgtcc aaggacgagg gcggccgcca    660
caccccgttc ttcgacaact accgtccgca gttctacttc cgcaccaccg acgttaccgg    720
tgttgtgaag ctgcctgagg gcaccgagat ggttatgccg ggcgacaacg tygacatgtc    780
cgtcaccctg atccagccgg ttgctatgga cgag                                814

<210> SEQ ID NO 129
<211> LENGTH: 748
<212> TYPE: DNA
<213> ORGANISM: Corynebacterium pseudodiphtheriticum

<400> SEQUENCE: 129
cggcgctatc ttggttgttg cagctaccga cggcccaatg ccacagactc gcagcacgt      60 tctgctggct cgccaggttg gcgttcctta catcctggtt gcactaaaca agtgcgacat    120
ggttgacgac gaggaaatcc tcgagctcgt cgagatggag atccgcgaat gctggctga    180 ccaggaattc gacgaagaag ctccaatcgt tcacatctcc gcagtcggcg ccttggaagg    240
cgaagagagg tgggttaacg ccatcgttga actgatggat gcttgtgacg agtcgatccc    300
tgatccagac cgtgctaccg acaagccatt cctgatgcct atcggaggaca tcttcaccat    360 taccggtcgt ggcaccgttg ttacgggtcg tgttgagcgt ggttccctga aggtcaacga    420
```

-continued

| | |
|---|---|
| agaagtcgag atcatcggca tcaaggaaaa gtcccagaag accaccatca ccggtatcga | 480 |
| aatgttccgc aagatgctgg actacaccga ggccggcgac aacgctggtc tgctgcttcg | 540 |
| cggtaccaag cgtgaagacg ttgagcgtgg acaggttatc gttgctccag gtgcttacag | 600 |
| cacccacaag aagttcgaag gttccgtcta cgttctttcc aaggacgagg cggccgcca | 660 |
| caccccgttc ttcgacaact accgtcctca gttctacttc cgcaccaccg acgttaccgg | 720 |
| tgttgttacc ctgcctgagg gcaccgag | 748 |

<210> SEQ ID NO 130
<211> LENGTH: 813
<212> TYPE: DNA
<213> ORGANISM: Corynebacterium striatum

<400> SEQUENCE: 130

| | |
|---|---|
| ggcgctatct tggttgttgc tgcaaccgat ggcccgrtgc cgcagacccg cgagcacgtt | 60 |
| cttctggctc gccaggttgg cgttccttac atcctcgttg cactgaacaa gtgcgacatg | 120 |
| gttgacgacg aggaaattat cgagctcgtc gagatggaga tccgcgaact gctcgcagag | 180 |
| caggactacg atgaggaagc tccgatcgtt cacatctctg ctctgaaggc tcttgagggc | 240 |
| grcgagaagt gggtacaggc tatcgttgac ctgatgcagg cttgcgatga ctccatcccg | 300 |
| gatccggagc gcgagctgga caagccgttc ctgatgccaa tcgaggacat cttcaccatc | 360 |
| accggccgcg gtaccgttgt tactggccgt gttgagcgtg gctccctgaa cgtcaacgag | 420 |
| gacgttgaga tcatcggtat ccaggacarg tccatctcca ccaccgttac cggtatcgag | 480 |
| atgytccgca agatgatgga ctacaccgag gctggcgaca actgtggtct gcttctgcgt | 540 |
| ggtaccaagc gtgaagaggt tgagcgcggc caggttgtta ttaagccggg cgcttacacc | 600 |
| cctcacaccc agttcgaggg ttccgtctac gtcctgaaga aggaagaggg cggccgccac | 660 |
| accccgttca tggacaacta ccgtccgcag ttctacttcc gcaccaccga cgttaccggc | 720 |
| gtcatcaagc tgcctgaggg caccgagatg gttatgcctg gcgacaacgt cgagatgtcy | 780 |
| gtcgagctga tccagccggt cgctatggac gag | 813 |

<210> SEQ ID NO 131
<211> LENGTH: 817
<212> TYPE: DNA
<213> ORGANISM: Enterococcus avium

<400> SEQUENCE: 131

| | |
|---|---|
| cggagctatc ttagtagtat ctgctgctga tggccctatg cctcaaactc gtgaacacat | 60 |
| cttgttatct cgtaacgttg gtgttcctta catcgttgta ttcttaaaca aaatggatat | 120 |
| ggttgacgat gaagaattac ttgaattagt tgaaatggaa gttcgtgact tattaactga | 180 |
| atacgacttc ccaggcgacg acactccagt tatcgcaggt tcagcgttga agctttaga | 240 |
| aggcgacgct tcatacgaag aaaaaatctt agaattaatg gctgctgttg acgaatatat | 300 |
| cccaacacca gttcgtgata ctgacaaacc attcatgatg ccagtcgaag acgtattctc | 360 |
| aatcactggt cgtggtactg ttgcaactgg tcgtgttgaa cgtggacaag ttcgcgttgg | 420 |
| tgacgaagtt gaaatcgtag gtatcgctga cgaaactgct aaaacaactg ttacaggtgt | 480 |
| tgaaatgttc cgtaaattgt tagactacgc tgaagcaggg gacaacatcg gtgctttgtt | 540 |
| acgtggtgtt gcacgtgaag atatccaacg tggacaagta ttggctaaac cagcttcaat | 600 |
| cactccacat acaaaattct ctgcagaagt ttatgttcta actaaagaag aaggtggacg | 660 |
| tcatactcca ttcttcacta actaccgtcc tcagttctac ttccgtacaa ctgacgtaac | 720 |

```
tggtgtagtt gatctaccag aaggtactga aatggtwatg cctggggata acgtaactat    780
ggaagttgaa ttgatycacc caatygcggt agaagac                             817
```

<210> SEQ ID NO 132
<211> LENGTH: 817
<212> TYPE: DNA
<213> ORGANISM: Enterococcus faecalis

<400> SEQUENCE: 132

```
cggagctatc ttagtagttt ctgctgctga tggtcctatg cctcaaacac gtgaacatat     60
cttattatca cgtaacgttg gtgtaccata catcgttgta ttcttaaaca aaatggatat    120
ggttgatgac gaagaattat tagaattagt agaaatggaa gttcgtgact tattatcaga    180
atacgatttc ccaggcgatg atgttccagt tatcgcaggt tctgctttga aagctttaga    240
aggcgacgag tcttatgaag aaaaaatctt agaattaatg gctgcagttg acgaatatat    300
cccaactcca gaacgtgata ctgacaaacc attcatgatg ccagtcgaag acgtattctc    360
aatcactgga cgtggtactg ttgctacagg acgtgttgaa cgtggtgaag ttcgcgttgg    420
tgacgaagtt gaaatcgttg gtattaaaga cgaaacatct aaaacaacyg ttacaggtgt    480
tgaaatgttc cgtaaattat tagactacgc tgaagcaggc gacaacmtcg gtgctttatt    540
acgtggtgta gcacgtgaag atatcgaacg tggacaagta ttagctaaac cagctacaat    600
cactccacac acaaaattca aagctgaagt atacgtatta tcaaaagaag aaggcggacg    660
tcacactcca ttcttcacta actaccgtcc tcaattctac ttccgtacaa cagacgttac    720
tggtgttgta gaattgccag aaggtactga aatggtaatg cctggtgata acgttgctat    780
ggacgttgaa ttaattcacc caatcgctat cgaagac                             817
```

<210> SEQ ID NO 133
<211> LENGTH: 774
<212> TYPE: DNA
<213> ORGANISM: Enterococcus faecium

<400> SEQUENCE: 133

```
cggagctatc ttggtagttt ctgctgctga cggcccaatg cctcaaactc gtgaacacat     60
cctattgtct cgtcaagttg gtgttcctta catcgttgta ttcttgaaca aagtagacat    120
ggttgatgac gaagaattac tagaattagt tgaaatggaa gttcgtgacc tattaacaga    180
atacraattc cctggtgrcg atgttcctgt agttgctgga tcagctttga aagctctaga    240
aggcgacgct tcatacgaag aaaaaattct tgaattaatg gctgcagttg acgaatacat    300
cccaactcca gaacgtgaca cgacaaaacc attcatgatg ccagttgaag acgtgttctc    360
aattactgga cgtggtactg ttgctacagg tcgtgttgaa cgtggacaag ttcgcgttgg    420
tgacgaagtt gaagttgttg gtattgctga agaaacttca aaaacaacag ttactggtgt    480
tgaaatgttc cgtaaattgt tagacyacgc tgaagctgga gacracattg gtgctttact    540
acgtggtgtt gcacgtgaag acatccaacg tggacaagtt ttagctaaac caggtacaat    600
cacacctcrt acaaaattct ctgcagaagt atacgtgttg acaaaagaag aaggtggacg    660
tcatactcca ttcttcacta actaccgtcc acaattctac ttccgtacaa ctgacgtaac    720
aggtgttgtt gaattaccag aaggaactga aatggtcatg cccggtgaca acgt          774
```

<210> SEQ ID NO 134
<211> LENGTH: 809
<212> TYPE: DNA
<213> ORGANISM: Enterococcus gallinarum

<400> SEQUENCE: 134

```
cggtgcgatc ttagtagtat ctgctgctga cggtcctatg cctcaaactc gtgaacacat    60
cttgttatca cgtaacgttg gcgtaccata catcgttgtt ttcttgaaca aaatggatat   120
ggttgaygac gaagaattgc tagaattagt tgaaatggaa gttcgtgacc tattgtctga   180
atatgacttc ccaggcgacg atgttcctgt aatcgccggt tctgctttga agctcttga    240
aggagatcct tcatacgaag aaaaaatcat ggaattgatg gctgcagttg acgaatacgt   300
tccaactcca gaacgtgata ctgacaaacc attcatgatg ccagtcgaag acgtattctc   360
aatcactgga cgtggtactg ttgctacagg ccgtgttgaa cgtggacaag ttcgcgttgg   420
tgatgaagta gaaatcgttg gtattgctga cgaaactgct aaaacaactg taacaggtgt   480
tgaaatgttc cgtaaattgt tagactatgc tgaagcaggg gataacattg gtgcattgct   540
acgtgggggtt gctcgtgaag acatccaacg tggacaagta ttggctaaag ctggtacaat   600
cacacctcat acaaaattca agctgaagt ttatgttttg acaaagaag aaggtggacg    660
tcacactcca ttcttcacta actaccgtcc tcagttctac ttccgtacaa ctgacgtaac   720
tggtgttgtt gaattaccag aaggaactga atggtgatg cctggcgaca acgtgaccat   780
cgacgttgaa ttgatrcacc caatcgctc                                    809
```

<210> SEQ ID NO 135
<211> LENGTH: 823
<212> TYPE: DNA
<213> ORGANISM: Gardnerella vaginalis

<400> SEQUENCE: 135

```
tggcgcaatc ctcgtggttg ctgctaccga cggtccaatg gctcagaccc gtgaacacgt    60
cttgcttgct aagcaggtcg gcgttccaaa aattcttgtt gctttgaaca agtgcgatat   120
ggttgacgac gaagagctta tcgatctcgt tgaagaagag gtccgtgacc tcctcgaaga   180
aaacggcttc gatcgcgatt gcccagtcyt ccgtacttcc gcttacggcg ctttgcatga   240
tgacgctcca gaccacgaca gtgggtaga ccgtcaag gaactcatga aggctgttga     300
cgagtacatc ccaacccca ctcacgatct tgacaagcca ttcttgatgc caatcgaaga    360
tgtgttcacc atctccggtc gtggtyccgt tgtcaccggt cgtgttgagc gtggtaagct   420
cccaatcaac accccagttg agatcgttgg tttgcgcgat acccagacca ccaccgtcac   480
ctctatcgag accttccaca agcagatgga tgaggcagag gctggcgata acactggtct   540
tcttctccgc ggtatcaacc gtaccgacgt tgagcgtggt caggttgtgg ctgctccagg   600
ttctgtgact ccacacacca gttcgaaagg cgaagtttac gtcttgacca aggacgaagg   660
tggccgtcac tcgccattct tctccaacta ccgtccacag ttctacttcc gtaccaccga   720
tgttactggc gttatcacct tgccagacgg catcgaaatg gttcagccag gcgatcacgc   780
aaccttcact gttgagttga tccaggctat cgcaatggaa gag                    823
```

<210> SEQ ID NO 136
<211> LENGTH: 817
<212> TYPE: DNA
<213> ORGANISM: Listeria innocua

<400> SEQUENCE: 136

```
cggagctatc ttagtagtat ctgctgctga tggcccaatg ccacaaactc gtgaacatat    60
cttactttca cgtcaagttg gtgttccata catcgttgta ttcatgaaca aatgtgacat   120
ggttgacgat gaagaattac tagaattagt tgaaatggaa attcgtgatc tattaactga   180
```

| | |
|---|---|
| atatgaattc cctggcgatg acattcctgt aatcaaaggt tcagctctta aagcacttca | 240 |
| aggtgaagct gactgggaag ctaaaattga cgagttaatg gaagctgtag attcttacat | 300 |
| tccaactcca gaacgtgata ctgacaaacc attcatgatg ccagttgagg atgtattctc | 360 |
| aatcactggt cgtggaacag ttgcaactgg acgtgttgaa cgtggacaag ttaaagttgg | 420 |
| tgacgaagta gaagttatcg gtattgaaga agaaagcaaa aaagtagtag taactggagt | 480 |
| agaaatgttc cgtaaattac tagactacgc tgaagctggc gacaacattg gcgcacttct | 540 |
| acgtggtgtt gctcgtgaag atatccaacg tggtcaagta ttagctaaac caggttcgat | 600 |
| tactccacac actaacttca aagctgaaac ttatgtttta actaaagaag aaggtggacg | 660 |
| tcacactcca ttcttcaaca actaccgccc acaattctat ttccgtacta ctgacgtaac | 720 |
| tggtattgtt acacttccag aaggtactga atggtaatg cctggtgata acattgagct | 780 |
| tgcagttgaa ctaattgcac caatcgctat cgaagac | 817 |

<210> SEQ ID NO 137
<211> LENGTH: 818
<212> TYPE: DNA
<213> ORGANISM: Listeria ivanovii

<400> SEQUENCE: 137

| | |
|---|---|
| cggagctatc ttagtagtat ctgctgctga tggtccaatg ccacaaactc gtgaacatat | 60 |
| tcttactttc acgtcaagtt ggtgttccat acatcgttgt attcatgaac aaatgtgaca | 120 |
| tggttgacga tgaagaatta cttgaattag ttgaaatgga aattcgtgat ctattaactg | 180 |
| aatatgaatt ccctggcgac gacattcctg taatcaaagg ttcagctctt aaagcacttc | 240 |
| aaggtgaagc tgattgggaa gctaaaattg acgagttaat ggaagctgta gattcttaca | 300 |
| ttccaactcc agaacgtgat actgacaaac cattcatgat gccagttgag gatgtattct | 360 |
| caatcactgg tcgtggaaca gttgcaactg gacgtgttga acgtggacaa gttaaagttg | 420 |
| gtgacgaagt agaagttatc ggtattgaag aagaaagcaa aaaagtagta gtaactggag | 480 |
| tagaaatgtt ccgtaaatta ctagactacg ctgaagctgg cgacaacatt ggcgcacttc | 540 |
| tacgtggtgt tgctcgtgaa gatatccaac gtggtcaagt attagctaaa ccaggttcga | 600 |
| ttactccaca cactaacttc aaagctgaaa cttatgtttt aactaaagaa gaaggtggac | 660 |
| gtcatactcc attcttcaac aactaccgcc acaattcta tttccgtact actgacgtaa | 720 |
| ctggtattgt tacacttcca gaaggtactg aaatggtaat gcctggtgat aacattgagc | 780 |
| ttgcagttga actaattgca ccaatcgcta tcgaagac | 818 |

<210> SEQ ID NO 138
<211> LENGTH: 817
<212> TYPE: DNA
<213> ORGANISM: Listeria monocytogenes

<400> SEQUENCE: 138

| | |
|---|---|
| cggagctatc ttagtagtat ctgctgctga tggcccaatg ccacaaactc gtgaacatat | 60 |
| cttactttca cgtcaagttg gtgttccata catcgttgta ttcatgaaca aatgtgacat | 120 |
| ggttgacgat gaagaattac tagaattagt tgaaatggaa attcgtgatc tattaactga | 180 |
| atatgaattc cctggcgatg acattcctgt aatcaaaggt tcagctctta aagcacttca | 240 |
| aggtgaagct gactgggaag ctaaaattga cgagttaatg gaagctgtag attcttacat | 300 |
| tccaactccw gaacgtgata ctgacaaacc attcatgatg ccagttgagg atgtattctc | 360 |
| aatcactggt cgtggaacag ttgcaactgg acgtgttgaa cgtggacaag ttaaagttgg | 420 |

```
tgacgaagta gaagttatcg gtatcgaaga agaaagcaaa aaagtagtag taactggagt    480
agaaatgttc cgtaaattac tagactacgc tgaagctggc gacaacattg gcgcacttct    540
acgtggtgtt gctcgtgaag atatccaacr tggtcaagta ttagctaaac caggttcgat    600
tactccacac actaacttca aagctgaaac ttatgtttta actaaagaag aaggtggacg    660
tcacactcca ttcttcaaca actaccgccc acaattctat ttccgtacta ctgacgtaac    720
tggtattgtt acacttccag aaggtactga aatggtaayg cctggtgata acattgagct    780
tgcagttgaa ctaattgcac caatcgctat cgaagac                            817
```

<210> SEQ ID NO 139
<211> LENGTH: 817
<212> TYPE: DNA
<213> ORGANISM: Listeria seeligeri

<400> SEQUENCE: 139

```
cggagctatc ttagtagtat ctgctgctga tggcccaatg ccacaaactc gtgaacatat     60
cttactttca cgtcaagttg gtgttccata catcgttgta ttcatgaaca aatgtgacat    120
ggttgacgat gaagaattac ttgaattagt tgaaatggaa attcgtgatc tattaactga    180
atatgaattc cctggtgatg acattcctgt aatcaaaggt tcagctctta aagcacttca    240
aggtgaagct gactgggaag ctaaaattga cgagttaatg gaagctgtag attcttacat    300
tccaactcca gaacgtgata ctgacaaacc attcatgatg ccagttgagg atgtattctc    360
aatcactggt cgtggaactg ttgcaactgg acgtgttgaa cgtggacaag ttaaagttgg    420
tgacgaagta gaagttatcg gtattgaaga agaaagcaaa aaagtaatag taactggagt    480
agaaatgttc cgtaaattac tagactacgc tgaagctggc gacaacattg gcgcacttct    540
acgtggtgtt gctcgtgaag atatccaacg tggtcaagta ttagctaaac caggttcgat    600
tactccacat actaacttca aagctgaaac ttatgtttta actaaagaag aaggtggacg    660
tcacactcca ttcttcaaca actaccgccc acaattctat ttccgtacta ctgacgtaac    720
tggtattgtt acacttccag aaggtactga aatggtaatg cctggtgata acattgagct    780
tgcagttgaa ctaattgcac caatcgctat cgaagac                            817
```

<210> SEQ ID NO 140
<211> LENGTH: 814
<212> TYPE: DNA
<213> ORGANISM: Staphylococcus aureus

<400> SEQUENCE: 140

```
cggtggtatc ttagtagtat ctgctgctga cggtccaatg ccacaaactc gtgaacacat     60
tcttttatca cgtaacgttg gtgtaccagc attagtagta ttcttaaaca agttgacat    120 ggttgacgat gaagaattat tagaattagt agaaatggaa gttcgtgact tattaagcga    180
atatgacttc ccaggtgacg atgtacctgt aatcgctggt tcagcattar aagctttaga    240
aggcgatgct caatacgaag aaaaaatctt agaattartg gaagctgtag atacttacat    300
tccaactcca gaacgtgatt ctgacaaacc attcatgatg ccagttgagg acgtattctc    360
aatcactggt cgtggtactg ttgctacagg ccgtgttgaa cgtggtcaaa tcaaagttgg    420
tgaagaagtt gaaatcatcg gtttacatga cacatctaaa acaactgtta caggtgttga    480
aatgttccgt aaattattag actacgctga agctggtgac aacattggtg cattattacg    540
tggtgttgct cgtgaagacg tacaacgtgg tcaagtatta gctgctcctg gttcaattac    600
accacatact gaattcaaag cagaagtata cgtattatca aaagacgaag gtggacgtca    660
```

```
cactccattc ttctcaaact atcgtccaca attctatttc cgtactactg acgtaactgg    720
tgttgttcac ttaccagaag gtactgaaat ggtaatgcct ggtgataacg ttgaaatgac    780
agtagaatta atcgctccaa tcgcgattga agac                                814

<210> SEQ ID NO 141
<211> LENGTH: 814
<212> TYPE: DNA
<213> ORGANISM: Staphylococcus epidermidis

<400> SEQUENCE: 141
cggcggtatc ttagttgtat ctgctgctga cggtccaatg ccacaaactc gtgaacacat     60
cttattatca cgtaacgttg gtgtaccagc attagttgta ttcttaaaca agttgacat    120 ggtagacgac gaagaattat tagaattagt tgaaatggaa gttcgtgact tattaagcga    180
atatgacttc ccaggtgacg atgtacctgt aatcgctggt tctgcattaa aagcattaga    240
aggcgatgct gaatacgaac aaaaaatctt agacttaatg caagcagttg atgattacat    300
tccaactcca gaacgtgatt ctgacaaacc attcatgatg ccagttgagg acgtattctc    360
aatcactggt cgtggtactg ttgctacagg ccgtgttgaa cgtggtcaaa tcaaagtwgg    420
tgaagaagtt gaaatcatcg gtatgcacga aacttctaaa caactgtta ctggtgtaga    480 aatgttccgt aaattattag actacgctga agctggtgac aacatcggtg ctttattacg    540
tggtgttgca cgtgaagacg tacaacgtgg tcaagtatta gctgctcctg gttctattac    600
accacacaca aaattcaaag ctgaagtata cgtattatct aaagatgaag gtggacgtca    660
cactccattc ttcactaact atcgcccaca attctatttc crtactactg acgtaactgg    720
tgttgtaaac ttaccagaag gtacagaaat ggttatgcct ggcgacaacg ttgaaatgac    780
agttgaatta atcgctccaa tcgctatcga agac                                814

<210> SEQ ID NO 142
<211> LENGTH: 817
<212> TYPE: DNA
<213> ORGANISM: Staphylococcus saprophyticus

<400> SEQUENCE: 142
cggagctatc ttagtagtat ctgctgctga tggcccaatg ccacaaactc gtgaacacat     60
tcttttatca cgtracgttg gtgytccagc attagttgta ttcttaaaca agttgacat    120 ggttgacgay gaagaattat tagaattrgt agaaatggaa gttcgtgrct tattaagcga    180
atatgacttc ccaggtgacg atgtacctgt aatctctggt tctgcattaa aagctttaga    240
aggcgacgct gactatgagc aaaaaatctt agacttaatg caagctgttg atgactycat    300
tccaacacca gaacgtgatt ctgacaaacc attcatgatg ccagttgagg acgtattctc    360
aatcactggt cgtggtactg ttgctacagg ccgtgttgaa cgtggtcaaa tcaaagtcgg    420
tgaagaaatc garatcatcg gtatgcaaga agaatcaagc aaaacaactg ttactggtgt    480
agaaatgttc cgtaaattat tagactacgc tgaagctggt gacaacattg gtgcattatt    540
acgtggtgtt tcacgtgatg atgtacaacg tggtcaagtt ttagctgctc ctggtactat    600
cacaccacat acaaaattca agcggatgt ttacgttta tctaaagatg aaggtggtcg    660
tcatacgcca ttcttcacta actaccgccc acaattctat ttccgtacta ctgacgtaac    720
tggtgttgtt aacttaccag aaggtactga aatggttatg cctggcgata acgttgaaat    780
ggatgttgaa ttaatttctc caatcgctat tgaagac                             817
```

```
<210> SEQ ID NO 143
<211> LENGTH: 817
<212> TYPE: DNA
<213> ORGANISM: Staphylococcus simulans

<400> SEQUENCE: 143
cggcggtatc ttagtagtat ctgctgcaga tggtccaatg ccacaaactc gtgaacacat      60
cttattatca cgtaacgttg gtgtaccagc tttagttgta ttcttaaaca aagctgacat     120
ggttgacgac gaagaattat tagaattagt tgaaatggaa gttcgtgact tattatctga     180
atacgacttc cctggtgacg atgtaccagt tatcgttggt tctgcattaa aagctttaga     240
aggcgaccca gaatacgaac aaaaaatctt agacttaatg caagctgtag atgactacat     300
cccaactcca gaacgtgact ctgataaacc attcatgatg ccagttgagg acgtattctc     360
aatcactggt cgtggtactg tagcaacagg ccgtgttgaa cgtggtcaaa tcaaagtcgg     420
tgaagaagtt gaaatcatcg gtatcactga agaaagcaag aaaacaacag ttacaggtgt     480
agaaatgttc cgtaaattat tagactacgc tgaagctggt gacaacatcg gtgctttatt     540
acgtggtgtt gcacgtgaag acgtacaacg tggacaagta ttagcagctc ctggctctat     600
tactccacac acaaaattca aagctgatgt ttacgtttta tctaaagaag aaggtggacg     660
tcatactcca ttcttcacta actaccgccc acaattctac ttccgtacta ctgacgtaac     720
tggcgttgtt cacttaccag aaggtactga atggttatg cctggcgata acgtagaaat     780
gactgttgaa ttgatcgctc aatcgcgat tgaagac                              817

<210> SEQ ID NO 144
<211> LENGTH: 817
<212> TYPE: DNA
<213> ORGANISM: Streptococcus agalactiae

<400> SEQUENCE: 144
cggagctatc cttgtagttg cttcaactga tggaccaatg ccacaaactc gtgagcacat      60
ccttctttca cgtcaagttg gtgttaaaca ccttatcgta ttcatgaaca aagttgacct     120
tgttgatgat gaagaattgc ttgaattggt tgaaatggaa attcgtgacc ttctttcaga     180
atacgacttc ccaggtgatg accttccagt tatccaaggt tcagctctta aagcacttga     240
aggcgacgaa aaatacgaag acatcatcat ggaattgatg agcactgttg atgagtacat     300
tccagaacca gaacgtgata ctgacaaacc tttacttctt ccagttgaag atgtattctc     360
aatcactgga cgtggtacag ttgcttcagg acgtatcgac cgtggtactg ttcgtgtcaa     420
cgacgaagtt gaaatcgttg gtattaaaga agatatccaa aaagcagttg ttactggtgt     480
tgaaatgttc cgtaaacaac ttgacgaagg tcttgcaggg gacaacgttg gtgttcttct     540
tcgtggtgtt caacgtgatg aaatcgaacg tggtcaagtt cttgctaaac caggttcaat     600
caacccacac actaaattta aaggtgaagt ttacatcctt tctaaagaag aaggtggacg     660
tcatactcca ttcttcaaca actaccgtcc acaattctac ttccgtacaa ctgacgtaac     720
aggttcaatc gaacttccag caggaacaga aatggttatg cctggtgata acgttactat     780
cgaagttgaa ttgattcacc caatcgccgt agaacaa                              817

<210> SEQ ID NO 145
<211> LENGTH: 817
<212> TYPE: DNA
<213> ORGANISM: Streptococcus pneumoniae

<400> SEQUENCE: 145
cggagctatc cttgtagtag cttcaactga cggaccaatg ccacaaactc gtgagcacat      60
```

```
ccttctttca cgtcaggttg gtgttaaaca ccttatcgtc ttcatgaaca aagttgactt    120
ggttgacgac gaagaattgc ttgaattggt tgaaatggaa atccgtgacc tattgtcaga    180
atacgacttc ccaggtgacg atcttccagt tatccaaggt tcagcactta aagctcttga    240
aggtgactct aaatacgaag acatcgttat ggaattgatg aacacagttg atgagtatat    300
cccagaacca gaacgtgaca ctgacaaacc attgcttctt ccagtcgagg acgtattctc    360
aatcactgga cgtggtacag ttgcttcagg acgtatcgac cgtggtatcg ttaaagtcaa    420
cgacgaaatc gaaatcgttg gtatcaaaga agaaactcra aaagcagttg ttactggtgt    480
tgaaatgttc cgtaaacaac ttgacgaagg tcttgctgga gataacgtag gtgtccttct    540
tcgtggtgtt caacgtgatg aaatcgaacg tggacaagtt atcgctaaac caggttcaat    600
caacccacac actaaattca aggtgaagt ctacatcctt actaaagaag aaggtggacg    660
tcacactcca ttcttcaaca actaccgtcc acaattctac ttccgtacta ctgacgttac    720
aggttcaatc gaacttccag caggtactga atggtaatg cctggtgata acgtgacaat    780
cgacgttgag ttgattcacc caatcgccgt agaacaa                              817

<210> SEQ ID NO 146
<211> LENGTH: 817
<212> TYPE: DNA
<213> ORGANISM: Streptococcus salivarius

<400> SEQUENCE: 146
cggtgcgatc cttgtagtag catctactga cggaccaatg ccacaaactc gtgagcacat     60
ccttctttca cgtcaggttg gtgttaaaca ccttatcgtc ttcatgaaca aagttgactt    120
ggttgacgat gaagaattgc ttgaattggt tgaaatggaa atccgtgacc ttctttcaga    180
atacgatttc ccaggtgatg acattccagt tatccaaggt tcagctctta aagctcttga    240
aggtgattct aaatacgaag acatcatcat ggacttgatg aacactgttg acgaatacat    300
cccagaacca gaacgtgaca ctgacaaacc attgttgctt ccagtcgaag acgtattctc    360
aatcactggt cgtggtactg ttgcttcagg acgtatcgac cgtggtgttg ttcgtgtcaa    420
tgacgaagtt gaaatcgttg gtcttaaaga agacatccaa aaagcagttg ttactggtgt    480
tgaaatgttc cgtaaacaac ttgacgragg tattgccgga gataacgtcg gtgttcttct    540
tcgtggtatc caacgtgatg aaatcgaacg tggtcaagta ttggctgcac ctggttcaat    600
caacccacac actaaattca aggtgaagt ttacatcctt tctaaagaag aaggtggacg    660
tcacactcca ttcttcaaca actaccgtcc acagttctac ttccgtacaa ctgacgtaac    720
aggttcaatc gaacttcctg caggtactga atggttatg cctggtgata acgtgactat    780
cgacgttgag ttgatccacc caatcgccgt tgaacaa                              817

<210> SEQ ID NO 147
<211> LENGTH: 897
<212> TYPE: DNA
<213> ORGANISM: Agrobacterium tumefaciens

<400> SEQUENCE: 147
aacatgatca ccggtgctgc cgagatggac ggcgcgatcc tggtttgctc ggctgccgac     60
ggcccgatgc cacagacccg cgagcacatc ctgcttgccc gtcaggtggg cgttccggcc    120
atcgtcgtgt tcctcaacaa ggtcgaccag gttgacgacg ccgagcttct cgagctcgtc    180
gagcttgaag ttcgcgaact tctgtcgtcc tacgacttcc cgggcgacga tatcccgatc    240
atcaagggtt cggcacttgc tgctcttgaa gattctgaca agaagatcgg tgaagacgcg    300
```

```
atccgcgagc tgatggctgc tgtcgacgcc tacatcccga cgcctgagcg tccgatcgac    360
cagccgttcc tgatgccgat cgaagacgtg ttctcgatct cgggtcgtgg tacggttgtg    420
acgggtcgcg ttgagcgcgg tatcgtcaag gttggtgaag aagtcgaaat cgtcggcatc    480
cgtccgacct cgaagacgac tgttaccggc gttgaaatgt ccgcaagct gctcgaccag     540 ggccaggccg cgacaacat cggtgcactc gttcgcggcg ttacccgtga cggcgtcgag     600
cgtggtcaga tcctgtgcaa gccgggttcg gtcaagccgc acaagaagtt catggcagaa    660
gcctacatcc tgacgaagga agaaggcggc cgtcatacgc cgttcttcac gaactaccgt    720
ccgcagttct acttccgtac gactgacgtt accggtatcg tttcgcttcc tgaaggcacg    780
gaaatggtta tgcctggcga caacgtcact gttgaagtcg agctgatcgt tccgatcgcg    840
atggaagaaa agctgcgctt cgctatccgc gaaggcggcc gtaccgtcgg cgccggc       897

<210> SEQ ID NO 148
<211> LENGTH: 885
<212> TYPE: DNA
<213> ORGANISM: Bacillus subtilis

<400> SEQUENCE: 148
atgatcactg gtgctgcgca aatggacgga gctatccttg tagtatctgc tgctgatggc     60
ccaatgccac aaactcgtga gcacatcctt ctttctaaaa acgttggtgt accatacatc    120
gttgtattct taaacaaatg cgacatggta gacgacgaag agcttcttga actagttgaa    180
atggaagttc gcgatcttct tagcgaatac gacttccctg gtgatgatgt accagttgtt    240
aaaggttctg ctcttaaagc tcttgaagga gacgctgagt gggaagctaa aatcttcgaa    300
cttatggatg cggttgatga gtacatccca actccagaac gcgacactga aaaccattc    360 atgatgccag ttgaggacgt attctcaatc actggtcgtg gtacagttgc tactggccgt    420
gtagaacgcg gacaagttaa agtcggtgac gaagttgaaa tcatcggtct tcaagaagag    480
aacaagaaaa caactgttac aggtgttgaa atgttccgta agcttcttga ttacgctgaa    540
gctggtgaca acattggtgc ccttcttcgc ggtgtatctc gtgaagaaat ccaacgtggt    600
caagtacttg ctaaaccagg tacaatcact ccacacagca aattcaaagc tgaagtttac    660 gttcttttcta aagaagaggg tggacgtcat actccattct tctctaacta ccgtcctcag    720
ttctacttcc gtacaactga cgtaactggt atcatccatc ttccagaagg cgtagaaatg    780
gttatgcctg gagataacac tgaaatgaac gttgaactta tttctacaat cgctatcgaa    840
gaaggaactc gtttctctat tcgtgaaggc ggacgtactg ttggt                    885

<210> SEQ ID NO 149
<211> LENGTH: 882
<212> TYPE: DNA
<213> ORGANISM: Bacteroides fragilis

<400> SEQUENCE: 149
atggttactg gtgctgctca gatggacggt gctatcattg tagttgctgc tactgatggt     60
ccgatgcctc agactcgtga gcacatcctt ttggctcgtc aggtaaacgt tccgaagctg    120
gttgtattca tgaacaagtg cgatatggtt gaagatgctg agatgttgga acttgttgaa    180
atggaaatga gagaattgct ttcattctat gatttcgacg tgacaataac tccgatcatt    240
cagggttctg ctcttggtgc attgaacggc gtagaaaaat gggaagacaa agtaatggaa    300
ctgatggaag ctgttgatac ttggattcca ctgcctccgc gcgatgttga taaccttct     360 ttgatgccgg tagaagacgt gttctctatc acaggtcgtg gtactgtagc tacaggtcgt    420
```

```
atcgaaactg gtgttatcca tgtaggtgat gaaatcgaaa tcctcggttt gggtgaagat    480
aagaaatcag ttgtaacagg tgttgaaatg ttccgcaaac ttctggatca gggtgaagct    540
ggtgacaacg taggtctgtt gcttcgtggt gttgacaaga acgaaatcaa acgtggtatg    600
gttctttgta aaccgggtca gattaaacct cactctaaat tcaaagcaga ggtttatatc    660
ctgaagaaag aagaaggtgg tcgtcacact ccattccata acaaatatcg tcctcagttc    720
tacctgcgta ctatggactg tacaggtgaa atcactcttc cggaaggaac tgaaatggta    780
atgccgggtg ataacgtaac tatcactgta gagttgatct atccggttgc actgaacatc    840
ggtcttcgtt tcgctatccg cgaaggtgga cgtacagtag gt                      882

<210> SEQ ID NO 150
<211> LENGTH: 888
<212> TYPE: DNA
<213> ORGANISM: Borrelia burgdorferi

<400> SEQUENCE: 150
aatatgatta caggagcagc tcaaatggat gcagcgatac ttttagttgc tgctgatagt     60
ggtgctgagc tcaaacaaa agagcatttg cttcttgctc aaagaatggg aataaagaaa    120
ataatagttt ttttaaataa attggactta gcagatcctg aacttgttga gcttgttgaa    180
gttgaagttt tagaacttgt tgaaaaatat ggcttttcag ctgatactcc aataatcaaa    240
ggttcagctt ttggggctat gtcaaatcca gaagatcctg aatctacaaa atgcgttaaa    300
gaacttcttg aatctatgga taattatttt gatcttccag aaagagatat tgacaagcca    360
tttttgcttg ctgttgaaga tgtatttct atttcaggaa gaggcactgt tgctactggg    420
cgtattgaaa gaggtattat taaagttggt caagaagttg aaatagttgg aattaaagaa    480
accagaaaaa ctactgttac tggtgttgaa atgttccaga aaattcttga gcaaggtcaa    540
gcaggggata atgttggtct tcttttgaga ggcgttgata aaaagacat tgagaggggg    600 caagttttgt cagctccagg tacaattact ccacacaaga aatttaaagc ttcaattat     660 tgtttgacta agaagaagg cggtaggcac aagccatttt tcccagggta tagaccacag    720 ttcttttttta gaacaaccga tgttactgga gttgttgctt tagagggcaa agaaatggtt    780
atgcctggtg ataatgttga tattattgtt gagctgatct cttcaatagc tatggataag    840
aatgtagaat ttgctgttcg agaaggtgga agaaccgttg cttcagga                888

<210> SEQ ID NO 151
<211> LENGTH: 894
<212> TYPE: DNA
<213> ORGANISM: Brevibacterium linens

<400> SEQUENCE: 151
aacatgatca ccggtgccgc tcagatggac ggtgcgatcc tcgtcgtcgc cgctaccgac     60
ggaccgatgc cccagacccg tgagcacgtg ctgctcgcgc gtcaggtcgg cgttccctac    120
atcgtcgtgg ctctgaacaa gtccgacatg tcgatgacg aggagctcct cgagctcgtc    180
gaattcgagg tccgcgacct gctctcgagc caggacttcg acggagacaa cgctccggtc    240
attccggtgt ccgctctcaa ggcgctggaa ggcgacgaga agtgggtcaa gagcgttcag    300
gatctcatgg ctgccgtcga tgacaacgtt ccggagccgg agcgcgatgt cgacaagccg    360
ttcctcatgc ccgtcgagga cgtcttcacg atcaccggtc gtggaaccgt cgtcaccggt    420
cgtgtcgagc gcggcgtgct cctgcctaac gacgaaatcg aaatcgtcgg catcaaggag    480
aagtcgtcca agacgactgt caccgctatc gagatgttcc gcaagaccct gccggatgcc    540
```

```
cgtgcaggtg agaacgtcgg tctgctcctc cgcggcacca agcgcgagga tgttgagcgc    600
ggtcaggtca tcgtgaagcc gggttcgatc accccgcaca ccaagttcga ggctcaggtc    660
tacatcctga gcaaggacga gggcggacgt cacaacccgt tctactcgaa ctaccgtccg    720
cagttctact tccggaccac ggacgtcacc ggtgtcatca cgctgcccga gggcaccgag    780
atggtcatgc ccggcgacaa caccgatatg tcggtcgagc tcatccagcc gatcgctatg    840
gaggaccgcc tccgcttcgc aatccgcgaa ggtggccgca ccgtcggcgc cggt          894
```

<210> SEQ ID NO 152
<211> LENGTH: 888
<212> TYPE: DNA
<213> ORGANISM: Burkholderia cepacia

<400> SEQUENCE: 152

```
atgatcacgg gcgcagcgca gatggacggc gcgatcctgg tttgctcggc agcagacggc     60
ccgatgccgc aaacgcgtga gcacatcctg ctggcgcgtc aggttggtgt tccgtacatc    120
atcgtgttcc tgaacaagtg cgacagtgtg gacgacgctg aactgctcga gctggtcgag    180
atggaagttc gcgaactcct gtcgaagtac gacttcccgg gcgacgacac gccgatcgtg    240
aagggttcgg ccaagctggc gctggaaggc gacacgggcg agctgggcga agtggcgatc    300
atgagcctgg cagacgcgct ggacacgtac atcccgacgc cggagcgtgc agttgacggc    360
gcgttcctga tgccggtgga agacgtgttc tcgatctcgg gccgtggtac ggtggtgacg    420
ggtcgtgtcg agcgcggcat cgtgaaggtc ggcgaagaaa tcgaaatcgt cggtatcaag    480
ccgacggtga agacgacctg cacgggcgtt gaaatgttcc gcaagctgct ggaccaaggt    540
caggcaggcg acaacgtcgg tatcctgctg cgcggcacga agcgtgaaga cgtggagcgt    600
ggccaggttc tggcgaagcc gggttcgatc acgccgcaca cgcacttcac ggctgaagtg    660
tacgtgctga gcaaggacga aggcggccgt cacacgccgt tcttcaacaa ctaccgtccg    720
cagttctact tccgtacgac ggacgtgacg ggctcgatcg agctgccgaa ggacaaggaa    780
atggtgatgc cgggcgacaa cgtgtcgatc acggtgaagc tgattgctcc gatcgcgatg    840
gaagaaggtc tgcgcttcgc aatccgtgaa ggcggccgta cggtcggc                 888
```

<210> SEQ ID NO 153
<211> LENGTH: 891
<212> TYPE: DNA
<213> ORGANISM: Chlamydia trachomatis

<400> SEQUENCE: 153

```
aacatgatca ccggtgcggc tcaaatggac ggggctattc tagtagtttc tgcaacagac     60
ggagctatgc ctcaaactaa agagcatatt cttttggcaa gacaagttgg ggttccttac    120
atcgttgttt ttctcaataa aattgacatg atttccgaag aagacgctga attggtcgac    180
ttggttgaga tggagttggc tgagcttctt gaagagaaag gatacaaagg gtgtccaatc    240
atcagaggtt ctgctctgaa agctttggaa ggagatgctg catacataga gaaagttcga    300
gagctaatgc aagccgtcga tgataatatc cctactccag aaagagaaat tgacaagcct    360
ttcttaatgc ctattgagga cgtgttctct atctccggac gaggaactgt agtaactgga    420
cgtattgagc gtggaattgt taaagtttcc gataaagttc agttggtcgg tcttagagat    480
actaaagaaa cgattgttac tggggttgaa atgttcagaa aagaactccc agaaggtcgt    540
gcaggagaga acgttggatt gctcctcaga ggtattggta agaacgatgt ggaaagagga    600
atggttgttt gcttgccaaa cagtgttaaa cctcatacac agtttaagtg tgctgtttac    660
```

| | |
|---|---|
| gttctgcaaa aagaagaagg tggacgacat aagcctttct tcacaggata tagacctcaa | 720 |
| ttcttcttcc gtacaacaga cgttacaggt gtggtaactc tgcctgaggg agttgagatg | 780 |
| gtcatgcctg gggataacgt tgagtttgaa gtgcaattga ttagccctgt ggctttagaa | 840 |
| gaaggtatga gatttgcgat tcgtgaaggt ggtcgtacaa tcggtgctgg a | 891 |

<210> SEQ ID NO 154
<211> LENGTH: 891
<212> TYPE: DNA
<213> ORGANISM: Escherichia coli

<400> SEQUENCE: 154

| | |
|---|---|
| aacatgatca ccggtgctgc gcagatggac ggcgcgatcc tggtagttgc tgcgactgac | 60 |
| ggcccgatgc cgcagactcg tgagcacatc ctgctgggtc gtcaggtagg cgttccgtac | 120 |
| atcatcgtgt tcctgaacaa atgcgacatg gttgatgacg aagagctgct ggaactggtt | 180 |
| gaaatggaag ttcgtgaact tctgtctcag tacgacttcc cgggcgacga cactccgatc | 240 |
| gttcgtggtt ctgctctgaa agcgctggaa ggcgacgcag agtgggaagc gaaaatcctg | 300 |
| gaactggctg gcttcctgga ttcttacatt ccggaaccag agcgtgcgat tgacaagccg | 360 |
| ttcctgctgc cgatcgaaga cgtattctcc atctccggtc gtggtaccgt tgttaccggt | 420 |
| cgtgtagaaa cgcgtatcat caaagttggt gaagaagttg aaatcgttgg tatcaaagag | 480 |
| actcagaagt ctacctgtac tggcgttgaa atgttccgca aactgctgga cgaaggccgt | 540 |
| gctggtgaga acgtaggtgt tctgctgcgt ggtatcaaac gtgaagaaat cgaacgtggt | 600 |
| caggtactgg ctaagccggg caccatcaag ccgcacacca gttcgaatc tgaagtgtac | 660 |
| attctgtcca aagatgaagg cggccgtcat actccgttct tcaaaggcta ccgtccgcag | 720 |
| ttctacttcc gtactactga cgtgactggt accatcgaac tgccggaagg cgtagagatg | 780 |
| gtaatgccgg cgacaacat caaaatggtt gttaccctga tccacccgat cgcgatggac | 840 |
| gacggtctgc gtttcgcaat ccgtgaaggc ggccgtaccg ttggcgcggg c | 891 |

<210> SEQ ID NO 155
<211> LENGTH: 891
<212> TYPE: DNA
<213> ORGANISM: Fibrobacter succinogenes

<400> SEQUENCE: 155

| | |
|---|---|
| aacatggtga ctggtgctgc tcagatggac ggcgctatcc tcgttgttgc cgctactgac | 60 |
| ggtccgatgc cgcagactcg cgaacacatc cttctcgctc accaggttgg cgtgccgaag | 120 |
| atcgtcgtgt tcatgaacaa gtgcgacatg gttgacgatg ctgaaattct cgacctcgtc | 180 |
| gaaatggaag ttcgcgaact cctctccaag tatgacttcg acggtgacaa cacccccgatc | 240 |
| atccgtggtt ccgctctcaa ggcccctgaa ggcgatccgg aataccagga caaggtcatg | 300 |
| gaactcatga acgcttgcga cgaatacatc ccgctcccgc agcgcgatac cgacaagccg | 360 |
| ttcctcatgc cgatcgaaga cgtgttcacg attactggcc gcggcactgt cgctactggc | 420 |
| cgtatcgaac gcggtgtcgt tcgcttgaac gacaaggttg aacgtatcgg tctcggtgaa | 480 |
| accaccgaat acgtcatcac cggtgttgaa atgttccgta agctcctcga cgacgctcag | 540 |
| gcaggtgaca acgttggtct cctcctccgt ggtgctgaaa agaaggacat cgtccgtggc | 600 |
| atggttctcg cagctccgaa gtcgtcact ccgcacaccg aatttaaggc tgaaatctac | 660 |
| gttctcacga aggacgaagg tggccgtcac acgccgttca tgaatggcta ccgtccgcag | 720 |
| ttctacttcc gcaccaccga cgttactggt acgatccagc tcccggaagg tgtcgaaatg | 780 |

```
gttactccgg gtgacacggt cacgatccac gtgaacctca tcgctccgat cgctatggaa    840
aagcagctcc gcttcgctat ccgtgaaggt ggacgtactg ttggtgctgg c             891
```

<210> SEQ ID NO 156
<211> LENGTH: 894
<212> TYPE: DNA
<213> ORGANISM: Flavobacterium ferrugineum

<400> SEQUENCE: 156

```
aacatgatca ccggtgctgc ccagatggac ggtgctatct tagttgtggc tgcatcagac     60
ggtcctatgc ctcaaacaaa agaacacatc ctgcttgctg cccaggtagg tgtacctaaa    120
atggttgtgt ttctgaataa agttgacctc gttgacgacg aagagctcct ggagctggtt    180
gagatcgagg ttcgcgaaga actgactaaa cgcggtttcg acggcgacaa cactccaatc    240
atcaaaggtt ccgctacagg cgccctcgct ggtgaagaaa agtgggttaa agaaattgaa    300
aacctgatgg acgctgttga cagctacatc ccactgcctc ctcgtccggt tgatctgccg    360
ttcctgatga gcgtagagga cgtattctct atcactggtc gtggtactgt tgctaccggt    420
cgtatcgagc gtggccgtat caaagttggt gagcctgttg agatcgtagg tctgcaggag    480
tctcccctga actctaccgt tacaggtgtt gagatgttcc gcaaactcct cgacgaaggt    540
gaagctggtg ataacgccgg tctcctcctc cgtggtgttg aaaaaacaca gatccgtcgc    600
ggtatggtaa tcgttaaacc cggttccatc actccgcaca cggacttcaa aggcgaagtt    660
tacgtactga gcaaagacga aggtggccgt cacactccat tcttcaacaa ataccgtcct    720
caattctact ccgtacaac tgacgttaca ggtgaagtag aactgaacgc aggaacagaa    780
atggttatgc ctggtgataa caccaacctg accgttaaac tgatccaacc gatcgctatg    840
gaaaaaggtc tgaaattcgc gatccgcgaa ggtggccgta ccgtaggtgc agga          894
```

<210> SEQ ID NO 157
<211> LENGTH: 891
<212> TYPE: DNA
<213> ORGANISM: Haemophilus influenzae

<400> SEQUENCE: 157

```
aatatgatta ctggtgcggc acaaatggat ggtgctattt tagtagtagc agcaacagat     60
ggtcctatgc cacaaactcg tgaacacatc ttattaggtc gccaagtagg tgttccatac    120
atcatcgtat tcttaaacaa atgcgacatg gtagatgacg aagagttatt agaattagtc    180
gaaatggaag ttcgtgaact tctatctcaa tatgacttcc aggtgacga tacaccaatc    240 gtacgtggtt cagcattaca agcgttaaac ggcgtagcag aatgggaaga aaaaatcctt    300
gagttagcaa accacttaga tacttacatc ccagaaccag aacgtgcgat tgaccaaccg    360
ttccttcttc aatcgaaga tgtgttctca atctcaggtc gtggtactgt agtaacaggt    420
cgtgtagaac gaggtattat ccgtacaggt gatgaagtag aaatcgtcgg tatcaaagat    480
acagcgaaaa ctactgtaac gggtgttgaa atgttccgta aattacttga cgaaggtcgt    540
gcaggtgaaa catcggtgc attattacgt ggtaccaaac gtgaagaaat cgaacgtggt    600
caagtattag cgaaaccagg ttcaatcaca ccacacactg acttcgaatc agaagtgtac    660
gtattatcaa aagatgaagg tggtcgtcat actccattct tcaaaggtta ccgtccacaa    720
ttctatttcc gtacaacaga cgtgactggt acaatcgaat taccagaagg cgtggaaatg    780
gtaatgccag cgataacat caagatgaca gtaagcttaa tccacccaat tgcgatggat    840
caaggtttac gtttcgcaat ccgtgaaggt ggccgtacag taggtgcagg c             891
```

<210> SEQ ID NO 158
<211> LENGTH: 906
<212> TYPE: DNA
<213> ORGANISM: Helicobacter pylori

<400> SEQUENCE: 158

```
aacatgatca ccggtgcggc gcaaatggac ggagcgattt tggttgtttc tgcagctgat      60
ggccctatgc ctcaaactag ggagcatatc ttattgtctc gtcaagtagg cgtgcctcac     120
atcgttgttt tcttaaacaa acaagacatg gtagatgacc aagaattgtt agaacttgta     180
gaaatggaag tgcgcgaatt gttgagcgcg tatgaatttc ctggcgatga cactcctatc     240
gtagcgggtt cagctttaag agctttagaa gaagcaaagg ctggtaatgt gggtgaatgg     300
ggtgaaaaag tgcttaaact tatggctgaa gtggatgcct atatccctac tccagaaaga     360
gacactgaaa aaactttctt gatgccggtt gaagatgtgt tctctattgc gggtagaggg     420
actgtggtta caggtaggat tgaaagaggc gtggtgaaag taggcgatga agtggaaatc     480
gttggtatca gacctacaca aaaaacgact gtaaccggtg tagaaatgtt taggaaagag     540
ttggaaaaag gtgaagccgg cgataatgtg ggcgtgcttt tgagaggaac taaaaaagaa     600
gaagtggaac gcggtatggt tctatgcaaa ccaggttcta tcactccgca caagaaattt     660
gagggagaaa tttatgtcct ttctaaagaa gaaggcggga gacacactcc attcttcacc     720
aattaccgcc cgcaattcta tgtgcgcaca actgatgtga ctggctctat caccttcct      780
gaaggcgtag aaatggttat gcctggcgat aatgtgaaaa tcactgtaga gttgattagc     840
cctgttgcgt tagagttggg aactaaatt gcgattcgtg aaggcggtag gaccgttggt      900
gctggt                                                                 906
```

<210> SEQ ID NO 159
<211> LENGTH: 891
<212> TYPE: DNA
<213> ORGANISM: Micrococcus luteus

<400> SEQUENCE: 159

```
aacatgatca ccggcgccgc tcagatggac ggcgcgatcc tcgtggtcgc cgctaccgac      60
ggcccgatgg cccagacccg tgagcacgtg ctcctggccc gccaggtcgg cgtgccggcc     120
ctgctcgtgg ccctgaacaa gtcggacatg gtggaggacg aggagctcct cgagcgtgtc     180
gagatggagg tccggcagct gctgtcctcc aggagcttcg acgtcgacga ggccccggtc     240
atccgcacct ccgctctgaa ggccctcgag ggcgaccccc agtgggtcaa gtccgtcgag     300
gacctcatgg atgccgtgga cgagtacatc ccggacccgg tgcgcgacaa ggacaagccg     360
ttcctgatgc cgatcgagga cgtcttcacg atcaccggcc gtggcaccgt ggtgaccggt     420
cgcgccgagc gcggcaccct gaagatcaac tccgaggtcg agatcgtcgg catccgcgac     480
gtgcagaaga ccactgtcac cggcatcgag atgttccaca agcagctcga cgaggcctgg     540
gccggcgaga actgcggtct gctcgtgcgc ggtctgaagc gcgacgacgt cgagcgcggc     600
caggtgctgg tggagccggg ctccatcacc ccgcacacca acttcgaggc gaacgtctac     660
atcctgtcca aggacgaggg tgggcgtcac acccgttct actcgaacta ccgcgcgcag     720
ttctacttcc gcaccaccga cgtcaccggc gtcatcacgc tgcccgaggg caccgagatg     780
gtcatgcccg cgacaccac cgagatgtcg gtcgagctca tccagccgat cgccatggag     840
gagggcctcg gcttcgccat ccgcgagggt ggccgcaccg tgggctccgg c              891
```

<210> SEQ ID NO 160
<211> LENGTH: 891
<212> TYPE: DNA
<213> ORGANISM: Mycobacterium tuberculosis

<400> SEQUENCE: 160

| aacatgatca ccggcgccgc gcagatggac ggtgcgatcc tggtggtcgc cgccaccgac | 60 |
| gccccgatgc cccagacccg cgagcacgtt ctgctggcgc gtcaagtggg tgtgccctac | 120 |
| atcctggtag cgctgaacaa ggccgacgca gtggacgacg aggagctgct cgaactcgtc | 180 |
| gagatggagg tccgcgagct gctggctgcc caggaattcg acgaggacgc cccggttgtg | 240 |
| cgggtctcgg cgctcaaggc gctcgagggt gacgcgaagt gggttgcctc tgtcgaggaa | 300 |
| ctgatgaacg cggtcgacga gtcgattccg gacccggtcc gcgagaccga caagccgttc | 360 |
| ctgatgccgg tcgaggacgt cttcaccatt accggccgcg gaaccgtggt caccggacgt | 420 |
| gtggagcgcg gcgtgatcaa cgtgaacgag aagttgaga tcgtcggcat tcgcccatcg | 480 |
| accaccaaga ccaccgtcac cggtgtggag atgttccgca agctgctcga ccagggccag | 540 |
| gcgggcgaca acgttggttt gctgctgcgg ggcgtcaagc gcgaggacgt cgagcgtggc | 600 |
| caggttgtca ccaagcccgg caccaccacg ccgcacaccg agttcgaagg ccaggtctac | 660 |
| atcctgtcca aggacgaggg cggccggcac acgccgttct tcaacaacta ccgtccgcag | 720 |
| ttctacttcc gcaccaccga cgtgaccggt gtggtgacac tgccggaggg caccgagatg | 780 |
| gtgatgcccg gtgacaacac caacatctcg gtgaagttga tccagcccgt cgccatggac | 840 |
| gaaggtctgc gtttcgcgat ccgcgagggt ggccgcaccg tgggcgccgg c | 891 |

<210> SEQ ID NO 161
<211> LENGTH: 891
<212> TYPE: DNA
<213> ORGANISM: Mycoplasma genitalium

<400> SEQUENCE: 161

| aatatgatca caggtgctgc acaaatggat ggagctattc tagttgtttc agcaactgat | 60 |
| agtgtgatgc cccaaacccg cgagcacatc ttacttgccc gccaagtagg ggttcctaaa | 120 |
| atggtagttt ttctaaacaa gtgtgatatt gctagtgatg aagaggtaca agaacttgtt | 180 |
| gctgaagaag tacgtgatct gttaacttcc tatggttttg atggtaagaa cactcctatt | 240 |
| atttatggct cagcttttaaa agcattggaa ggtgatccaa gtgggaggc taagatccat | 300 |
| gatttgatta aagcagttga tgaatggatt ccaactccta cacgtgaagt agataaacct | 360 |
| ttcttattag caattgaaga tacgatgacc attactggta gaggtacagt tgttacagga | 420 |
| agagttgaaa gaggtgaact caaagtaggt caagaagttg aaattgttgg tttaaaacca | 480 |
| attagaaaag cagttgttac tggaattgaa atgttcaaaa aggaacttga ttcagcaatg | 540 |
| gctggtgaca atgctggggt attattacgt ggtgttgaac gtaaagaagt tgaaagaggt | 600 |
| caagttttag caaaaccagg ctctattaaa ccgcacaaga aatttaaagc tgagatctat | 660 |
| gctttaaaga aagaagaagg tggtagacac actggttttt taaacggtta ccgtcctcaa | 720 |
| ttctattcc gtaccactga tgtaactggt tctattgctt tagctgaaaa tactgaaatg | 780 |
| gttctacctg gtgataatgc ttctattact gttgagttaa ttgctcctat cgcttgtgaa | 840 |
| aaaggtagta agttctcaat tcgtgaaggt ggtagaactg taggggcagg c | 891 |

<210> SEQ ID NO 162
<211> LENGTH: 891
<212> TYPE: DNA
<213> ORGANISM: Neisseria gonorrhoeae

<400> SEQUENCE: 162

```
aacatgatta ccggcgccgc acaaatggac ggtgcaatcc tggtatgttc tgctgccgac     60
ggccctatgc cgcaaacccg cgaacacatc ctgctggccc gtcaagtagg cgtaccttac    120
atcatcgtgt tcatgaacaa atgcgacatg gtcgacgatg ccgagctgtt ccaactggtt    180
gaaatggaaa tccgcgacct gctgtccagc tacgacttcc ccggcgacga ctgcccgatc    240
gtacaaggtt ccgcactgaa agccttggaa ggcgatgccg cttacgaaga aaaaatcttc    300
gaactggcta ccgcattgga cagatacatc ccgactcccg agcgtgccgt ggacaaacca    360
ttcctgctgc ctatcgaaga cgtgttctcc atttccggcc gcggtaccgt agtcaccggc    420
cgtgtagagc gaggtatcat ccacgttggt gacgagattg aaatcgtcgg tctgaaagaa    480
acccaaaaaa ccacctgtac cggcgttgaa atgttccgca aactgctgga cgaaggtcag    540
gcgggcgaca acgtaggcgt attgctgcgc ggtaccaaac gtgaagacgt agaacgcggt    600
caggtattgg ccaaacgggg tactatcact cctcacacca agttcaaagc agaagtgtac    660
gtattgagca aagaagaggg cggcccccat accccgtttt tcgccaacta ccgtccccaa    720
ttctacttcc gtaccactga cgtaaccggc acgattactt tggaaaaagg tgtggaaatg    780
gtaatgccgg gtgagaacgt aaccattact gtagaactga ttgcgcctat cgctatggaa    840
gaaggtctgc gctttgcgat tcgcgaaggc ggccgtaccg tgggtgccgg c             891
```

<210> SEQ ID NO 163
<211> LENGTH: 891
<212> TYPE: DNA
<213> ORGANISM: Rickettsia prowazekii

<400> SEQUENCE: 163

```
aatatgataa ctggtgccgc tcagatggat ggtgctatat tagtagtttc tgctgctgat     60
ggtcctatgc ctcaaactag agaacatata ttactggcaa aacaggtagg tgtacctgct    120
atggtagtat ttttgaataa agtagatatg gtagatgatc ctgacctatt agaattagtt    180
gagatggaag taagagaatt attatcaaaa tatggtttcc ctggtaatga aatacctatt    240
attaaaggtt ctgcacttca agctttagaa ggaaaacctg aaggtgaaaa agctattaat    300
gagttaatga atgcagtaga tacgtatata cctcagccta tagagctaca agataaacct    360
tttttaatgc caatagagga tgtattttct atttcaggca gaggtaccgt tgtaactggt    420
agagtggagt caggcataat taaggtgggt gaagaaattg aaatagtagg tctaaaaaat    480
acgcaaaaaa cgacttgtac aggtgtagaa atgttcagaa aattacttga tgaaggacaa    540
tctggagata atgtcggtat attactacgt ggtacaaaaa gagaagaagt agaaagagga    600
caagtacttg caaaacctgg gagcataaaa ccgcatgata aatttgaagc tgaagtgtat    660
gtgcttagta aagaggaagg tggacgtcat accccattta ctaatgatta tcgcccacag    720
ttctatttta gaacaacaga tgttaccggc acaataaaat tgccttctga taagcagatg    780
gttatgcctg gagataatgc tactttttca gtagaattaa ttaagccgat tgctatgcaa    840
gaagggttaa aattctctat acgtgaaggt ggtagaacag taggagccgg t             891
```

<210> SEQ ID NO 164
<211> LENGTH: 891
<212> TYPE: DNA
<213> ORGANISM: Salmonella typhimurium

<400> SEQUENCE: 164

```
aacatgatca ccggtgctgc tcagatggac ggcgcgatcc tggttgttgc tgcgactgac     60
```

```
ggcccgatgc cgcagacccg tgagcacatc ctgctgggtc gtcaggtagg cgttccgtac     120
atcatcgtgt tcctgaacaa atgcgacatg gttgatgacg aagagctgct ggaactggtt     180
gagatggaag ttcgcgaact gctgtctcag tacgacttcc cgggcgacga cactccgatc     240
gttcgtggtt ctgctctgaa agcgctggaa ggcgacgcag agtgggaagc gaaaatcatc     300
gaactggctg gcttcctgga ttcttatatt ccggaaccag agcgtgcgat tgacaagccg     360
ttcctgctgc cgatcgaaga cgtattctcc atctccggtc gtggtaccgt tgttaccggt     420
cgtgtagagc gcggtatcat caaagtgggc gaagaagttg aaatcgttgg tatcaaagag     480
actcagaagt ctacctgtac tggcgttgaa atgttccgca aactgctgga cgaaggccgt     540
gccggtgaga cgtaggtgt tctgctgcgt ggtatcaaac gtgaagaaat cgaacgtggt     600
caggtactgg ctaagccggg caccatcaag ccgcacacca gttcgaatc tgaagtgtac     660 attctgtcca agatgaagg cggccgtcat actccgttct tcaaaggcta ccgtccgcag     720
ttctacttcc gtactactga cgtgactggt accatcgaac tgccgaagg cgtagagatg     780 gtaatgccgg cgacaacat caaaatggtt gttaccctga tccacccgat cgcgatggac     840
gacggtctgc gtttcgcaat ccgtgaaggc ggccgtaccg ttggcgcggg c             891

<210> SEQ ID NO 165
<211> LENGTH: 881
<212> TYPE: DNA
<213> ORGANISM: Shewanella putida

<400> SEQUENCE: 165
atgatcactg gtgctgcaca gatggacggc gcgattctgg tagtcgcttc aacagacggt     60
ccaatgccac agactcgtga gcacatcctg ctttctcgtc aggttggcgt accattcatc     120
atcgtattca tgaacaaatg tgacatggta gatgacgaag agctgttaga gctagttgag     180
atggaagtgc gtgaactgtt atcagaatac gatttcccag gtgatgactt accggtaatc     240
caaggttcag ctctgaaagc gctagaaggc gagccagagt gggaagcaaa atccttgaa     300 ttagcagcgg cgctggattc ttacattcca gaaccacaac gtgacatcga taagccgttc     360
ctactgccaa tcgaagacgt attctcaatt tcaggccgtg gtacagtagt aacaggtcgt     420
gttgagcgtg gtattgtacg cgtaggcgac gaagttgaaa tcgttggtgt acgtgcgaca     480
actaagacaa cgtgtactgg tgtagaaatg ttccgtaaac tgcttgacga aggtcgtgca     540
ggtgagaact gtggtatttt gttacgtggt actaagcgtg atgacgtaga acgtggtcaa     600
gtattagcga agccaggttc aatcaaccca cacactactt ttgaatcaga agtttacgta     660
ctgtcaaaag aagaaggtgg tcgtcacacg ccattcttca aaggctaccg tccacagttc     720
tacttccgta caactgacgt aaccggtact atcgaactgc cagaaggcgt agagatggta     780
atgccaggcg ataacatcaa gatggtagtg acactgattt gcccaatcgc gatggacgaa     840
ggtttacgct tcgcaatccg tgaaggcggt cgtacagtgg t                        881

<210> SEQ ID NO 166
<211> LENGTH: 897
<212> TYPE: DNA
<213> ORGANISM: Stigmatella aurantiaca

<400> SEQUENCE: 166
aacatgatca cgggcgcggc gcagatggac ggagcgattc tggtggtgtc cgcggccgac    60
ggcccgatgc cccagacgcg tgagcacatc ctgctggcca gcaggtggg cgtgccctac   120 atcgtcgtct tcctgaacaa ggtggacatg ctggacgatc cggagctgcg cgagctggtg    180
```

-continued

| | |
|---|---|
| gagatggagg tgcgcgacct gctcaagaag tacgagttcc cgggcgacag catccccatc | 240 |
| atccctggca gcgcgctcaa ggcgctggag ggagacacca gcgacatcgg cgagggagcg | 300 |
| atcctgaagc tgatggcggc ggtggacgag tacatcccga cgccgcagcg tgcgacggac | 360 |
| aagccgttcc tgatgccggt ggaagacgtg ttctccatcg caggccgagg aacggtggcg | 420 |
| acgggccgag tggagcgcgg caagatcaag gtgggcgagg aagtggagat cgtgggatc | 480 |
| cgtccgacgc agaagacggt catcacgggg gtggagatgt ccgcaagct gctggacgag | 540 |
| ggcatggcgg gagacaacat cggagcgctg ctgcgaggcc tgaagcgcga ggacctggag | 600 |
| cgtgggcagg tgctggcgaa ctgggggagc atcaacccgc acacgaagtt caaggcgcag | 660 |
| gtgtacgtgc tgtcgaagga gagggaggg cggcacacgc cgttcttcaa gggataccgg | 720 |
| ccgcagttct acttccggac gacgacgtg accggaacgt gaagctgcc ggacaacgtg | 780 |
| gagatggtga tgccgggaga caacatcgcc atcgaggtgg agctcattac tccggtcgcc | 840 |
| atggagaagg agctgccgtt cgccatccgt gagggtggcc gcacggtggg cgccggc | 897 |

<210> SEQ ID NO 167
<211> LENGTH: 894
<212> TYPE: DNA
<213> ORGANISM: Streptococcus pyogenes

<400> SEQUENCE: 167

| | |
|---|---|
| aacatgatca ctggtgccgc tcaaatggac ggagctatcc ttgtagttgc ttcaactgat | 60 |
| ggaccaatgc cacaaactcg tgagcacatc cttctttcac gtcaggttgg tgttaaacac | 120 |
| cttatcgtgt tcatgaacaa agttgacctt gttgatgacg aagagttgct tgaattagtt | 180 |
| gagatggaaa ttcgtgacct tctttcagaa tacgatttcc caggtgatga ccttccagtt | 240 |
| atccaaggtt cagctcttaa agctcttgaa ggcgacacta aatttgaaga catcatcatg | 300 |
| gaattgatgg atactgttga ttcatacatt ccagaaccag aacgcgacac tgacaaacca | 360 |
| ttgcttcttc cagtcgaaga cgtattctca attacaggtc gtggtacagt tgcttcagga | 420 |
| cgtatcgacc gtggtactgt tcgtgtcaac gacgaaatcg aaatcgttgg tatcaaagaa | 480 |
| gaaactaaaa aagctgttgt tactggtgtt gaaatgttcc gtaaacaact tgacgaaggt | 540 |
| cttgcaggag acaacgtagg tatccttctt cgtggtgttc aacgtgacga atcgaacgt | 600 |
| ggtcaagtta ttgctaaacc aagttcaatc aacccacaca ctaaattcaa aggtgaagta | 660 |
| tatatccttt ctaaagacga aggtggacgt cacactccat tcttcaacaa ctaccgtcca | 720 |
| caattctact tccgtacaac tgacgtaaca ggttcaatcg aacttccagc aggtacagaa | 780 |
| atggttatgc ctggtgataa cgtgacaatc aacgttgagt tgatccaccc aatcgccgta | 840 |
| gaacaaggta ctactttctc aatccgtgaa ggtggacgta ctgttggttc aggt | 894 |

<210> SEQ ID NO 168
<211> LENGTH: 897
<212> TYPE: DNA
<213> ORGANISM: Thiobacillus cuprinus

<400> SEQUENCE: 168

| | |
|---|---|
| aacatgatca ccggtgcggc ccagatggac ggcgccatcc tggtcgtgtc cgccgccgac | 60 |
| ggccccatgc cccaaacccg cgagcacatc ctgctgcgc gtcaggtggg cgtgccctac | 120 |
| atcatcgtgt tcctcaacaa gtgcgacatg gtcgacgacg ccgagctgct cgaactcgtc | 180 |
| gagatggaag tgcgcgagct gctgtccaag tacgacttcc ccggtgacga cacccccatc | 240 |
| atcaagggct cggccaagct ggccctcgaa ggcgacaagg gcgaactggg cgaaggcgcc | 300 |

```
attctcaagc tggccgaggc cctggacacc tacatcccca cgcccgagcg ggccgtcgac    360
ggcgcgttcc tcatgcccgt ggaagacgtg ttctccatct ccgggcgcgg cacggtggtc    420
accgggcgtg tggagcgcgg catcatcaag gtcggcgagg aaatcgagat tgtcggcctc    480
aagcccaccc tcaagaccac ctgcaccggc gtggaaatgt tcaggaagct gctcgaccag    540
ggccaggccg cgacaacgt cggcatcttg ctgcgcggca ccaagcgcga ggaagtcgag    600
cgcggccagg tgctgtgcaa acccggctcg atcaagcccc acacccactt caccgccgag    660
gtgtacgtgc tgagcaagga cgagggcggc cgccacaccc ccttcttcaa caactaccgc    720
ccgcagttct acttccgcac caccgacgtc accggcgcca tcgaactgcc caaggacaag    780
gaaatggtca tgcccggcga taatgtgagc atcaccgtca agctcatcgc ccccatcgcc    840
atggaagaag gcctgcgctt cgccatccgc gaaggcggcc gcaccgtcgg cgccggc      897

<210> SEQ ID NO 169
<211> LENGTH: 894
<212> TYPE: DNA
<213> ORGANISM: Treponema pallidum

<400> SEQUENCE: 169
aatatgatca cgggtgctgc gcagatggac ggtggtattc tcgtcgtgtc tgcgcctgac     60
ggcgttatgc cacagacgaa ggagcatctt ctgctcgccc gtcaggttgg tgttccctcc    120
atcattgttt ttttgaacaa ggttgatttg gttgatgatc ctgagttgct agagctggtg    180
gaagaagagg tgcgtgatgc gcttgctgga tatgggtttt cgcgtgagac gcctatcgtc    240 aagggggtctg cgtttaaagc tctgcaggat ggcgcttccc cggaggatgc agcttgtatt    300
gaggaactgc ttgcggccat ggattcctac tttgaagacc cagtgcgtga cgacgcaaga    360
cctttcttgc tctctatcga ggatgtgtac actatttctg ggcgtggtac cgttgtcacg    420
gggcgcatcg aatgtggggt aattagtctg aatgaagagg tcgagatcgt cgggattaag    480
cccactaaga aaacagtggt tactggcatt gagatgttta ataagttgct tgatcaggga    540
attgcaggtg ataacgtggg gctgcttttg cgcggggtgg ataaaaaaga ggttgagcgc    600
ggtcaggtgc tttctaagcc cggttctatt aagccacaca ccaagtttga ggcgcagatc    660
tacgtgctct ctaaggaaga gggtggccgt cacagtcctt ttttttcaagg ttatcgtccg    720 cagttttatt ttagaactac tgacattacc ggtacgattt ctcttcctga aggggtagac    780
atggtgaagc cggggataa caccaagatt ataggtgagc tcatccaccc gatagctatg    840
gacaagggtc tgaagcttgc gattcgtgaa ggggggcgca ctattgcttc tggt          894

<210> SEQ ID NO 170
<211> LENGTH: 891
<212> TYPE: DNA
<213> ORGANISM: Ureaplasma urealyticum

<400> SEQUENCE: 170
aatatgatta caggggcagc acaaatggat ggagcaattt tagttattgc tgcatctgat     60
ggggttatgg ctcaaactaa agaacatatt ttattagcac gtcaagttgg tgttccaaaa    120
atcgttgttt tcttaaacaa atgtgatttc atgacagatc cagatatgca agatcttgtt    180
gaaatggaag ttcgtgaatt attatctaaa tatgatttg atggcgataa cacaccagtt    240
attcgtggtt caggtcttaa ggctttagaa ggagatccag tttgagaagc aaaaattgat    300
gaattaatgg acgcagttga ttcatgaatt ccattaccag aacgtagtac tgacaaacca    360
ttcttattag caattgaaga tgtattcaca atttcaggac gtggtacagt agtaactgga    420
```

```
cgtgttgaac gtggtgtatt aaaagttaat gatgaggttg aaattgttgg tctaaaagac      480
actcaaaaaa ctgttgttac aggaattgaa atgtttagaa atcattaga tcaagctgaa      540 gctggtgata atgctggtat tttattacgt ggtattaaaa aagaagatgt tgaacgtggt      600
caagtacttg taaaaccagg atcaattaaa cctcaccgta cttttactgc taaagtttat      660
attcttaaaa aagaagaagg tggacgtcat acacctattg tttcaggata ccgtccacaa      720
ttctatttta gaacaacaga tgtaacaggt gctatttcat tacctgctgg tgttgatttg      780
gttatgccag gtgatgacgt tgaaatgact gtagaattaa ttgctccagt tgcgattgaa      840
gatggatcta aattctcaat ccgtgaaggt ggtaaaactg taggtcatgg t                891
```

<210> SEQ ID NO 171
<211> LENGTH: 909
<212> TYPE: DNA
<213> ORGANISM: Wolinella succinogenes

<400> SEQUENCE: 171

```
aacatgatta caggtgctgc tcaaatggat ggcgcgattc ttgttgtttc tgcggcggat       60
ggccccatgc cccaaactag ggagcacatt cttctttctc gacaagtagg cgttccttac      120
atcgtggttt tcttgaacaa agaagatatg gttgatgacg ctgagcttct tgagcttgtt      180
gaaatggaag ttagagaact tcttagcaac tacgacttcc ctggagatga cactcctatc      240
gttgcaggtt ccgctcttaa agctcttgaa gaggctaacg accaggaaaa tgttggcgag      300
tggggcgaga aagtattgaa gcttatggct gaggttgacc gatatattcc tacgcctgag      360
cgagatgtgg ataagccttt ccttatgcct gttgaagacg tattctccat cgcgggtcgt      420
ggaaccgttg tgacaggaag aattgaaaga ggcgtggtta aagtcggtga cgaagtagaa      480
atcgttggta tccgaaacac acaaaaaaca accgtaactg gcgttgagat gttccgaaaa      540
gagctcgaca agggtgaggc gggtgacaac gttggtgttc ttttgagagg caccaagaaa      600
gaagatgttg agagaggtat ggttctttgt aaaataggtt ctatcactcc tcacactaac      660
tttgaaggtg aagtttacgt tctttccaaa gaggaaggcg gacgacacac tccattcttc      720
aatggatacc gacctcagtt ctatgttaga actacagacg ttaccggttc tatctctctt      780
cctgagggcg tagagatggt tatgcctggt gacaacgtta agatcaatgt tgagcttatc      840
gctcctgtag ccctcgaaga gggaacacga ttcgcgatcc gtgaaggtgg tcgaaccgtt      900
ggtgcgggt                                                              909
```

<210> SEQ ID NO 172
<211> LENGTH: 26
<212> TYPE: DNA
<213> ORGANISM: Artificial Sequence
<220> FEATURE:
<223> OTHER INFORMATION: Description of Artificial Sequence: synthetic
      DNA
<220> FEATURE:
<221> NAME/KEY: modified_base
<222> LOCATION: (6)
<223> OTHER INFORMATION: i
<220> FEATURE:
<221> NAME/KEY: modified_base
<222> LOCATION: (12)
<223> OTHER INFORMATION: i
<220> FEATURE:
<221> NAME/KEY: modified_base
<222> LOCATION: (18)
<223> OTHER INFORMATION: i

<400> SEQUENCE: 172

```
tartcngtra angcytcnac rcacat                                              26

<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 173
tctttagcag aacaggatga a                                                   21

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 174
gaataattcc atatcctccg                                                     20
```

US 8,034,588 B2

SPECIES-SPECIFIC, GENUS-SPECIFIC AND UNIVERSAL DNA PROBES AND AMPLIFICATION PRIMERS TO RAPIDLY DETECT AND IDENTIFY COMMON BACTERIAL AND FUNGAL PATHOGENS AND ASSOCIATED ANTIBIOTIC RESISTANCE GENES FROM CLINICAL SPECIMENS FOR DIAGNOSIS IN MICROBIOLOGY LABORATORIES

This application is a continuation of and claims priority to [U.S. patent application Ser. No. 10/753,169, filed Jan. 7, 2004, which is a continuation of] U.S. patent application Ser. No. 09/989,643 filed Nov. 20, 2001, now abandoned, which is a continuation of U.S. patent application Ser. No. 09/297,539, filed on May 3, 1999, now abandoned, which is a National Phase Application of International Patent Application No. PCT/CA97/00829, filed on Nov. 4, 1997, which claims priority to U.S. patent applcation Ser. No. 08/743,637, filed on Nov. 4, 1996, now U.S. Pat. No. 5,994,066.

BACKGROUND OF THE INVENTION

Classical Methods for the Identification and Susceptibility Testing of Bacteria

Bacteria are classically identified by their ability to utilize different substrates as a source of carbon and nitrogen through the use of biochemical tests such as the API20E™ system (bioMérieux). For susceptibility testing, clinical microbiology laboratories use methods including disk diffusion, agar dilution and broth microdilution. Although identifications based on biochemical tests and antibacterial susceptibility tests are cost-effective, at least two days are required to obtain preliminary results due to the necessity of two successive overnight incubations to identify the bacteria from clinical specimens as well as to determine their susceptibility to antimicrobial agents. There are some commercially available automated systems (i.e. the MicroScan system from Dade Diagnostics Corp. and the Vitek system from bioMérieux) which use sophisticated and expensive apparatus for faster microbial identification and susceptibility testing (Stager and Davis, 1992, Clin. Microbiol. Rev. 5:302-327). These systems require shorter incubation periods, thereby allowing most bacterial identifications and susceptibility testing to be performed in less than 6 hours. Nevertheless, these faster systems always require the primary isolation of the bacteria as a pure culture, a process which takes at least 18 hours for a pure culture or 2 days for a mixed culture. The fastest identification system, the autoSCAN-Walk-Away™ system (Dade Diagnostics Corp.) identifies both gram-negative and gram-positive bacterial species from standardized inoculum in as little as 2 hours and gives susceptibility patterns to most antibiotics in 5.5 hours. However, this system has a particularly high percentage (i.e. 3.3 to 40.5%) of non-conclusive identifications with bacterial species other than Enterobacteriaceae (Croizé J., 1995, Lett. Infectiol. 10:109-113; York et al., 1992, J. Clin. Microbiol. 30:2903-2910). For Enterobacteriaceae, the percentage of non-conclusive identifications was 2.7 to 11.4%.

A wide variety of bacteria and fungi are routinely isolated and identified from clinical specimens in microbiology laboratories. Tables 1 and 2 give the incidence for the most commonly isolated bacterial and fungal pathogens from various types of clinical specimens. These pathogens are the most frequently associated with nosocomial and community-acquired human infections and are therefore considered the most clinically important.

Clinical Specimens Test d in Clinical Microbiology Laboratories

Most clinical specimens received in clinical microbiology laboratories are urine and blood samples. At the microbiology laboratory of the Centre Hospitalier de l'Université Laval (CHUL), urine and blood account for approximately 55% and 30% of the specimens received, respectively (Table 3). The remaining 15% of clinical specimens comprise various biological fluids including sputum, pus, cerebrospinal fluid, synovial fluid, and others (Table 3). Infections of the urinary tract, the respiratory tract and the bloodstream are usually of bacterial etiology and require antimicrobial therapy. In fact, all clinical samples received in the clinical microbiology laboratory are tested routinely for the identification of bacteria and susceptibility testing.

Conventional Pathogen Identification from Clinical Specimens

Urine Specimens

The search for pathogens in urine specimens is so preponderant in the routine microbiology laboratory that a myriad of tests have been developed. However, the gold standard remains the classical semi-quantitative plate culture method in which 1 µL of urine is streaked on plates and incubated for 18-24 hours. Colonies are then counted to determine the total number of colony forming units (CFU) per liter of urine. A bacterial urinary tract infection (UTI) is normally associated with a bacterial count of $10^7$ CFU/L or more in urine. However, infections with less than $10^7$ CFU/L in urine are possible, particularly in patients with a high incidence of diseases or those catheterized (Stark and Maki, 1984, N. Engl. J. Med. 311:560-564). Importantly, approximately 80% of urine specimens tested in clinical microbiology laboratories are considered negative (i.e. bacterial count of less than $10^7$ CFU/L; Table 3). Urine specimens found positive by culture are further characterized using standard biochemical tests to identify the bacterial pathogen and are also tested for susceptibility to antibiotics. The biochemical and susceptibility testing normally require 18-24 hours of incubation.

Accurate and rapid urine screening methods for bacterial pathogens would allow a faster identification of negative specimens and a more efficient treatment and care management of patients. Several rapid identification methods (Uriscreen™, UTIscreen™, Flash Track™ DNA probes and others) have been compared to slower standard biochemical methods, which are based on culture of the bacterial pathogens. Although much faster, these rapid tests showed low sensitivities and poor specificities as well as a high number of false negative and false positive results (Koening et al., 1992, J. Clin. Microbiol. 30:342-345; Pezzlo et al., 1992, J. Clin. Microbiol. 30:640-684).

Blood Specimens

The blood specimens received in the microbiology laboratory are always submitted for culture. Blood culture systems may be manual, semi-automated or completely automated. The BACTEC system (from Becton Dickinson) and the BacTAlert system (from Organon Teknika Corporation) are the two most widely used automated blood culture systems. These systems incubate blood culture bottles under optimal conditions for bacterial growth. Bacterial growth is monitored continuously to detect early positives by using highly sensitive bacterial growth detectors. Once growth is detected, a Gram stain is performed directly from the blood culture and then used to inoculate nutrient agar plates. Subsequently, bacterial identification and susceptibility testing are carried out from isolated bacterial colonies with automated systems as described previously. The bottles are normally reported as negative if no growth is detected after an incubation of 6 to 7 days. Normally, the vast majority of blood cultures are reported negative. For example, the percentage of negative blood cultures at the microbiology laboratory of the CHUL for the period February 1994-January 1995 was 93.1% (Table 3).

Other Clinical Samples

Upon receipt by the clinical microbiology laboratory, all body fluids other than blood and urine that are from normally sterile sites (i.e. cerebrospinal, synovial, pleural, pericardial and others) are processed for direct microscopic examination and subsequent culture. Again, most clinical samples are negative for culture (Table 3).

Regarding clinical specimens which are not from sterile sites such as sputum or stool specimens, the laboratory diagnosis by culture is more problematic because of the contamination by the normal flora. The bacterial pathogens potentially associated with the infection are purified from the contaminants and then identified as described previously. Of course, the universal detection of bacteria would not be useful for the diagnosis of bacterial infections at these non sterile sites. On the other hand, DNA-based assays for species or genus detection and identification as well as for the detection of antibiotic resistance genes from these specimens would be very useful and would offer several advantages over classical identification and susceptibility testing methods.

DNA-based Assays with any Clinical Specimens

There is an obvious need for rapid and accurate diagnostic tests for bacterial detection and identification directly from clinical specimens. DNA-based technologies are rapid and accurate and offer a great potential to improve the diagnosis of infectious diseases (Persing et al., 1993, Diagnostic Molecular Microbiology: Principles and Applications, American Society for Microbiology, Washington, D.C.). The DNA probes and amplification primers which are objects of the present invention are applicable for bacterial or fungal detection and identification directly from any clinical specimens such as blood cultures, blood, urine, sputum, cerebrospinal fluid, pus and other type of specimens (Table 3). The DNA-based tests proposed in this invention are superior in terms of both rapidity and accuracy to standard biochemical methods currently used for routine diagnosis from any clinical specimens in microbiology laboratories. Since these tests are performed in around only one hour, they provide the clinicians with new diagnostic tools which should contribute to increase the efficiency of therapies with antimicrobial agents. Clinical specimens from organisms other than humans (e.g. other primates, birds, plants, mammals, farm animals, livestock and others) may also be tested with these assays.

A High Percentage of Culture Negative Specimens

Among all the clinical specimens received for routine diagnosis, approximately 80% of urine specimens and even more (around 95%) for other types of clinical specimens are negative for the presence of bacterial pathogens (Table 3). It would also be desirable, in addition to identify bacteria at the species or genus level in a given specimen, to screen out the high proportion of negative clinical specimens with a test detecting the presence of any bacterium (i.e. universal bacterial detection). Such a screening test may be based on the DNA amplification by PCR of a highly conserved genetic target found in all bacteria. Specimens negative for bacteria would not be amplified by this assay. On the other hand, those that are positive for bacteria would give a positive amplification signal with this assay.

Towards the Development of Rapid DNA-based Diagnostic Tests

A rapid diagnostic test should have a significant impact on the management of infections. DNA probe and DNA amplification technologies offer several advantages over conventional methods for the identification of pathogens and antibiotic resistance genes from clinical samples (Persing et al., 1993, Diagnostic Molecular Microbiology: Principles and Applications, American Society for Microbiology, Washington, D.C.; Ehrlich and Greenberg, 1994, PCR-based Diagnostics in Infectious Disease, Blackwell Scientific Publications, Boston, Mass.). There is no need for culture of the bacterial pathogens, hence the organisms can be detected directly from clinical samples, thereby reducing the time associated with the isolation and identification of pathogens. Furthermore, DNA-based assays are more accurate for bacterial identification than currently used phenotypic identification systems which are based on biochemical tests. Commercially available DNA-based technologies are currently used in clinical microbiology laboratories, mainly for the detection and identification of fastidious bacterial pathogens such as *Mycobacterum tuberculosis*, *Chlamydia trachomatis*, *Neisseria gonorrhoeae* as well as for the detection of a variety of viruses (Podzorski and Persing, Molecular detection and identification of microorganisms, In: P. Murray et al., 1995, Manual of Clinical Microbiology, ASM press, Washington D.C.). There are also other commercially available DNA-based assays which are used for culture confirmation assays.

Others have developed DNA-based tests for the detection and identification of bacterial pathogens which are objects of the present invention: *Staphylococcus* spp. (U.S. Pat. No. 5,437,978), *Neisseria* spp. (U.S. Pat. No. 5,162,199 and European patent publication No. EP 0 337 896 131) and *Listeria monocytogenes* (U.S. Pat. Nos. 5,389,513 and 5,089, 386). However, the diagnostic tests described in these patents are based either on rRNA genes or on genetic targets different from those described in the present invention.

Although there ar diagnostic kits or methods already used in clinical microbiology laboratories, there is still a need for an advantageous alternative to the conventional culture identification methods in order to improve the accuracy and the speed of the diagnosis of commonly encountered bacterial infections. Besides being much faster, DNA-based diagnostic tests are more accurate than standard biochemical tests presently used for diagnosis because the bacterial genotype (e.g. DNA level) is more stable than the bacterial phenotype (e.g. metabolic level).

Knowledge of the genomic sequences of bacterial and fungal species continuously increases as testified by the number of sequences available from databases. From the sequences readily available from databases, there is no indication therefrom as to their potential for diagnostic purposes. For determining good candidates for diagnostic purposes, one could select sequences for DNA-based assays for (i) the species-specific detection and identification of commonly encountered bacterial or fungal pathogens, (ii) the genus-specific detection and identification of commonly encountered bacterial or fungal pathogens, (iii) the universal detection of bacterial or fungal pathogens and/or (iv) the specific detection and identification of antibiotic resistance genes. All of the above types of DNA-based assays may be performed directly from any type of clinical specimens or from a microbial culture.

In WO 96/08502 patent publication, we described DNA sequences suitable for (i) the species-specific detection and identification of 12 clinically important bacterial pathogens, (ii) the universal detection of bacteria, and (iii) the detection of 17 antibiotic resistance genes. This co-pending application described proprietary DNA sequences and DNA sequences selected from databases (in both cases, fragments of at least 100 base pairs), as well as oligonucleotide probes and amplification primers derived from these sequences. All the nucleic acid sequences described in this patent application enter the composition of diagnostic kits and methods capable of a) detecting the presence of bacteria, b) detecting specifically the presence of 12 bacterial species and 17 antibiotic resistance genes. However, these methods and kits need to be improved, since the ideal kit and method should be capable of diagnosing close to 100% of microbial pathogens and antibiotic resistance genes. For example, infections caused by *Enterococcus faecium* have become a clinical problem because of its resistance to many antibiotics. Both the detection of these bacteria and the evaluation of their resistance profiles are desirable. It is, worthwhile noting that the French patent publication FR-A-2,699,539 discloses the sequence of vancomycin B gene, which gene may be derived from *Enterococcus faecium* strains resistant to this antibiotic. Besides that, novel DNA sequences (probes and primers) capable of recognizing the same and other microbial pathogens or the same and additional antibiotic resistance genes are also desirable to aim at detecting more target genes and complement our earlier patent application.

STATEMENT OF THE INVENTION

It is an object of the present invention to provide a specific, ubiquitous and sensitive method using probes and/or amplification primers for determining the presence and/or amount of nucleic acids:
from specific microbial species or genera selected from the group consisting of *Streptococcus* species, *Streptococcus agalactiae, Staphylococcus* species, *Staphylococcus saprophyticus, Enterococcus* species, *Enterococcus faecium, Neisseria* species, *Neisseria meningitidis, Listeria monocytogenes, Candida* species and *Candida albicans*
from an antibiotic resistance gene selected from the group consisting of $bla_{tem}$, $bla_{rob}$, $bla_{shv}$, $bla_{oxa}$, blaZ, aadB, aacC1, aacC2, aacC3, aacA4, aac6'-lla, ermA, ermnB, ermC, mecA, vanA, vanB, vanC, satA, aac(6')-aph(2''), aad(6'), vat, vga, msrA, sul and int, and optionally,
from any bacterial species
in any sample suspected of containing said nucleic acids, wherein each of said nucleic acids or a variant or part thereof comprises a selected target region hybridizable with said probe or primers;
said method comprising the steps of contacting said sample with said probes or primers and detecting the presence and/or amount of hybridized probes or amplified products as an indication of the presence and/or amount of said any bacterial species, specific microbial species or genus and antibiotic resistance gene.

In a specific embodiment, a similar method directed to each specific microbial species or genus detection and identification, antibiotic resistance genes detection, and universal bacterial detection, separately, is provided.

In a more specific embodiment, the method makes use of DNA fragments (proprietary fragments and fragments obtained from databases), selected for their capacity to sensitively, specifically and ubiquitously detect the targeted bacterial or fungal nucleic acids.

In a particularly preferred embodiment, oligonucleotides of at least 12 nucleotides in length have been derived from the longer DNA fragments, and are used in the present method as probes or amplification primers.

The proprietary oligonucleotides (probes and primers) are also another object of the invention.

Diagnostic kits comprising probes or amplification primers for the detection of a microbial species or genus selected from the group consisting of *Streptococcus* species, *Streptococcus agalactiae, Staphylococcus* species, *Staphylococcus saprophyticus, Enterococcus* species, *Enterococcus faecium, Neisseria* species, *Neisseria meningitidis, Listeria monocytogenes, Candida* species and *Candida albicans* are also objects of the present invention.

Diagnostic kits further comprising probes or amplification primers for the detection of an antibiotic resistance gene selected from the group consisting of $bla_{tem}$, $bla_{rob}$, $bla_{shv}$, $bla_{oxa}$, blaZ, aadB, aacC1, aacC2, aacC3, aacA4, aac6'-lla, ermA, ermB, ermC, mecA, vanA, vanB, vanC, satA, aac(6')-aph(2''), aad(6'), vat, vga, msrA, sul and int are also objects of this invention.

Diagnostic kits further comprising probes or amplification primers for the detection of any bacterial or fungal species, comprising or not comprising those for the detection of the specific microbial species or genus listed above, and further comprising or not comprising probes and primers for the antibiotic resistance genes listed above, are also objects of this invention.

In a preferred embodiment, such a kit allows for the separate or the simultaneous detection and identification of the above-listed microbial species or genus, antibiotic resistance genes and for the detection of any bacterium.

In the above methods and kits, amplification reactions may include a) polymerase chain reaction (PCR), b) ligase chain reaction, c) nucleic acid sequence-based amplification, d) self-sustained sequence replication, e) strand displacement amplification, f) branched DNA signal amplification, g) transcription-mediated amplification, h) cycling probe technology (CPT) i) nested PCR, or j) multiplex PCR.

In a preferred embodiment, a PCR protocol is used as an amplification reaction.

In a particularly preferred embodiment, a PCR protocol is provided, comprising, for each amplification cycle, an annealing step of 30 seconds at 45-55° C. and a denaturation step of only one second at 95° C., without any time allowed specifically for the elongation step. This PCR protocol has been standardized to be suitable for PCR reactions with all selected primer pairs, which greatly facilitates the testing because each clinical sample can be tested with universal, species-specific, genus-specific and antibiotic resistance gene PCR primers under uniform cycling conditions. Furthermore, various combinations of primer pairs may be used in multiplex PCR assays.

We aim at developing a rapid test or kit to discard rapidly all the samples which are negative for bacterial cells and to subsequently detect and identify the above bacterial and/or fungal species and genera and to determine rapidly the bacterial resistance to antibiotics. Although the sequences from the selected antibiotic resistance genes are available from databases and have been used to develop DNA-based tests for their detection, our approach is unique because it represents a major improvement over current gold standard diagnostic methods based on bacterial cultures. Using an amplification method for the simultaneous bacterial detection and identification and antibiotic resistance genes detection, there is no need for culturing the clinical sample prior to testing. Moreover, a modified PCR protocol has been developed to detect all target DNA sequences in approximately one hour under uniform amplification conditions. This procedure will save lives by optimizing treatment, will diminish antibiotic resistance because less antibiotics will be prescribed, will reduce the use of broad spectrum antibiotics which are expensive, decrease overall health care costs by preventing or shortening hospitalizations, and decrease the time and costs associated with clinical laboratory testing.

In the methods and kits described herein below, the oligonucleotide probes and amplification primers have been derived from larger sequences (i.e. DNA fragments of at least 100 base pairs). All DNA fragments have been obtained either from proprietary fragments or from databases. DNA fragments selected from databases are newly used in a method of detection according to the present invention, since they have been selected for their diagnostic potential.

It is clear to the individual skilled in the art that other oligonucleotide sequences appropriate for (i) the universal bacterial detection, (ii) the detection and identification of the above microbial species or genus and (iii) the detection of antibiotic resistance genes other than those listed in Annex VI may also be derived from the proprietary fragments or selected database sequences. For example, the oligonucleotide primers or probes may be shorter or longer than the ones we have chosen; they may also be selected anywhere else in the proprietary DNA fragments or in the sequences selected from databases; they may be also variants of the same oligonucleotide. If the target DNA or a variant thereof hybridizes to a given oligonucleotide, or if the target DNA or a variant thereof can be amplified by a given oligonucleotide PCR primer pair, the converse is also true; a given target DNA may hybridize to a variant oligonucleotide probe or be amplified by a variant oligonucleotide PCR primer. Alternatively, the oligonucleotides may be designed from any DNA fragment sequences for use in amplification methods other than PCR. Consequently, the core of this invention is the identification of universal, species-specific, genus-specific and resistance gene-specific genomic or non-genomic DNA fragments which are used as a source of specific and ubiquitous oligonucleotide probes and/or amplification primers. Although the selection and evaluation of oligonucleotides suitable for diagnostic purposes requires much effort, it is quite possible for the individual skilled in the art to derive, from the selected DNA fragments, oligonucleotides other than the ones listed in Annex VI which are suitable for diagnostic purposes. When a proprietary fragment or a database sequence is selected for its specificity and ubiquity, it increases the probability that subsets thereof will also be specific and ubiquitous.

Since a high percentage of clinical specimens are negative for bacteria (Table 3), DNA fragments having a high potential for the selection of universal oligonucleotide probes or primers were selected from proprietary and database sequences. The amplification primers were selected from a gene highly conserved in bacteria and fungi, and are used to detect the presence of any bacterial pathogen in clinical specimens in order to determine rapidly (approximately one hour) whether it is positive or negative for bacteria. The selected gene, designated tuf, encodes a protein (EF-Tu) involved in the translational process during protein synthesis. The tuf gene sequence alignments used to derive the universal primers include both proprietary and database sequences (Example 1 and Annex I). This strategy allows the rapid screening of the numerous negative clinical specimens (around 80% of the specimens received, see Table 3) submitted for bacteriological testing. Tables 4, 5 and 6 provide a list of the bacterial or fungal species used to test the specificity of PCR primers and DNA probes. Table 7 gives a brief description of each species-specific, genus-specific and universal amplification assays which are objects of the present invention. Tables 8, 9 and 10 provide some relevant information about the proprietary and database sequences selected for diagnostic puposes.

DETAILED DESCRIPTION OF THE INVENTION

Development of Species-Specific, Genus-Specific, Universal and Antibiotic Resistance Gene-Specific DNA Probes and Amplification Primers for Microorganisms
Selection from Databases of Sequences Suitable for Diagnostic Purposes In order to select sequences which are suitable for species-specific or genus-specific detection and identification of bacteria or fungi or, alternatively, for the universal detection of bacteria, the database sequences (GenBank, EMBL and Swiss-Prot) were chosen based on their potential for diagnostic purposes according to sequence information and computer analysis performed with these sequences. Initially, all sequence data available for the targeted microbial species or genus were carefully analyzed. The gene sequences which appeared the most promising for diagnostic purposes based on sequence information and on sequence comparisons with the corresponding gene in other microbial species or genera performed with the Genetics Computer Group (GCG, Wisconsin) programs were selected for testing by PCR. Optimal PCR amplification primers were chosen from the selected database sequences with the help of the Oligo™ 4.0 primer analysis software (National Biosciences Inc., Plymouth, Minn.). The chosen primers were tested in PCR assays for their specificity and ubiquity for the target microbial species or genus. In general, the identification of database sequences from which amplification primers suitable for species-specific or genus-specific detection and identification were selected involved the computer analysis and PCR testing of several candidate gene sequences before obtaining a primer pair which is specific and ubiquitous for the target microbial species or genus. Annex VI provides a list of selected specific and ubiquitous PCR primer pairs. Annexes I to V and Examples 1 to 4 illustrate the strategy used to select genus-specific, species-specific and universal PCR primers from tuf sequences or from the recA gene.

Oligonucleotide Primers and Probes Design and Synthesis

The DNA fragments sequenced by us or selected from databases (GenBank and EMBL) were used as sources of oligonucleotides for diagnostic purposes. For this strategy, an array of suitable oligonucleotide primers or probes derived from a variety of genomic DNA fragments (size of more than 100 bp) selected from databases were tested for their specificity and ubiquity in PCR and hybridization assays as described later. It is important to note that the database sequences were selected based on their potential for being species-specific, genus-specific or universal for the detection of bacteria or fungi according to available sequence information and extensive analysis and that, in general, several candidate database sequences had to be tested in order to obtain the desired specificity, ubiquity and sensitivity.

Oligonucleotide probes and amplification primers derived from species-specific fragments selected from database sequences were synthesized using an automated DNA synthesizer (Perkin-Elmer Corp., Applied Biosystems Division). Prior to synthesis, all oligonucleotides (probes for hybridization and primers for DNA amplification) were evaluated for their suitability for hybridization or DNA amplification by polymerase chain reaction (PCR) by computer analysis using standard programs (i.e. the Genetics Computer Group (GCG) programs and the primer analysis software Oligo™ 4.0). The potential suitability of the PCR primer pairs was also evaluated prior to the synthesis by verifying the absence of unwanted features such as long stretches of one nucleotide and a high proportion of G or C residues at the 3' end (Persing et al., 1993, Diagnostic Molecular Microbiology: Principles and Applications, American Society. for Microbiology, Washington, D.C.).

The oligonucleotide primers or probes may be derived from either strand of the duplex DNA. The primers or probes may consist of the bases A, G, C, or T or analogs and they may be degenerated at one or more chosen nucleotide position(s). The primers or probes may be of any suitable length and may be selected anywhere within the DNA sequences from proprietary fragments or from selected database sequences which are suitable for (i) the universal detection of bacteria, (ii) the species-specific detection and identification of *Enterococcus faecium, Listeria monocytogenes, Neissedia meningitidis, Staphylococcus saprophyticus, Streptococcus agalactiae* and *Candida albicans* (iii) the genus-specific detection of *Streptococcus* species, *Enterococcus* species, *Staphylococcus* species and *Neisseria* species or (iv) the detection of the 26 above-mentioned clinically important antibiotic resistance genes.

Variants for a given target bacterial gene are naturally occurring and are attributable to sequence variation within that gene during evolution (Watson et al., 1987, Molecular Biology of the Gene, $4^{th}$ ed., The Benjamin/Cummings Publishing Company, Menlo Park, Calif.; Lewin, 1989, Genes IV, John Wiley & Sons, New York, N.Y.). For example, different strains of the same bacterial species may have a single or more nucleotide variation(s) at the oligonucleotide hybridization site. The person skilled in the art is well aware of the existence of variant bacterial or fungal DNA sequences for a specific gene and that the frequency of sequence variations depends on the selective pressure during evolution on a given gene product. The detection of a variant sequence for a region between two PCR primers may be demonstrated by sequencing the amplification product. In order to show the presence of sequence variants at the primer hybridization site, one has to amplify a larger DNA target with PCR primers outside that hybridization site. Sequencing of this larger fragment will allow the detection of sequence variation at this site. A similar strategy may be applied to show variants at the hybridization site of a probe. Insofar as the divergence of the target sequences or a part thereof does not affect the specificity and ubiquity of the amplification primers or probes, variant bacterial DNA is under the scope of this invention. Variants of the selected primers or probes may also be used to amplify or hybridize to a variant DNA.

Sequencing of Tuf Sequences from a Variety of Bacterial and Fungal Species

The nucleotide sequence of a portion of tuf genes was determined for a variety of bacterial and fungal species. The amplification primers SEQ ID NOs: 107 and 108, which amplify a tuf gene portion of approximately 890 bp, were used for the sequencing of bacterial tuf sequences. The amplification primers SEQ ID NOs: 109 and 172, which amplify a tuf gene portion of approximately 830 bp, were used for the sequencing of fungal tuf sequences. Both primer pairs can amplify tufA and tufB genes. This is not surprising because these two genes are nearly identical. For example, the entire tufA and tufB genes from *E. coli* differ at only 13 nucleotide positions (Neidhardt et al., 1996, *Escherichia coli* and Salmonella: Cellular and Molecular Biology, $2^{nd}$ ed., American Society for Microbiology Press, Washington, D.C.). These amplification primers are degenerated at several nucleotide positions and contain inosines in order to allow the amplification of a wide range of tuf sequences. The strategy used to select these amplification primers is similar to that illustrated in Annex I for the selection of universal primers. The amplification primers SEQ ID NOs: 107 and 108 could be used to amplify the tuf genes from any bacterial species. The amplification primers SEQ ID NOs: 109 and 172 could be used to amplify the tuf genes from any fungal species.

The tuf genes were amplified directly from bacterial or yeast cultures using the following amplification protocol: One μL of cell suspension was transferred directly to 19 μL of a PCR reaction mixture containing 50 mM KCl, 10 mM Tris-HCl (pH 9.0), 0.1% Triton X-100, 2.5 mM $MgCl_2$, 1 μM of each of the 2 primers, 200 μM of each of the four dNTPs, 0.5 unit of Taq DNA polymerase (Promega Corp., Madison, Wis.). PCR reactions were subjected to cycling using a MJ Research PTC-200 thermal cycler (MJ Research Inc., Watertown, Mass.) as follows: 3 min at 96° C. followed by 30-35 cycles of 1 min at 95° C. for the denaturation step, 1 min at 30-50° C. for the annealing step and 1 min at 72° C. for the extension step. Subsequently, twenty microliters of the PCR-amplified mixture were resolved by electrophoresis in a 1.5% agarose gel. The gel was then visualized by staining with methylene blue (Flores et al., 1992, Biotechniques, 13:203-205). The size of the amplification products was estimated by comparison with a 100-bp molecular weight ladder. The band corresponding to the specific amplification product (i.e. approximately 890 or 830 bp for bacterial or fungal tuf sequences, respectively) was excised from the agarose gel and purified using the QIAquick™ gel extraction kit (QIAGEN Inc., Chatsworth, Calif.). The gel-purified DNA fragment was then used directly in the sequencing protocol. Both strands of the tuf genes amplification product were sequenced by the dideoxynucleotide chain termination sequencing method by using an Applied Biosystems automated DNA sequencer (model 373A) with their PRISM™ Sequenase® Terminator Double-stranded DNA Sequencing Kit (Perkin-Elmer Corp., Applied Biosystems Division, Foster City, Calif.). The sequencing reactions were all performed by using the amplification primers (SEQ ID NOs: 107 to 109 and 172) and 100 ng per reaction of the gel-purified amplicon. In order to ensure that the determined sequence did not contain errors attributable to the sequencing of PCR artefacts, we have sequenced two preparations of the gel-purified tuf amplification product originating from two independent PCR amplifications. For all target microbial species, the sequences determined for both amplicon preparations were identical. Furthermore, the sequences of both strands were 100% complementary thereby confirming the high accuracy of the determined sequence. The tuf sequences determined using the above strategy are all in the Sequence Listing (i.e. SEQ ID NOs:118 to 146). Table 13 gives the originating microbial species and the source for each tuf sequence in the Sequence Listing.

The alignment of the tuf sequences determined by us or selected from databases reveals clearly that the length of the sequenced portion of the tuf genes is variable. There may be insertions or deletions of several amino acids. This explains why the size of the sequenced tuf amplification product was variable for both bacterial and fungal species. Among the tuf sequences determined by our group, we found insertions and deletions adding up to 5 amino acids or 15 nucleotides. Consequently, the nucleotide positions indicated on top of each of Annexes I to V do not correspond for tuf sequences having insertions or deletions.

It should also be noted that the various tuf sequences determined by us occasionally contain degenerescences. These degenerated nucleotides correspond to sequence variations between tufA and tufB genes because the amplification primers amplify both tuf genes. These nucleotide variations were not attributable to nucleotide misincorporations by the taq DNA polymerase because the sequence of both strands were identical and also because the sequences determined with both preparations of the gel-purified tuf amplicons were identical.

The Selection of Amplification Primers from tuf Sequences

The tuf sequences determined by us or selected from databases were used to select PCR primers for (i) the universal detection of bacteria, (ii) the genus-specific detection and identification of *Enterococcus* spp. and *Staphylococcus* spp. and (iii) the species-specific detection and identification of *Candida albicans*. The strategy used to select these PCR primers was based on the analysis of multiple sequence alignments of various tuf sequences. For more details about the selection of PCR primers from tuf sequences, please refer to Examples 1 to 3 and Annexes I to IV.

The Selection of Amplification Primers from recA

The comparison of the nucleotide sequence for the recA gene from various bacterial species including 5 species of streptococci allowed the selection of Streptococcus-specific PCR primers. For more details about the selection of PCR primers from recA, please refer to Example 4 and Annex V.

DNA Fragment Isolation from Staphylococcus Saprophyticus by Arbitrarily Primed PCR DNA sequences of unknown coding potential for the species-specific detection and identification of *Staphylococcus saprophyticus* were obtained by the method of arbitrarily primed PCR (AP-PCR).

AP-PCR is a method which can be used to generate specific DNA probes for microorganisms (Fani et al., 1993, Mol. Ecol. 2:243-250). A description of the AP-PCR protocol used to isolate a species-specific genomic DNA fragment from *Staphylococcus saprophyticus* follows. Twenty different oligonucleotide primers of 10 nucleotides in length (all included in the AP-PCR kit OPAD (Operon Technologies, Inc., Alameda, Calif.)) were tested systematically with DNAs from 3 bacterial strains of *Staphylococcus saprophyticus* (all obtained from the American Type Culture Collection (ATCC): numbers 15305, 35552 and 43867) as well as with DNA from four other staphylococcal species (*Staphylococcus aureus* ATCC 25923, *Staphylococcus epidermidis* ATCC 14990, *Staphylococcus haemolyticus* ATCC 29970 and *Staphylococcus hominis* ATCC 35982). For all bacterial species, amplification was performed from a bacterial suspension adjusted to a standard 0.5 McFarland which corresponds to approximately $1.5 \times 10^8$ bacteria/mL. One µL of the standardized bacterial suspension was transferred directly to 19 µL of a PCR reaction mixture containing 50 mM KCl, 10 mM Tris-HCl (pH 9.0), 0.1% Triton X-100, 2.5 mM $MgCl_2$, 1.2 µM of only one of the 20 different AP-PCR primers OPAD, 200 µM of each of the four dNTPs and 0.5 unit of Taq DNA polymerase (Promega Corp., Madison, Wis.). PCR reactions were subjected to cycling using a MJ Research PTC-200 thermal cycler (MJ Research Inc.) as follows: 3 min at 96° C. followed by 35 cycles of 1 min at 95° C. for the denaturation step, 1 min at 32° C. for the annealing step and 1 min at 72° C. for the extension step. A final extension step of 7 min at 72° C. was made after the 35 cycles to ensure complete extension of PCR products. Subsequently, twenty microliters of the PCR amplified mixture were resolved by electrophoresis in a 2% agarose gel containing 0.25 µg/mL of ethidium bromide. The size of the amplification products was estimated by comparison with a 50-bp molecular weight ladder.

Amplification patterns specific for *Staphylococcus saprophyticus* were observed with the AP-PCR primer OPAD-9 (SEQ ID NO: 25). Amplification with this primer consistently showed a band corresponding to a DNA fragment of approximately 450bp for all *Staphylococcus saprophyticus* strains tested but not for any of the four other staphylococcal species tested. This species-specific pattern was confirmed by testing 10 more clinical isolates of *S. saprophyticus* selected from the culture collection of the microbiology laboratory of the CHUL as well as strains selected from the gram-positive bacterial species listed in Table 5.

The band corresponding to the approximately 450 bp amplicon which was specific and ubiquitous for *S. saprophyticus* based on AP-PCR was excised from the agarose gel and purified using the QIAquick™ gel extraction kit (QIAGEN Inc.). The gel-purified DNA fragment was cloned into the T/A cloning site of the pCR 2.1™ plasmid vector (Invitrogen Inc.) using T4 DNA ligase (New England BioLabs). Recombinant plasmids were transformed into *E. coli* DH5α competent cells using standard procedures. Plasmid DNA isolation was done by the method of Birnboim and Doly (Nucleic Acids Res. 7:1513-1523) for small-scale preparations. All plasmid DNA preparations were digested with the EcoRI restriction endonuclease to ensure the presence of the approximately 450 bp AP-PCR insert into the recombinant plasmids. Subsequently, a large-scale and highly purified plasmid DNA preparation was performed from two selected clones shown to carry the AP-PCR insert by using the QIAGEN plasmid purification kit. These plasmid preparations were used for automated DNA sequencing.

Both strands of the AP-PCR insert from the two selected clones were sequenced by the dideoxynucleotide chain termination sequencing method with SP6 and T7 sequencing primers, by using an Applied Biosystems automated DNA sequencer as described previously. The analysis of the obtained sequences revealed that the DNA sequences for both strands from each clone were 100% complementary. Furthermore, it showed that the entire sequence determined for each clone were both identical. These sequencing data confirm the 100% accuracy for the determined 438bp sequence (SEQ ID NO: 29). Optimal amplification primers have been selected from the sequenced AP-PCR *Staphylococcus saprophyticus* DNA fragment with the help of the primer analysis software Oligom™ 4.0. The selected primer sequences have been tested in PCR assays to verify their specificity and ubiquity (Table 7). These PCR primers were specific since there was no amplification with DNA from bacterial species other than *S. saprophyticus* selected from Tables 4 and 5. Furthermore, this assay was ubiquitous since 245 of 260 strains of *S. saprophyticus* were efficiently amplified with this PCR assay. When used in combination with another *S. saprophyticus*-specific PCR assay, which is an object of our co-pending U.S. (Ser. No. 08/526,840) and PCT (PCT/CA/95/00528) patent applications, the ubiquity reaches 100% for these 260 strains.

DNA Amplification

For DNA amplification by the widely used PCR (polymerase chain reaction) method, primer pairs were derived from proprietary DNA fragments or from database sequences. Prior to synthesis, the potential primer pairs were analyzed by using the Oligo™ 4.0 software to verify that they are good candidates for PCR amplification.

During DNA amplification by PCR, two oligonucleotide primers binding respectively to each strand of the heat-denatured target DNA from the bacterial genome are used to amplify exponentially in vitro the target DNA by successive thermal cycles allowing denaturation of the DNA, annealing of the primers and synthesis of new targets at each cycle (Persing et al, 1993, Diagnostic Molecular Microbiology: Principles and Applications, American Society for Microbiology, Washington, D.C.).

Briefly, the PCR protocols were as follow: Treated clinical specimens or standardized bacterial or fungal suspensions (see below) were amplified in a 20 µL PCR reaction mixture containing 50 mM KCl, 10 mM Tris-HCl (pH 9.0), 2.5 mM MgCl$_2$, 0.4 µM of each primer, 200 µM of each of the four dNTPs and 0.5 unit of Taq DNA polymerase (Promega) combined with the TaqStar™ antibody (Clontech Laboratories Inc., Palo Alto, Calif.). The TaqStar™ antibody, which is a neutralizing monoclonal antibody to Taq DNA polymerase, was added to all PCR reactions to enhance the specificity and the sensitivity of the amplifications (Kellogg et al., 1994, Biotechniques 16:1134-1137). The treatment of the clinical specimens varies with the type of specimen tested, since the composition and the sensitivity level required are different for each specimen type. It consists in a rapid protocol to lyse the bacterial cells and eliminate the PCR inhibitory effects (see example 11 for urine specimen preparation). For amplification from bacterial or fungal cultures, the samples were added directly to the PCR amplification mixture without any pretreatment step (see example 10). Primer sequences derived from highly conserved regions of the bacterial 16S ribosomal RNA gene were used to provide an internal control for all PCR reactions. Alternatively, the internal control was derived from sequences not found in microorganisms or in the human genome. The internal control was integrated into all amplification reactions to verify the efficiency of the PCR assays and to ensure that significant PCR inhibition was absent. The internal control derived from rRNA was also useful to monitor the efficiency of bacterial lysis protocols.

PCR reactions were then subjected to thermal cycling (3 min at 95° C. followed by 30 cycles of 1 second at 95° C. for the denaturation step and 30 second at 55° C. for the annealing-extension step) using a PTC-200 thermal cycler (MJ Research Inc.) and subsequently analyzed by standard ethidium bromide-stained agarose gel electrophoresis. The number of cycles performed for the PCR assays varies according to the sensitivity level required. For example, the sensitivity level required for microbial detection directly from clinical specimens is higher for blood specimens than for urine specimens because the concentration of microorganisms associated with a septicemia can be much lower than that associated with a urinary tract infection. Consequently, more sensitive PCR assays having more thermal cycles are required for direct detection from blood specimens. Similarly, PCR assays performed directly from bacterial or fungal cultures may be less sensitive than PCR assays performed directly from clinical specimens because the number of target organisms is normally much lower in clinical specimens than in microbial cultures.

It is clear that other methods for the detection of specific amplification products, which may be faster and more practical for routine diagnosis, may be used. Such methods may be based on the detection of fluorescence after amplification (e.g. TaqMan™ system from Perkin Elmer or Amplisensor™ from Biotronics). Methods based on the detection of fluorescence are particularly promising for utilization in routine diagnosis as they are very rapid, quantitative and can be automated (Example 14).

Microbial pathogens detection and identification may also be performed by solid support or liquid hybridization using species-specific internal DNA probes hybridizing to an amplification product. Such probes may be generated from any species-specific or genus-specific DNA amplification products which are objects of the present invention. Alternatively, the internal probes for species or genus detection and identification may be derived from the amplicons produced by the universal amplification assay. The oligonucleotide probes may be labeled with biotin or with digoxigenin or with any other reporter molecules.

To assure PCR efficiency, glycerol, dimethyl sulfoxide (DMSO) or other related solvents can be used to increase the sensitivity of the PCR and to overcome problems associated with the amplification of a target DNA having a high GC content or forming strong secondary structures (Dieffenbach and Dveksler, 1995, PCR Primer: A Laboratory Manual, Cold Spring Harbor Laboratory Press, Plainview, N.Y.). The concentration ranges for glycerol and DMSO are 5-15% (v/v) and 3-10% (v/v), respectively. For the PCR reaction mixture, the concentration ranges for the amplification primers and MgCl$_2$ are 0.1-1.5 µM and 1.5-3.5 mM, respectively. Modifications of the standard PCR protocol using external and nested primers (i.e. nested PCR) or using more than one primer pair (i.e. multiplex PCR) may also be used (Persing et al., 1993, Diagnostic Molecular Microbiology: Principles and Applications, American Society for Microbiology, Washington, D.C.). For more details about the PCR protocols and amplicon detection methods, see Examples 9 to 14.

The person skilled in the art of DNA amplification knows the existence of other rapid amplification procedures such as ligase chain reaction (LCR), transcription-mediated amplification (TMA), self-sustained sequence replication (3SR), nucleic acid sequence-based amplification (NASBA), strand displacement amplification (SDA), branched DNA (bDNA) and cycling probe technology (CPT) (Lee et al., 1997, Nucleic Acid Amplification Technologies: Application to Disease Diagnosis, Eaton Publishing, Boston, Mass.; Persing et al., 1993, Diagnostic Molecular Microbiology: Principles and Applications, American Society for Microbiology, Washington, D.C.). The scope of this invention is not limited to the use of amplification by PCR, but rather includes the use of any rapid nucleic acid amplification method or any other procedure which may be used to increase rapidity and sensitivity of the tests. Any oligonucleotide suitable for the amplification of nucleic acids by approaches other than PCR and derived from the species-specific, genus-specific and universal DNA fragments as well as from selected antibiotic resistance gene sequences included in this document are also under the scope of this invention.

Hybridization Assays with Oligonucleotide Probes

In hybridization experiments, single-stranded oligonucleotides (size less than 100 nucleotides) have some advantages over DNA fragment probes for the detection of bacteria, such as ease of synthesis in large quantities, consistency in results from batch to batch and chemical stability. Briefly, for the hybridizations, oligonucleotides were 5' end-labeled with the radionucleotide γ-$^{32}$P(dATP) using T4 polynucleotide kinase (Pharmacia) (Sambrook et al., 1989, Molecular Cloning: A Laboratory Manual, 2$^{nd}$ ed., Cold Spring Harbor Laboratory Press, Cold Spring Harbor, N.Y.). The unincorporated radionucleotide was removed by passing the labeled oligonucleotide through a Sephadex G-50™ column. Alternatively, oligonucleotides were labeled with biotin, either enzymatically at their 3' ends or incorporated directly during synthesis at their 5' ends, or with digoxigenin. It will be appreciated by the person skilled in the art that labeling means other than the three above labels may be used.

Each oligonucleotide probe was then tested for its specificity by hybridization to DNAs from a variety of bacterial and fungal species selected from Tables 4, 5 and 6. All of the bacterial or fungal species tested were likely to be pathogens associated with common infections or potential contaminants which can be isolated from clinical specimens. Each target DNA was released from bacterial cells using standard chemical treatments to lyse the cells (Sambrook et al., 1989, Molecular Cloning: A Laboratory Manual, 2$^{nd}$ ed., Cold Spring Harbor Laboratory Press, Cold Spring Harbor, N.Y.).

Subsequently, the DNA was denatured by conventional methods and then irreversibly fixed onto a solid support (e.g. nylon or nitrocellulose membranes) or free in solution. The fixed single-stranded target DNAs were then hybridized with the oligonucleotide probe cells (Sambrook et al., 1989, Molecular Cloning: A Laboratory Manual, $2^{nd}$ ed., Cold Spring Harbor Laboratory Press, Cold Spring Harbor, N.Y.). Pre-hybridization conditions were in 1 M NaCl+10% dextran sulfate+ 1% SDS+100 μg/mL salmon sperm DNA at 65° C. for 15 min. Hybridization was performed in fresh pre-hybridization solution containing the labeled probe at 65° C. overnight. Post-hybridization washing conditions were as follows: twice in 3×SSC containing 1% SDS, twice in 2×SSC containing 1% SDS and twice in 1×SSC containing 1% SDS (all of these washes were at 65° C. for 15 min), and a final wash in 0.1×SSC containing 1% SDS at 25° C. for 15 min. Autoradiography of washed filters allowed the detection of selectively hybridized probes. Hybridization of the probe to a specific target DNA indicated a high degree of similarity between the nucleotide sequence of these two DNAs because of the high stringency of the washes.

An oligonucleotide probe was considered specific only when it hybridized solely to DNA from the species or genus from which it was isolated. Oligonucleotide probes found to be specific were subsequently tested for their ubiquity (i.e. ubiquitous probes recognized most or all isolates of the target species or genus) by hybridization to microbial DNAs from clinical isolates of the species or genus of interest including ATCC strains. The DNAs from strains of the target species or genus were denatured, fixed onto nylon membranes and hybridized as described above. Probes were considered ubiquitous when they hybridized specifically with the DNA from at least 80% of the isolates of the target species or genus.

Specificity and Ubiquity Tests for Oligonucleotide Primers and Probes

The specificity of oligonucleotide primers and probes, derived either from the DNA fragments sequenced by us or selected from databases, was tested by amplification of DNA or by hybridization with bacterial or fungal species selected from those listed in Tables 4, 5 and 6, as described in the two previous sections. Oligonucleotides found to be specific were subsequently tested for their ubiquity by amplification (for primers) or by hybridization (for probes) with bacterial DNAs from isolates of the target species or genus. Results for specificity and ubiquity tests with the oligonucleotide primers are summarized in Table 7. The specificity and ubiquity of the PCR assays using the selected amplification primer pairs were tested directly from cultures (see Examples 9 and 10) of bacterial or fungal species.

The various species-specific and genus-specific PCR assays which are objects of the present invention are all specific. For the PCR assays specific to bacterial species or genus, this means that DNA isolated from a wide variety of bacterial species, other than that from the target species or genus and selected from Tables 4 and 5, could not be amplified. For the PCR assay specific to *Candida albicans*, it means there was no amplification with genomic DNA from the fungal species listed in Table 6 as well as with a variety of bacterial species selected from Tables 4 and 5.

The various species-specific and genus-specific PCR assays which are objects of the present invention are also all ubiquitous (Table 7). (i) The species-specific PCR assays for *E. faecium, L. monocytogenes, S. saprophyticus, S. agalactiae* and *C. albicans* amplified genomic DNA from all or most strains of the target species tested, which were obtained from various sources and which are representative of the diversity within each target species (Table 7). The species identification of all of these strains was based on classical biochemical methods which are routinely used in clinical microbiology laboratories. (ii) The genus-specific PCR assays specific for *Enterococcus* spp., *Staphylococcus* spp., *Streptococcus* spp. and *Neisseda* spp. amplified genomic DNA from all or most strains of the target genus tested, which represent all clinically important bacterial species for each target genus. These strains were obtained from various sources and are representative of the diversity within each target genus. Again, the species identification of all of these strains was based on classical biochemical methods which are routinely used in clinical microbiology laboratories. More specifically, the four genus-specific PCR assays amplified the following species: (1) The *Enterococcus*-specific assay amplified efficiently DNA from all of the 11 enterococcal species tested including *E. avium, E. casseliflavus, E. dispar, E. durans, E. faecalis, E. faecium, E. flavescens, E. gallinarum, E. hirae, E. mundtii* and *E. raffinosus*. (2) The *Neisseria*-specific assay amplified efficiently DNA from all of the 12 neisserial species tested including *N. canis, N. cinerea, N. elongata, N. flavescens, N. gonorrhoeae, N. lactamica, N. meningitidis, N. mucosa, N. polysaccharea, N. sicca, N. subflava* and *N. weaveri*. (3) The *Staphylococcus*-specific assay amplified efficiently DNA from 13 of the 14 *staphylococcal* species tested including *S. aureus, S. audcularis, S. capitis, S. cohnii, S. epidernidis, S. haemolyticus, S. hominis, S. lugdunensis, S. saprophyticus, S. schleifedi, S. simulans, S. wameri* and *S. xylosus*. The *staphylococcal* species which could not be amplified is *S. sciuri*. (4) Finally, the *Streptococcus*-specific assay amplified efficiently DNA from all of the 22 streptococcal species tested including *S. agalactiae, S. anginosus, S. bovis, S. constellatus, S. crista, S. dysgalactiae, S. equi, S. gordonii, S. intermedius, S. mitis, S. mutans, S. oralis, S. parasanguis, S. pneumoniae, S. pyogenes, S. salivarius, S. sanguis, S. sabrinus, S. suis, S. uberis, S. vestibularis* and *S. viridans*. On the other hand, the *Streptococcus*-specific assay did not amplify 3 out of 9 strains of *S. mutans* and 1 out of 23 strains of *S. salivarius*, thereby showing a slight lack of ubiquity for these two streptococcal species.

All specific and ubiquitous amplification primers for each target microbial species or genus or antibiotic resistance gene investigated are listed in Annex VI. Divergence in the sequenced DNA fragments can occur, insofar as the divergence of these sequences or a part thereof does not affect the specificity of the probes or amplification primers. Variant bacterial DNA is under the scope of this invention.

The PCR amplification primers listed in Annex VI were all tested for their specificity and ubiquity using reference strains as well as clinical isolates from various geographical locations. The 351 reference strains used to test the amplification and hybridization assays (Tables 4, 5 and 6) were obtained from (i) the American Type Culture Collection (ATCC): 85%, (ii) the Laboratoire de santé publique du Québec (LSPQ): 10%, (iii) the Centers for Disease Control and Prevention (CDC): 3%, (iv) the National Culture Type Collection (NCTC): 1% and (v) several other reference laboratories throughout the world: 1%. These reference strains are representative of (i) 90 gram-negative bacterial species (169 strains; Table 4), (ii) 97 gram-positive bacterial species (154 strains; Table 5) and (iii) 12 fungal species (28 strains; Table 6).

Antibiotic Resistance Genes

Antimicrobial resistance complicates treatment and often leads to therapeutic failures. Furthermore, overuse of antibiotics inevitably leads to the emergence of bacterial resistance. Our goal is to provide clinicians, in approximately one hour, the needed information to prescribe optimal treatments.

Besides the rapid identification of negative clinical specimens with DNA-based tests for universal bacterial detection and the identification of the presence of a specific pathogen in the positive specimens with species-and/or genus-specific DNA-based tests, clinicians also need timely information about the ability of the bacterial pathogen to resist antibiotic treatments. We feel that the most efficient strategy to evaluate rapidly bacterial resistance to antimicrobials is to detect directly from the clinical specimens the most common and clinically important antibiotic resistance genes (i.e. DNA-based tests for the detection of antibiotic resistance genes). Since the sequence from the most important and common bacterial antibiotic resistance genes are available from databases, our strategy was to use the sequence from a portion or from the entire resistance gene to design specific oligonucleotide primers or probes which will be used as a basis for the development of rapid DNA-based tests. The sequence from each of the bacterial antibiotic resistance genes selected on the basis of their clinical relevance (i.e. high incidence and importance) is given in the Sequence Listing. Tables 9 and 10 summarize some characteristics of the selected antibiotic resistance genes. Our approach is unique because the antibiotic resistance genes detection and the bacterial detection and identification are performed simultaneously in multiplex assays under uniform PCR amplification conditions (Example 13).

Annex VI provides a list of all amplification primers selected from 26 clinically important antibiotic resistance genes which were tested in PCR assays. The various PCR assays for antibiotic resistance genes detection and identification were validated by testing several resistant bacterial isolates known to carry the targeted gene and obtained from various countries. The testing of a large number of strains which do not carry the targeted resistance gene was also performed to ensure that all assays were specific. So far, all PCR assays for antibiotic resistance genes are highly specific and have detected all control resistant bacterial strains known to carry the targeted gene. The results of some clinical studies to validate the array of PCR assays for the detection and identification of antibiotic resistance genes and correlate these DNA-based assays with standard antimicrobials susceptibility testing methods are presented in Tables 11 and 12.

Universal Bacterial Detection

In the routine microbiology laboratory, a high percentage of clinical specimens sent for bacterial identification are negative by culture (Table 4). Testing clinical samples with universal amplification primers or universal probes to detect the presence of bacteria prior to specific identification and screen out the numerous negative specimens is thus useful as it saves costs and may rapidly orient the clinical management of the patients. Several amplification primers and probes were therefore synthesized from highly conserved portions of bacterial sequences from the tuf genes (Table 8). The universal primer selection was based on a multiple sequence alignment constructed with sequences determined by us or selected from available database sequences as described in Example 1 and Annex I.

For the identification of database sequences suitable for the universal detection of bacteria, we took advantage of the fact that the complete genome sequences for two distant microorganisms (i.e. *Mycoplasma genitalium* and *Haemophilus influenzae*) are available. A comparison of the amino acid sequence for all proteins encoded by the genome of these two distant microorganisms led to the identification of highly homologous proteins. An analysis of these homologous proteins allowed to select some promising candidates for the development of universal DNA-based assays for the detection of bacteria. Since the complete nucleotide sequence of several other microbial genomes are presently available in databases, a person skilled in the art could arrive to the same conclusions by comparing genomes sequences other than those of *Mycoplasma genitalium* and *Haemophilus influenzae*. The selected tuf gene encodes a protein (EF-Tu) involved in the translation process during protein synthesis. Subsequently, an extensive nucleotide sequence analysiswas performed with the tuf gene sequences available in databases as well as with novel tuf sequences which we have determined as described previously. All computer analysis of amino acid and nucleotide sequences were performed by using the GCG programs. Subsequently, optimal PCR primers for the universal amplification of bacteria were selected with the help of the Oligo™ program. The selected primers are degenerated at several nucleotide positions and contain several inosines in order to allow the amplification of all clinically relevant bacterial species (Annex I). Inosine is a nucleotide analog able to specifically bind to any of the four nucleotides A, C, G or T. Degenerated oligonucleotides consist of an oligonucleotide mix having two or more of the four nucleotides A, C, G or T at the site of mismatches. The inclusion of inosine and/or of degenerescences in the amplification primers allow mismatch tolerance thereby permitting the amplification of a wider array of target nucleotide sequences (Dieffenbach and Dveksler, 1995 PCR Primer: A Laboratory Manual, Cold Spring Harbor Laboratory Press, Plainview, N.Y.).

The amplification conditions with the universal primers were identical to those used for the species-and genus-specific amplification assays except that the annealing temperature was 50° C. instead of 55° C. This universal PCR assay was specific and nearly ubiquitous for the detection of bacteria. The specificity for bacteria was verified by amplifying genomic DNA isolated from the 12 fungal species listed in Table 6 as well as genomic DNA from *Leishmania donovani*, *Saccharomyces cerevisiae* and human lymphocytes. None of the above eukaryotic DNA preparations could be amplified by the universal assay, thereby suggesting that this test is specific for bacteria. The ubiquity of the universal assay was verified by amplifying genomic DNAs from 116 reference strains which represent 95 of the most clinically relevant bacterial species. These species have been selected from the bacterial species listed in Tables 4 and 5. We found that 104 of these 116 strains could be amplified. The bacterial species which could not be amplified belong to the following genera: *Corynebactedum*(11 species) and *Stenotrophomonas*(1 species). Sequencing of the tuf genes from these bacterial species has been recently performed. This sequencing data has been used to select new universal primers which may be more ubiquitous. These primers are in the process of being tested. We also observed that for several species the annealing temperature had to be reduced to 45° C. in order to get an efficient amplification. These bacterial species include *Gemella morbilbrum*, *Listeria* spp. (3 species) and *Gardnerella vaginalis*. It is important to note that the 95 bacterial species selected from Tables 4 and 5 to test the ubiquity of the universal assay include all of the most clinically relevant bacterial species associated with a variety of human infections acquired in the community or in hospitals (nosocomial infections). The most clinically important bacterial and fungal pathogens are listed in Tables 1 and 2.

EXAMPLES AND ANNEXES

The following examples and annexes are intended to be illustrative of the various methods and compounds of the invention, rather than limiting the scope thereof.

The various annexes show the strategies used for the selection of amplification primers from tuf sequences or from the recA gene: (i) Annex I illustrates the strategy used for the selection of the universal amplification primers from tuf sequences. (ii) Annex II shows the strategy used for the selection of the amplification primers specific for the genus *Enterococcus* from tuf sequences. (iii) Annex III illustrates the strategy used for the selection of the amplification primers specific for the genus *Staphylococcus* from tuf sequences. (iv) Annex IV shows the strategy used for the selection of the amplification primers specific for the species *Candida albicans* from tuf sequences. (v) Annex V illustrates the strategy used for the selection of the amplification primers specific for the genus *Streptococcus* from recA sequences. (vi) Annex VI gives a list of all selected primer pairs. As shown in these annexes, the selected amplification primers may contain inosines and/or degenerescences. Inosine is a nucleotide analog able to specifically bind to any of the four nucleotides A, C, G or T. Alternatively, degenerated oligonucleotides which consist of an oligonucleotide mix having two or more of the four nucleotides A, C, G or T at the site of mismatches were used. The inclusion of inosine and/or of degenerescences in the amplification primers allow mismatch tolerance thereby permitting the amplification of a wider array of target nucleotide sequences (Dieffenbach and Dveksler, 1995 PCR Primer: A Laboratory Manual, Cold Spring Harbor Laboratory Press, Plainview, N.Y.).

EXAMPLES

Example 1

Selection of universal PCR primers from tuf sequences. As shown in Annex I, the comparison of tuf sequences from a variety of bacterial and eukaryotic species allowed the selection of PCR primers which are universal for the detection of bacteria. The strategy used to design the PCR primers was based on the analysis of a multiple sequence alignment of various tuf sequences. This multiple sequence alignment includes tuf sequences from 38 bacterial species and 3 eukaryotic species either determined by us or selected from databases (Table 13). A careful analysis of this multiple sequence alignment allowed the selection of primer sequences which are conserved within eubacteria but which discriminate sequences from eukaryotes, thereby permitting the universal detection of bacteria. As shown in Annex I, the selected primers contain several inosines and degenerescences. This was necessary because there is a relatively high polymorphism among bacterial tuf sequences despite the fact that this gene is highly conserved. In fact, among the tuf sequences that we determined, we found many nucleotide variations as well as some deletions and/or insertions of amino acids. The selected universal primers were specific and ubiquitous for bacteria (Table 7). Of the 95 most clinically important bacterial species tested, 12 were not amplified. These species belong to the genera *Corynebacterium*(11 species) and *Stenotrophomonas*(1 species). The universal primers did not amplify DNA of non-bacterial origin, including human and other types of eukaryotic DNA.

Example 2

Selection of genus-specific PCR primers from tuf sequences. As shown in Annexes 2 and 3, the comparison of tuf sequences from a variety of bacterial species allowed the selection of PCR primers specific for *Enterococcus* spp. or for *Staphylococcus* spp. The strategy used to design the PCR primers was based on the analysis of a multiple sequence alignment of various tuf sequences. These multiple sequence alignments include the tuf sequences of four representative bacterial species selected from each target genus as well as tuf sequences from species of other closely related bacterial genera. A careful analysis of those alignments allowed the selection of oligonucleotide sequences which are conserved within the target genus but which discriminate sequences from other closely related genera, thereby permitting the genus-specific and ubiquitous detection and identification of the target bacterial genus.

For the selection of primers specific for *Enterococcus* spp. (Annex II), we have sequenced a portion of approximately 890 bp of the tuf genes for *Enterococcus avium, E. faecalis, E. faecium* and *E. gallinarum*. All other tuf sequences used in the alignment were either sequenced by us or selected from databases. The analysis of this sequence alignment led to the selection of a primer pair specific and ubiquitous for *Enterococcus* spp. (Table 7). All of the 11 enterococcal species tested were efficiently amplified and there was no amplification with genomic DNA from bacterial species of other genera.

For the selection of primers specific for *Staphylococcus* spp. (Annex III), we have also sequenced a portion of approximately 890 bp of the tuf genes for *Staphylococcus aureus, S. epidermidis, S. saprophyticus* and *S. simulans*. All other tuf sequences used in the alignment were either sequenced by us or selected from databases. The analysis of this sequence alignment led to the selection of two primer pairs specific and ubiquitous for *Staphylococcus* spp. (Table 7). Annex III shows the strategy used to select one of these two PCR primer pairs. The same strategy was used to select the other primer pair. Of the 14 staphylococcal species tested, one (*S. sciuri*) could not be amplified by the *Staphylococcus*-specific PCR assays using either one of these two primer pairs. For PCR assays using either one of these two primer pairs, there was no amplification with DNA from species of other bacterial genera.

Example 3

Selection from tuf sequences of PCR primers specific for *Candida albicans*. As shown in Annex IV, the comparison of tuf sequences from a variety of bacterial and eukaryotic species allowed the selection of PCR primers specific for *Candida albicans*. The strategy used to design the PCR primers was based on the analysis of a multiple sequence alignment of various tuf sequences. This multiple sequence alignment includes tuf sequences of five representative fungal species selected from the genus Candida which were determined by our group (i.e. *C. albicans, C. glabrata, C. krusei, C. parapsilosis* and *C. tropicalis*) as well as tuf sequences from other closely related fungal species. tuf sequences from various bacterial species were also included. A careful analysis of this sequence alignment allowed the selection of primers from the *C. albicans* tuf sequence; these primers discriminate sequences from other closely related *Candida* species and other fungal species, thereby permitting the species-specific and ubiquitous detection and identification of *C. albicans* (Table 7). All of 88 *Candida albicans* strains tested were efficiently amplified and there was no amplification with genomic DNA from other fungal or bacterial species.

Example 4

Selection of PCR primers specific for *Streptococcus* from recA. As shown in Annex V, the comparison of the various bacterial recA gene sequences available from databases (GenBank and EMBL) was used as a basis for the selection of PCR primers which are specific and ubiquitous for the bacterial genus *Streptococcus*. Since sequences of the recA gene are available for many bacterial species including five species of streptococci, it was possible to choose sequences well conserved within the genus *Streptococcus* but distinct from the recA sequences for other bacterial genera. When there were mismatches between the recA gene sequences from the five *Streptococcus* species, an inosine residue was incorporated into the primer (Annex V). The selected primers, each containing one inosine and no degenerescence, were specific and ubiquitous for *Streptococcus* species (Table 7). This PCR assay amplified all of the 22 streptococcal species tested. However, the *Streptococcus*-specific assay did not amplify DNA from 3 out of 9 strains of *S. mutans* and 1 out of 3 strains of *S. salivarius*. There was no amplification with genomic DNA from other bacterial genera (Table 7).

Example 5

Nucleotide sequencing of DNA fragments. The nucleotide sequence of a portion of the tuf genes from a variety of bacterial or fungal species was determined by using the dideoxynucleotide chain termination sequencing method (Sanger et al., 1977, Proc. Natl. Acad. Sci. USA. 74:5463-5467). The sequencing was performed by using an Applied Biosystems automated DNA sequencer (model 373A) with their PRISM™ Sequenase™ Terminator Double-stranded DNA Sequencing Kit (Perkin-Elmer Corp., Applied Biosystems Division, Foster City, Calif.). The sequencing strategy does not discriminate tufA and tufB genes because the sequencing primers hybridize efficiently to both bacterial tuf genes. These DNA sequences are shown in the sequence listing (SEQ ID Nos: 118 to 146). The presence of several degenerated nucleotides in the various tuf sequences determined by our group (Table 13) corresponds to sequence variations between tufA and tufB.

Oligonucleotide primers and probes selection. Oligonucleotide probes and amplification primers were selected from the given proprietary DNA fragments or database sequences using the Oligo™ program and were synthesized with an automated ABI DNA synthesizer (Model 391, Perkin-Elmer Corp., Applied Biosystems Division) using phosphoramidite chemistry.

Example 6

Labeling of oligonucleotides for hybridization assays. Each oligonucleotide was 5' end-labeled with $\gamma$-$^{32}$P (dATP) by the T4 polynucleotide kinase (Pharmacia) as described earlier. The label could also be non-radioactive.

Specificity test for oliqonucleotide probes. All labeled oligonucleotide probes were tested for their specificity by hybridization to DNAs from a variety of bacterial and fungal species selected from Tables 4, 5 and 6 as described earlier. Species-specific or genus-specific probes were those hybridizing only to DNA from the microbial species or genus from which it was isolated. Oligonucleotide probes found to be specific were submitted to ubiquity tests as follows.

Ubiquity test for oligonucleotide probes. Specific oligonucleotide probes were then used in ubiquity tests with strains of the target species or genus including reference strains and other strains obtained from various countries and which are representative of the diversity within each target species or genus. Chromosomal DNAs from the isolates were transferred onto nylon membranes and hybridized with labeled oligonucleotide probes as described for specificity tests. The batteries of isolates constructed for each target species or genus contain reference ATCC strains as well as a variety of clinical isolates obtained from various sources. Ubiquitous probes were those hybridizing to at least 80% of DNAs from the battery of clinical isolates of the target species or genus.

Example 7

Same as example 6 except that a pool of specific oligonucleotide probes is used for microbial identification (i) to increase sensitivity and assure 100% ubiquity or (ii) to identify simultaneously more than one microbial species and/or genus. Microbial identification could be performed from microbial cultures or directly from any clinical specimen.

Example 8

Same as example 6 except that bacteria or fungi were detected directly from clinical samples. Any biological sample was loaded directly onto a dot blot apparatus and cells were lysed in situ for bacterial or fungal detection and identification. Blood samples should be heparizined in order to avoid coagulation interfering with-their convenient loading on a dot blot apparatus.

Example 9

PCR amplification. The technique of PCR was used to increase the sensitivity and the rapidity of the assays. The sets of primers were tested in PCR assays performed directly from bacterial colonies or from a standardized bacterial suspension (see Example 10) to determine their specificity and ubiquity (Table 7). Examples of specific and ubiquitous PCR primer pairs are listed in Annex VI.

Specificity and ubiquity tests for amplification primers. The specificity of all selected PCR primer pairs was tested against DNAs from a variety of bacterial and fungal species selected from Tables 4, 5 and 6 as described earlier. Primer pairs found specific for each species or genus were then tested for their ubiquity to ensure that each set of primers could amplify at least 90% of DNAs from a battery of isolates of the target species or genus. The batteries of isolates constructed for each species contain reference ATCC strains and various clinical isolates from around the world which are representative of the diversity within each species or genus.

Standard precautions to avoid false positive PCR results should be taken (Kwok and Higuchi, 1989, Nature, 239:237-238). Methods to inactivate PCR amplification products such as the inactivation by uracil-N-glycosylase may be used to control PCR carryover.

Example 10

Amplification directly from bacterial or yeast cultures. PCR assays were performed either directly from a bacterial colony or from a bacterial suspension, the latter being adjusted to a standard McFarland 0.5 (corresponds to approximately $1.5 \times 10^8$ bacteria/mL). In the case of direct amplification from a colony, a portion of a colony was transferred using a plastic rod directly into a 20 µL PCR reaction mixture containing 50 mM KCl, 10 mM Tris-HCl (pH 9.0), 0.1% Triton X-100, 2.5 mM MgCl$_2$, 0.4 µM of each primer, 200 µM of each of the four dNTPs and 0.5 unit of Taq DNA polymerase (Promega) combined with the TaqStar™ antibody (Clontech Laboratories Inc.). For the bacterial suspension, 1 µL of the cell suspension was added to 19 µL of the same PCR reaction mixture. For the identification from yeast cultures, 1 µL of a standard McFarland 1.0 (corresponds to approximately $3.0 \times 10^8$ bacteria/mL) concentrated 100 times by centrifugation was added directly to the PCR reaction. This concentration step for yeast cells was performed because a McFarland 0.5 for yeast cells has approximately 200 times fewer cells than a McFarland 0.5 for bacterial cells.

PCR reactions were then subjected to thermal cycling (3 min at 95° C. followed by 30 cycles of 1 second at 95° C. for the denaturation step and 30 seconds at 55° C. for the annealing-extension step) using a PTC-200 thermal cycler. PCR amplification products were then analyzed by standard agarose gel (2%) electrophoresis. Amplification products were visualized in agarose gels containing 0.25 µg/mL of ethidium bromide under UV at 254 nm. The entire PCR assay can be completed in approximately one hour.

Primer sequences derived from highly conserved regions of the bacterial 16S ribosomal RNA gene were used to provide an internal control for all PCR reactions. Alternatively, the internal control was derived from sequences not found in microorganisms or in the human genome. The internal control was integrated into all amplification reactions to verify the efficiency of the PCR assays and to ensure that significant PCR inhibition was absent. The internal control derived from rRNA was also useful to monitor the efficiency of the bacterial lysis protocols. The internal control and the species-specific or genus-specific amplifications were performed simultaneously in multiplex PCR assays.

Example 11

Amplification directly from urine specimens. For PCR amplification performed directly from urine specimens, 1 µL of urine was mixed with 4 µL of a lysis solution containing 500 mM KCl, 100 mM tris-HCl (pH 9.0), 1% triton X-100. After incubation for at least 15 minutes at room temperature, 1 µL of the treated urine specimen was added directly to 19 µL of the PCR reaction mixture. The final concentration of the PCR reagents was 50 mM KCl, 10 mM Tris (pH 9.0), 0.1% Triton X-100, 2.5 mM $MgCl_2$, 0.4 µM of each primer, 200 µM of each of the four dNTPs. In addition, each 20 µL reaction contained 0.5 unit of Taq DNA polymerase (Promega) combined with the TaqStart™ antibody (Clontech Laboratories Inc.).

Strategies for the internal control, PCR amplification and agarose gel detection of the amplicons are as previously described in example 10.

Example 12

Detection of antibiotic resistance genes. The presence of specific antibiotic resistance genes which are frequently encountered and clinically relevant is identified using the PCR amplification or hybridization protocols described previously. Specific oligonucleotides used as a basis for the DNA-based tests are selected from the antibiotic resistance gene sequences. These tests, which allow the rapid evaluation of bacterial resistance to antimicrobial agents, can be performed either directly from clinical specimens, from a standardized bacterial suspension or from a bacterial colony and should complement diagnostic tests for the universal detection of bacteria as well as for the species-specific and genus-specific microbial detection and identification.

Example 13

Same as examples 10 and 11 except that assays were performed by multiplex PCR (i.e. using several pairs of primers in a single PCR reaction) to reach an ubiquity of 100% for the specific targeted pathogen(s). For more heterogeneous microbial species or genus, a combination of PCR primer pairs may be required to detect and identify all representatives of the target species or genus.

Multiplex PCR assays could also be used to (i) detect simultaneously several microbial species and/or genera or, alternatively, (ii) to simultaneously detect and identify bacterial and/or fungal pathogens and detect specific antibiotic resistance genes either directly from a clinical specimen or from bacterial cultures.

For these applications, amplicon detection methods should be adapted to differentiate the various amplicons produced. Standard agarose gel electrophoresis could be used because it discriminates the amplicons based on their sizes. Another useful strategy for this purpose would be detection using a variety of fluorescent dyes emitting at different wavelengths. The fluorescent dyes can be each coupled with a specific oligonucleotide linked to a fluorescence quencher which is degraded during amplification to release the fluorescent dyes (e.g. TaqMan™, Perkin Elmer).

Example 14

Detection of amplification products. The person skilled in the art will appreciate that alternatives other than standard agarose gel electrophoresis (Example 10) may be used for the revelation of amplification products. Such methods may be based on fluorescence polarization or on the detection of fluorescence after amplification (e.g. Amplisensor™, Biotronics; TaqMan™, Perkin-Elmer Corp.) or other labels such as biotin (SHARP Signal™ system, Digene Diagnostics). These methods are quantitative and may be automated. One of the amplification primers or an internal oligonucleotide probe specific to the amplicon(s) derived from the species-specific, genus-specific or universal DNA fragments is coupled with the fluorescent dyes or with any other label. Methods based on the detection of fluorescence are particularly suitable for diagnostic tests since they are rapid and flexible as fluorescent dyes emitting at different wavelengths are available.

Example 15

Species-specific, genus-specific, universal and antibiotic resistance gene amplification primers can be used in other rapid amplification procedures such as the ligase chain reaction (LCR), transcription-mediated amplification (TMA), self-sustained sequence replication (3SR), nucleic acid sequence-based amplification (NASBA), strand displacement amplification (SDA), cycling probe technology (CPT) and branched DNA (bDNA) or any other methods to increase the sensitivity of the test. Amplifications can be performed from isolated bacterial cultures or directly from any clinical specimen. The scope of this invention is therefore not limited to the use of the DNA sequences from the enclosed Sequence Listing for PCR only but rather includes the use of any procedures to specifically detect bacterial DNA and which may be used to increase rapidity and sensitivity of the tests.

Example 16

A test kit would contain sets of probes specific for each microbial species or genus as well as a set of universal probes. The kit is provided in the form of test components, consisting of the set of universal probes labeled with non-radioactive labels as well as labeled species-or genus-specific probes for the detection of each pathogen of interest in specific types of clinical samples. The kit will also include test reagents necessary to perform the pre-hybridization, hybridization, washing steps and hybrid detection. Finally, test components for the detection of known antibiotic resistance genes (or derivatives therefrom) will be included. Of course, the kit will include standard samples to be used as negative and positive controls for each hybridization test.

Components to be included in the kits will be adapted to each specimen type and to detect pathogens commonly encountered in that type of specimen. Reagents for the universal detection of bacteria will also be included. Based on the sites of infection, the following kits for the specific detection of pathogens may be developed:

- A kit for the universal detection of bacterial or fungal pathogens from all clinical specimens which contains sets of probes specific for highly conserved regions of the microbial genomes.
- A kit for the detection of microbial pathogens retrieved from urine samples, which contains 5 specific test components (sets of probes for the detection of *Enterococcus faecium, Enteroccus species, Staphylococcus saprophyticus, Staphylococcus* species and *Candida albicans*).
- A kit for the detection of respiratory pathogens which contains 3 specific test components (sets of probes for the detection of *Staphylococcus* species, *Enterococcus* species and *Candida albicans*).
- A kit for the detection of pathogens retrieved from blood samples, which contains 10 specific test components (sets of probes for the detection of *Streptococcus* species, *Streptococcus agalactiae, Staphylococcus* species, *Staphylococcus saprophyticus, Enterococcus* species, *Enterococcus faecium, Neisseria* species, *Neisseria meningitidis, Listeria monocytogenes* and *Candida albicans*). This kit can also be applied for direct detection and identification from blood cultures.
- A kit for the detection of pathogens causing meningitis, which contains 5 specific test components (sets of probes for the detection of *Streptococcus* species, *Listedia monocytogenes, Neisseda meningitidis, Neisseda* species and *Staphylococcus* species).
- A kit for the detection of clinically important antibiotic resistance genes which contains sets of probes for the specific detection of at least one of the 26 following genes associated with antibiotic resistance: $bla_{tem}$, $bla_{rob}$, $bla_{shv}$, $bla_{oxa}$, blaZ, aadB, aacC1, aacC2, aacC3, aacA4, aac6'-lla, ermA, ermB, ermC, mecA, vanA, vanB, vanC, satA, aac(6')-aph(2''), aad(6'), vat, vga, msrA, sul and int.
- Other kits adapted for the detection of pathogens from skin, abdominal wound or any other clinically relevant infections may also be developed.

Example 17

Same as example 16 except that the test kits contain all reagents and controls to perform DNA amplification assays. Diagnostic kits will be adapted for amplification by PCR (or other amplification methods) performed directly either from clinical specimens or from microbial cultures. Components required for (i) universal bacterial detection, (ii) species-specific and genus-specific bacterial and/or fungal detection and identification and (iii) detection of antibiotic resistance genes will be included.

Amplification assays could be performed either in tubes or in microtitration plates having multiple wells. For assays in plates, the wells will contain the specific amplification primers and control DNAs and the detection of amplification products will be automated. Reagents and amplification primers for universal bacterial detection will be included in kits for tests performed directly from clinical specimens. Components required for species-specific and genus-specific bacterial and/or fungal detection and identification as well as for the simultaneous antibiotic resistance genes detection will be included in kits for testing directly from bacterial or fungal cultures as well as in kits for testing directly from any type of clinical specimen.

The kits will be adapted for use with each type of specimen as described in example 16 for hybridization-based diagnostic kits.

Example 18

It is understood that the use of the probes and amplification primers described in this invention for bacterial and/or fungal detection and identification is not limited to clinical microbiology applications. In fact, we feel that other sectors could also benefit from these new technologies. For example, these tests could be used by industries for quality control of food, water, air, pharmaceutical products or other products requiring microbiological control. These tests could also be applied to detect and identify bacteria or fungi in biological samples from organisms other than humans (e.g. other primates, birds, plants, mammals, farm animals, livestock and others). These diagnostic tools could also be very useful for research purposes including clinical trials and epidemiological studies.

This invention has been described herein above, and it is readily apparent that modifications can be made thereto without departing from the spirit of this invention. These modifications are under the scope of this invention, as defined in the appended claims.

TABLE 1

Distribution (%) of nosocomial pathogens for various human infections in USA (1990-1992)[1].

| Pathogen | UTI[2] | SSI[3] | BSI[4] | Pneumonia | CSF[5] |
|---|---|---|---|---|---|
| *Escherichia coli* | 27 | 9 | 5 | 4 | 2 |
| *Staphylococcus aureus* | 2 | 21 | 17 | 21 | 2 |
| *Staphylococcus epidermidis* | 2 | 6 | 20 | 0 | 1 |
| *Enterococcus faecalis* | 16 | 12 | 9 | 2 | 0 |
| *Enterococcus faecium* | 1 | 1 | 0 | 0 | 0 |
| *Pseudomonas aeruginosa* | 12 | 9 | 3 | 18 | 0 |
| *Klebsiella pneumoniae* | 7 | 3 | 4 | 9 | 0 |
| *Proteus mirabilis* | 5 | 3 | 1 | 2 | 0 |
| *Streptococcus pneumoniae* | 0 | 0 | 3 | 1 | 18 |
| Group B Streptococci | 1 | 1 | 2 | 1 | 6 |
| Other Streptococci | 3 | 5 | 2 | 1 | 3 |
| *Haemophilus influenzae* | 0 | 0 | 0 | 6 | 45 |
| *Neisseria meningitidis* | 0 | 0 | 0 | 0 | 14 |
| *Listeria monocytogenes* | 0 | 0 | 0 | 0 | 3 |
| Other Enterococci | 1 | 1 | 0 | 0 | 0 |
| Other Staphylococci | 2 | | 8 | 13 | 20 |
| *Candida albicans* | 9 | 3 | 5 | 5 | 0 |
| Other Candida | 2 | | 1 | 3 | 10 |
| *Enterobacter* spp. | 5 | 7 | 4 | 12 | 2 |
| *Acinetobacter* spp. | 1 | 1 | 2 | 4 | 2 |
| *Citrobacter* spp. | 2 | 1 | 1 | 1 | 0 |
| *Serratia marcescens* | 1 | 1 | 1 | 3 | 1 |
| Other Klebsiella | 1 | 1 | 1 | 2 | 1 |
| Others | 0 | 6 | 4 | 5 | 0 |

[1]Data recorded by the National Nosocomial Infections Surveillance (NNIS) from 80 hospitals (Emori and Gaynes, 1993, Clin. Microbiol. Rev., 6: 428-442).
[2]Urinary tract infection.
[3]Surgical site infection.
[4]Bloodstream infection.
[5]Cerebrospinal fluid.

TABLE 2

Distribution (%) of bloodstream infection pathogens in Quebec (1995), Canada (1992), UK (1969-1988) and USA (1990-1992).

| Organism | Quebec[1] | Canada[2] | UK[3] Community-acquired | UK[3] Hospital-acquired | USA[4] Hospital-acquired |
|---|---|---|---|---|---|
| E. coli | 15.6 | 53.8 | 24.8 | 20.3 | 5.0 |
| S. epidermidis and other CoNS[5] | 25.8 | NI[6] | 0.5 | 7.2 | 31.0 |
| S. aureus | 9.6 | NI | 9.7 | 19.4 | 16.0 |
| S. pneumoniae | 6.3 | NI | 22.5 | 2.2 | NR[7] |
| E. faecalis | 3.0 | NI | 1.0 | 4.2 | NR |
| E. faecium | 2.6 | NI | 0.2 | 0.5 | NR |
| Enterococcus spp. | NR | NI | NR | NR | 9.0 |
| H. influenzae | 1.5 | NR | 3.4 | 0.4 | NR |
| P. aeruginosa | 1.5 | 8.2 | 1.0 | 8.2 | 3.0 |
| K. pneumoniae | 3.0 | 11.2 | 3.0 | 9.2 | 4.0 |
| P. mirabilis | NR | 3.9 | 2.8 | 5.3 | 1.0 |
| S. pyogenes | NR | NI | 1.9 | 0.9 | NR |
| Enterobacter spp. | 4.1 | 5.5 | 0.5 | 2.3 | 4.0 |
| Candida spp. | 8.5 | NI | NR | 1.0 | 8.0 |
| Others | 18.5 | 17.4[8] | 28.7 | 18.9 | 19.0 |

[1]Data obtained for 270 isolates collected at the Centre Hospitalier de l'Universite Laval (CHUL) during a 5 month period (May to October 1995).
[2]Data from 10 hospitals throughout Canada representing 941 gram-negative bacterial isolates. (Chamberland et al., 1992, Clin. Infect. Dis., 15: 615-628).
[3]Data from a 20-year study (1969-1988) for nearly 4000 isolates (Eykyn et al., 1990, J. Antimicrob. Chemother., Suppl. C, 25: 41-58).
[4]Data recorded by the National Nosocomial Infections Surveillance (NNIS) from 80 hospitals (Emori and Gaynes, 1993, Clin. Microbiol. Rev., 6: 428-442).
[5]Coagulase-negative staphylococci.
[6]NI, not included. This survey included only gram-negative species.
[7]NR, incidence not reported for these species or genera.
[8]In this case, 17.4 stands for other gram-negative bacterial species.

TABLE 3

Distribution of positive and negative clinical specimens tested at the microbiology laboratory of the CHUL (February 1994 -January 1995).

| Clinical specimens and/or sites | No. of samples tested (%) | % of positive specimens | % of negative specimens |
|---|---|---|---|
| Urine | 17,981 (54.5) | 19.4 | 80.6 |
| Blood culture/marrow | 10,010 (30.4) | 6.9 | 93.1 |
| Sputum | 1,266 (3.8) | 68.4 | 31.6 |
| Superficial pus | 1,136 (3.5) | 72.3 | 27.7 |
| Cerebrospinal fluid | 553 (1.7) | 1.0 | 99.0 |
| Synovial fluid | 523 (1.6) | 2.7 | 97.3 |
| Respiratory tract | 502 (1.5) | 56.6 | 43.4 |
| Deep pus | 473 (1.4) | 56.8 | 43.2 |
| Ears | 289 (0.9) | 47.1 | 52.9 |
| Pleural and pericardial fluid | 132 (0.4) | 1.0 | 99.0 |
| Peritoneal fluid | 101 (0.3) | 28.6 | 71.4 |
| Total: | 32,966 (100.0) | 20.0 | 80.0 |

TABLE 4

Gram-negative bacterial species (90) used to test the specificity of PCR primers and DNA probes.

| Bacterial species | Number of reference strains tested[a] |
|---|---|
| Acinetobacter baumannii | 1 |
| Acinetobacter lwoffii | 3 |
| Actinobacillus lignieresii | 1 |
| Alcaligenes faecalis | 1 |
| Alcaligenes odorans | 1 |
| Alcaligenes xylosoxydans subsp. denitrificans | 1 |
| Bacteroides distasonis | 1 |
| Bacteroides fragilis | 1 |
| Bacteroides ovatus | 1 |
| Bacteroides thetaiotaomicron | 1 |
| Bacteroides vulgatus | 1 |
| Bordetella bronchiseptica | 1 |
| Bordetella parapertussis | 1 |
| Bordetella pertussis | 2 |
| Burkholderia cepacia | 1 |
| Citrobacter amalonaticus | 1 |
| Citrobacter diversus subsp. koseri | 2 |
| Citrobacter freundii | 1 |
| Comamonas acidovorans | 1 |
| Enterobacter aerogenes | 1 |
| Enterobacter agglomerans | 1 |
| Enterobacter cloacae | 1 |
| Escherichia coli | 9 |
| Escherichia fergusonii | 1 |
| Escherichia hermannii | 1 |
| Escherichia vulneris | 1 |
| Flavobacterium meningosepticum | 1 |
| Flavobacterium indologenes | 1 |
| Flavobacterium odoratum | 1 |
| Fusobacterium necrophorum | 2 |
| Gardnerella vaginalis | 1 |
| Haemophilus | 1 |

TABLE 4-continued

Gram-negative bacterial species (90) used to test the specificity of PCR primers and DNA probes.

| Bacterial species | Number of reference strains tested[a] |
|---|---|
| haemolyticus | |
| *Haemophilus influenzae* | 12 |
| *Haemophilus parahaemolyticus* | 1 |
| *Haemophilus parainfluenzae* | 2 |
| *Hafnia alvei* | 1 |
| *Kingella indologenes* subsp. *suttonella* | 1 |
| *Kingella kingae* | 1 |
| *Klebsiella ornithinolytica* | 1 |
| *Klebsiella oxytoca* | 1 |
| *Klebsiella pneumoniae* | 8 |
| *Moraxella atlantae* | 1 |
| *Moraxella catarrhalis* | 5 |
| *Moraxella lacunata* | 1 |
| *Moraxella osloensis* | 1 |
| *Moraxella phenylpyruvica* | 1 |
| *Morganella morganii* | 1 |
| *Neisseria animalis* | 1 |
| *Neisseria canis* | 1 |
| *Neisseria caviae* | 1 |
| *Neisseria cinerea* | 1 |
| *Neisseria cuniculi* | 1 |
| *Neisseria elongata* subsp. *elongata* | 1 |
| *Neisseria elongata* subsp. *glycoytica* | 1 |
| *Neisseria flavescens* | 1 |
| *Neisseria flavescens* Branham | 1 |
| *Neisseria gonorrhoeae* | 18 |
| *Neisseria lactamica* | 1 |
| *Neisseria meningitidis* | 4 |
| *Neisseria mucosa* | 2 |
| *Neisseria polysaccharea* | 1 |
| *Neisseria sicca* | 3 |
| *Neisseria subflava* | 3 |
| *Neisseria weaveri* | 1 |
| *Ochrobactrum antropi* | 1 |
| *Pasteurella aerogenes* | 1 |
| *Pasteurella multocida* | 1 |
| *Prevotella melaninogenica* | 1 |
| *Proteus mirabilis* | 3 |
| *Proteus vulgaris* | 1 |
| *Providencia alcalifaciens* | 1 |
| *Providencia rettgeri* | 1 |
| *Providencia rustigianii* | 1 |
| *Providencia stuartii* | 1 |
| *Pseudomonas aeruginosa* | 14 |
| *Pseudomonas fluorescens* | 2 |
| *Pseudomonas stutzeri* | 1 |
| *Salmonella arizonae* | 1 |
| *Salmonella choleraesuis* | 1 |
| *Salmonella gallinarum* | 1 |
| *Salmonella typhimurium* | 3 |
| *Serratia liquefaciens* | 1 |
| *Serratia marcescens* | 1 |
| *Shewanella putida* | 1 |
| *Shigella boydii* | 1 |
| *Shigella dysenteriae* | 1 |
| *Shigella flexneri* | 1 |
| *Shigella sonnei* | 1 |
| *Stenotrophomonas maltophilia* | 1 |
| *Yersinia enterocolitica* | 1 |

[a]Most reference strains were obtained from the American Type Culture Collection (ATCC). The other reference strains were obtained from (i) the Laboratoire de Santé Publique du Québec (LSPQ), (ii) the Center for Disease Control and Prevention (CDC) and (iii) the National Culture Type Collection (NCTC).

TABLE 5

Gram-positive bacterial species (97) used to test the specificity of PCR primers and DNA probes.

| Bacterial species | Number of reference strains tested[a] |
|---|---|
| *Abiotrophia adiacens* | 1 |
| *Abiotrophia defectiva* | 1 |
| *Actinomyces israelii* | 1 |
| *Clostridium perfringens* | 1 |
| *Corynebacterium accolens* | 1 |
| *Corynebacterium aquaticum* | 1 |
| *Corynebacterium bovis* | 1 |
| *Corynebacterium cervicis* | 1 |
| *Corynebacterium diphteriae* | 6 |
| *Corynebacterium flavescens* | 1 |
| *Corynebacterium genitalium* | 6 |
| *Corynebacterium jeikeium* | 1 |
| *Corynebacterium kutcheri* | 1 |
| *Corynebacterium matruchotii* | 1 |
| *Corynebacterium minutissimum* | 1 |
| *Corynebacterium mycetoides* | 1 |
| *Corynebacterium pseudodiphtheriticum* | 1 |
| *Corynebacterium pseudogenitalium* | 6 |
| *Corynebacterium renale* | 1 |
| *Corynebacterium striatum* | 1 |
| *Corynebacterium ulcerans* | 1 |
| *Corynebacterium urealyticum* | 1 |
| *Corynebacterium xerosis* | 1 |
| *Enterococcus avium* | 1 |
| *Enterococcus casseliflavus* | 1 |
| *Enterococcus cecorum* | 1 |
| *Enterococcus dispar* | 1 |
| *Enterococcus durans* | 1 |
| *Enterococcus faecalis* | 6 |
| *Enterococcus faecium* | 3 |
| *Enterococcus flavescens* | 1 |
| *Enterococcus gallinarum* | 3 |
| *Enterococcus hirae* | 1 |
| *Enterococcus mundtii* | 1 |
| *Enterococcus pseudoavium* | 1 |
| *Enterococcus raffinosus* | 1 |
| *Enterococcus saccharolyticus* | 1 |
| *Enterococcus solitarius* | 1 |
| *Eubacterium lentum* | 1 |
| *Gemella haemolysans* | 1 |
| *Gemella morbillorum* | 1 |
| *Lactobacillus acidophilus* | 1 |
| *Listeria innocua* | 1 |
| *Listeria ivanovii* | 1 |
| *Listeria grayi* | 1 |
| *Listeria monocytogenes* | 3 |
| *Listeria murrayi* | 1 |
| *Listeria seeligeri* | 1 |
| *Listeria welshimeri* | 1 |
| *Micrococcus kristinae* | 1 |
| *Micrococcus luteus* | 1 |
| *Micrococcus lylae* | 1 |
| *Micrococcus roseus* | 1 |
| *Micrococcus varians* | 1 |
| *Peptococcus niger* | 1 |
| *Peptostreptococcus anaerobius* | 1 |
| *Peptostreptococcus asaccharolyticus* | 1 |
| *Staphylococcus aureus* | 10 |
| *Staphylococcus auricularis* | 1 |

TABLE 5-continued

Gram-positive bacterial species (97) used to test the specificity of PCR primers and DNA probes.

| Bacterial species | Number of reference strains tested[a] |
|---|---|
| Staphylococcus capitis subsp. urealyticus | 1 |
| Staphylococcus cohnii | 1 |
| Staphylococcus epidermidis | 2 |
| Staphylococcus haemolyticus | 2 |
| Staphylococcus hominis | 2 |
| Staphylococcus lugdunensis | 1 |
| Staphylococcus saprophyticus | 3 |
| Staphylococcus schleiferi | 1 |
| Staphylococcus sciuri | 1 |
| Staphylococcus simulans | 1 |
| Staphylococcus warneri | 1 |
| Staphylococcus xylosus | 1 |
| Streptococcus agalactiae | 6 |
| Streptococcus anginosus | 2 |
| Streptococcus bovis | 2 |
| Streptococcus constellatus | 1 |
| Streptococcus crista | 1 |
| Streptococcus dysgalactiae | 1 |
| Streptococcus equi | 1 |
| Streptococcus gordonii | 1 |
| Group C Streptococci | 1 |
| Group D Streptococci | 1 |
| Group E Streptococci | 1 |
| Group F Streptococci | 1 |
| Group G Streptococci | 1 |
| Streptococcus intermedius | 1 |
| Streptococcus mitis | 2 |
| Streptococcus mutans | 1 |
| Streptococcus oralis | 1 |
| Streptococcus parasanguis | 1 |
| Streptococcus pneumoniae | 6 |
| Streptococcus pyogenes | 3 |
| Streptococcus salivarius | 2 |
| Streptococcus sanguis | 2 |
| Streptococcus sobrinus | 1 |
| Streptococcus suis | 1 |
| Streptococcus uberis | 1 |
| Streptococcus vestibularis | 1 |

[a]Most reference strains were obtained from the American Type Culture Collection (ATCC). The other reference strains were obtained from (i) the Laboratoire de Santé Publique du Québec (LSPQ), (ii) the Center for Disease Control and Prevention (CDC) and (iii) the National Culture Type Collection (NCTC).

TABLE 6

Fungal species (12) used to test the specificity of PCR primers and DNA probes.

| Fungal species | Number of reference strains tested[a] |
|---|---|
| Candida albicans | 12 |
| Candida glabrata | 1 |
| Candida guilliermondii | 1 |
| Candida kefyr | 3 |
| Candida krusei | 2 |
| Candida lusitaniae | 1 |
| Candida parapsilosis | 2 |
| Candida tropicalis | 3 |
| Rhodotorula glutinis | 1 |
| Rhodotorula minuta | 1 |
| Rhodotorula rubra | 1 |
| Saccharomyces cerevisiae | 1 |

[a]Most reference strains were obtained from (i) the American Type Culture Collection (ATCC) and (ii) the Laboratoire de Santé Publique du Québec (LSPQ).

TABLE 7

PCR assays developed for several clinically important bacterial and fungal pathogens.

| Organism | Primer Pair[a] SEQ ID NO | Amplicon size (bp) | Ubiquity[b] | DNA amplification from culture[c] | specimens[d] |
|---|---|---|---|---|---|
| Enterococcus faecium | 1-2 | 216 | 79/80 | + | + |
| Listeria monocytogenes | 3-4 | 130 | 164/168[e] | + | + |
| Neisseria meningitidis | 5-6 | 177 | 258/258 | + | + |
| Staphylococcus saprophyticus | 7-8 | 149 | 245/260 | + | NT |
| Streptococcus agalactiae | 9-10 | 154 | 29/29 | + | + |
| Candida albicans | 11-12 | 149 | 88/88 | + | NT |
| Enterococcus spp. (11 species)[f] | 13-14 | 112 | 87/57 | + | NT |
| Neisseria spp. (12 species)[f] | 15-16 | 103 | 321/321 | + | + |
| Staphylococcus spp. (14 species) | 17-18 | 192 | 13/14 | + | NT |
|  | 19-20 | 221 | 13/14 | + | NT |
| Streptococcus spp. (22 species)[f] | 21-22 | 153 | 210/214[g] | + | + |
| Universal detection[h] (95 species)[i] | 23-24 | 309 | 104/116[i] | + | + |

[a]All primer pairs are specific in PCR assays since no amplification was observed with DNA from the bacterial and fungal species other than the species of interest listed in Tables 4, 5 and 6.
[b]Ubiquity was tested by using reference strains as well as strains from throughout the world, which are representatite of the diversity within each target species or genus.
[c]For all primer pairs, PCR amplifications performed directly from a standardized microbial suspension (MacFarland) or from a colony were all specific and ubiquitous.
[d]PCR assays performed directly from blood cultures, urine specimens or cerebrospinal fluid. NT, not tested.
[e]The four L. monocytogenes strains undetected are not clinical isolates. These strains were isolated from food and are not associated with a human infection.

TABLE 7-continued

PCR assays developed for several clinically important bacterial and fungal pathogens.

| Organism | Primer Pair[a] SEQ ID NO | Amplicon size (bp) | Ubiquity[b] | DNA amplification from culture[c] | specimens[d] |
|---|---|---|---|---|---|

[f]The bacterial species tested include all those clinically relevant for each genus (Tables 4 and 5). All of these species were efficiently amplified by their respective genus-specific PCR assay, except for the Staphylococcus-specific assay, which does not amplify *S. sciuri*.
[g]The *Streptococcus*-specific PCR assay did not amplify 3 out of 9 strains of *S. mutans* and 1 out of 3 strains of *S. salivarius*.
[h]The primers selected for universal bacterial detection do not amplify DNA of non-bacterial origin, including human and other types of eukaryotic genomic DNA.
[i]For the universal amplification, the 95 bacterial species tested represent the most clinically important bacterial species listed in Tables 4 and 5. The 12 strains not amplified are representatives of genera Corynebacterium (11 species) and Stenotrophomonas (1 species).

TABLE 8

Target genes for the various genus-specific, species-specific and universal amplification assays.

| Microorganisms | Gene | Protein encoded |
|---|---|---|
| *Candida albicans* | tuf | translation elongation factor EF-Tu |
| *Enterococcus faecium* | ddl | D-alanine:D-alanine ligase |
| *Listeria monocytogenes* | actA | actin-assembly inducing protein |
| *Neisseria meningitidis* | omp | outer membrane protein |
| *Streptococcus agalactiae* | cAMP | cAMP factor |
| *Staphylococcus saprophyticus* | unknown | unknown |
| *Enterococcus* spp. | tuf | translation elongation factor EF-Tu |
| *Neisseria* spp. | asd | ASA-dehydrogenase |
| *Staphylococcus* spp. | tuf | translation elongation factor EF-Tu |
| *Streptococcus* spp. | recA | RecA protein |
| Universal detection | tuf | translation elongation factor EF-Tu |

TABLE 9

Antibiotic resistance genes selected for diagnostic purposes.

| Genes | SEQ ID NOs selected primers | SEQ ID NOs originating fragment | Antibiotics | Bacteria[a] |
|---|---|---|---|---|
| bla$_{oxa}$ | 49-50 | 110 | β-lactams | Enterobacteriaceae, Pseudomonadaceae |
| blaZ | 51-52 | 111 | β-lactams | *Enterococcus* spp. |
| aac6'-IIa | 61-64 | 112 | Aminoglycosides | Pseudomonadaceae |
| ermA | 91-92 | 113 | Macrolides | *Staphylococcus* spp. |
| ermB | 93-94 | 114 | Macrolides | *Staphylococcus* spp. |
| ermC | 95-96 | 115 | Macrolides | *Staphylococcus* spp. |
| vanB | 71-74 | 116 | Vancomycin | *Enterococcus* spp. |
| vanC | 75-76 | 117 | Vancomycin | *Enterococcus* spp. |
| aad(6') | 173-174 | — | Streptomycin | *Enterococcus* spp. |

[a]Bacteria having high incidence for the specified antibiotic resistance genes. The presence of these antibiotic resistance genes in other bacteria is not excluded.

TABLE 10

Antibiotic resistance genes from our co-pending US (N.S. 08/526840) and PCT (PCT/CA/95/00528) patent applications for which we have selected PCR primer pairs.

| Genes | SEQ ID NOs of selected primers | Antibiotics | Bacteria[a] |
|---|---|---|---|
| bla$_{tem}$ | 37-40 | β-lactams | Enterobacteriaceae, Pseudomonadaceae, *Haemophilus* spp., *Neisseria* spp. |
| bla$_{rob}$ | 45-48 | β-lactams | *Haemophilus* spp., *Pasteurella* spp. |
| bla$_{shv}$ | 41-44 | β-lactams | *Klebsiella* spp. and other Enterobacteriaceae |
| aadB | 53-54 | Aminoglycosides | Enterobacteriaceae, Pseudomonadaceae |
| aacC1 | 55-56 | | |
| aacC2 | 57-58 | | |
| aacC3 | 59-60 | | |
| aacA4 | 65-66 | | |
| mecA | 97-98 | β-lactams | *Staphylococcus* spp. |
| vanA | 67-70 | Vancomycin | *Enterococcus* spp. |
| satA | 81-82 | Macrolides | *Enterococcus* spp. |
| aac(6')-aph(2") | 83-86 | Aminoglycosides | *Enterococcus* spp., *Staphylococcus* spp. |
| vat | 87-88 | Macrolides | *Staphylococcus* spp. |
| vga | 89-90 | Macrolides | *Staphylococcus* spp. |
| msrA | 77-80 | Erythromycin | *Staphylococcus* spp. |
| int | 99-102 | β-lactams, trimethoprim, aminoglycosides, antiseptic, chloramphenicol | Enterobacteriaceae, Pseudomonadaceae |
| sul | 103-106 | | |

[a]Bacteria having high incidence for the specified antibiotic resistance genes. The presence of these antibiotic resistance genes in other bacteria is not excluded.

TABLE 11

Correlation between disk diffusion and PCR amplification of antibiotic resistance genes in *Staphylococcus* species[a].

| Antibiotic | Phenotype | PCR | Disk diffusion (Kirby-Bauer)[b] Resistant | Intermediate | Sensitive |
|---|---|---|---|---|---|
| Penicillin | blaZ | + | 165 | 0 | 0 |
| | | − | 0 | 0 | 31 |
| Oxacillin | mecA | + | 51 | 11 | 4 |
| | | − | 2 | 0 | 128 |
| Gentamycin | aac(6') aph(2") | + | 24 | 18 | 6 |
| | | − | 0 | 0 | 148 |
| Erythromycin | ermA | + | 15 | 0 | 0 |
| | ermB | + | 0 | 0 | 0 |
| | ermC | + | 43 | 0 | 0 |
| | msrA | + | 4 | 0 | 0 |
| | | − | 0 | 1 | 136 |

[a]The *Staphylococcus* strains studied include *S. aureus* (82 strains), *S. epidermidis* (83 strains), *S. hominis* (2 strains), *S. capitis* (3 strains), *S. haemolyticus* (9 strains), *S. simulans* (12 strains) and *S. warneri* (5 strains), for a total of 196 strains.
[b]Susceptibility testing was performed by the method of Kirby-Bauer according to the protocol reccommended by the National Committee of Clinical Laboratory Standards (NCCLS).

TABLE 12

Correlation between disk diffusion profiles and PCR amplification of antibiotic resistance genes in *Enterococcus* species[a].

| Antibiotic | Phenotype | PCR | Disk diffusion (Kirby-Bauer)[b] | |
|---|---|---|---|---|
| | | | Resistant | Sensitive |
| Ampicillin | blaZ | + | 0 | 2 |
| | | − | 1 | 30 |
| Gentamycin | aac(6')aph(2") | + | 51 | 1 |
| | | − | 3 | 38 |
| Streptomycin | aad(6') | + | 26 | 15 |
| | | − | 6 | 27 |
| Vancomycin | vanA | + | 36 | 0 |
| | vanB | + | 26 | 0 |
| | | − | 0 | 40 |

[a]The *Enterococcus* strains studied include *E. faecalis* (33 strains) and *E. faecium* (69 strains), for a total of 102 strains.
[b]Susceptibility testing was performed by the method of Kirby-Bauer according to the protocol reccommended by the National Committee of Clinical Laboratory Standards (NC-CLS).

TABLE 13

Origin of tuf sequences in the Sequence Listing

| SEQ ID NO | Bacterial or fungal species | Source |
|---|---|---|
| 118 | *Abiotrophia adiacens* | This patent |
| 119 | *Abiotrophia defectiva* | This patent |
| 120 | *Candida albicans* | This patent |
| 121 | *Candida glabrata* | This patent |
| 122 | *Candida krusei* | This patent |
| 123 | *Candida parapsilosis* | This patent |
| 124 | *Candida tropicalis* | This patent |
| 125 | *Corynebacterium accolens* | This patent |
| 126 | *Corynebacterium diphteriae* | This patent |
| 127 | *Corynebacterium genitalium* | This patent |
| 128 | *Corynebacterium jeikeium* | This patent |
| 129 | *Corynebacterium pseudotuberculosis* | This patent |
| 130 | *Corynebacterium striatum* | This patent |
| 131 | *Enterococcus avium* | This patent |
| 132 | *Enterococcus faecalis* | This patent |
| 133 | *Enterococcus faecium* | This patent |
| 134 | *Enterococcus gallinarum* | This patent |
| 135 | *Gardnerella vaginalis* | This patent |
| 136 | *Listeria innocua* | This patent |
| 137 | *Listeria ivanovii* | This patent |
| 138 | *Listeria monocytogenes* | This patent |
| 139 | *Listeria seeligeri* | This patent |
| 140 | *Staphylococcus aureus* | This patent |
| 141 | *Staphylococcus epidermidis* | This patent |
| 142 | *Staphylococcus saprophyticus* | This patent |
| 143 | *Staphylococcus simulans* | This patent |
| 144 | *Streptococcus agalactiae* | This patent |
| 145 | *Streptococcus pneumoniae* | This patent |
| 146 | *Streptococcus salivarius* | This patent |
| 147 | *Agrobacterium tumefaciens* | Database |
| 148 | *Bacillus subtilis* | Database |
| 149 | *Bacteroides fragilis* | Database |
| 150 | *Borrelia burgdorferi* | Database |
| 151 | *Brevibacterium linens* | Database |
| 152 | *Burkholderia cepacia* | Database |
| 153 | *Chlamydia trachomatis* | Database |
| 154 | *Escherichia coli* | Database |
| 155 | *Fibrobacter succinogenes* | Database |
| 156 | *Flavobacterium ferrugineum* | Database |
| 157 | *Haemophilus influenzae* | Database |
| 158 | *Helicobacter pylori* | Database |
| 159 | *Micrococcus luteus* | Database |
| 160 | *Mycobacterium tuberculosis* | Database |
| 161 | *Mycoplasma genitalium* | Database |
| 162 | *Neisseria gonorrhoeae* | Database |
| 163 | *Rickettsia prowazekii* | Database |
| 164 | *Salmonella typhimurium* | Database |
| 165 | *Shewanella putida* | Database |
| 166 | *Stigmatella aurantiaca* | Database |
| 167 | *Streptococcus pyogenes* | Database |
| 168 | *Thiobacillus cuprinus* | Database |
| 169 | *Treponema pallidum* | Database |
| 170 | *Ureaplasma urealyticum* | Database |
| 171 | *Wolinella succinogenes* | Database |

ANNEX I

Strategy for the selection from tuf sequences of the universal amplification primers.

| | 491 | | 517...776 | | | 802 | SEQ ID NO |
|---|---|---|---|---|---|---|---|
| *Abiotrophia adiacens* | CA<u>ACTGTAAC</u> | <u>TGGTGTTGAA</u> | ATGTTCC...AA<u>ATGGT</u> | <u>AATGCCTGGT</u> | <u>GATAACGT</u>AA | | 118 |
| *Abiotrophia defectiva* | CT<u>ACCGTTAC</u> | <u>CGGTGTTGAA</u> | ATGTTCC...AA<u>ATGGT</u> | <u>TATGCCAGGC</u> | <u>GACAACGT</u>AC | | 119 |
| *Agrobacterium tumefaciens* | CG<u>ACTGTTAC</u> | <u>CGGCGTTGAA</u> | ATGTTCC...AA<u>ATGGT</u> | <u>TATGCCTGGC</u> | <u>GACAACGT</u>CA | | 147 |
| *Bacillus subtilis* | CA<u>ACTGTTAC</u> | <u>AGGTGTTGAA</u> | ATGTTCC...AA<u>ATGGT</u> | <u>TATGCCTGGA</u> | <u>GATAACAC</u>TG | | 148 |
| *Bacteroides fragilis* | CA<u>GTTGTAAC</u> | <u>AGGTGTTGAA</u> | ATGTTCC...AA<u>ATGGT</u> | <u>AATGCCGGGT</u> | <u>GATAACGT</u>AA | | 149 |
| *Borrelia burgdorferi* | CT<u>ACTGTTAC</u> | <u>TGGTGTTGAA</u> | ATGTTCC...AA<u>ATGGT</u> | <u>TATGCCTGGT</u> | <u>GATAATGT</u>TG | | 150 |
| *Brevibacterium linens* | CG<u>ACTGTCAC</u> | <u>CGCTATCGAG</u> | ATGTTCC...AG<u>ATGGT</u> | <u>CATGCCCGGC</u> | <u>GACACCAC</u>CG | | 151 |
| *Burkholderia cepacia* | CG<u>ACCTGCAC</u> | <u>GGGCGTTGAA</u> | ATGTTCC...AA<u>ATGGT</u> | <u>CATGCCGGGC</u> | <u>GACAACGT</u>GT | | 152 |

ANNEX I-continued

Strategy for the selection from tuf sequences of the universal amplification primers.

| | 491 | 517...776 | 802 | SEQ ID NO |
|---|---|---|---|---|
| *Chlamydia trachomatis* | CG<u>ATTGTTAC</u> <u>TGGGGTTGAA</u> <u>ATGTT</u>CA...AG<u>ATGGT</u> <u>CATGCCTGGG</u> <u>GATAACGT</u>TG | | | 153 |
| *Corynebacterium diphteriae* | CC<u>ACCGTTAC</u> <u>CGGTATCGAG</u> <u>ATGTT</u>CC...AG<u>ATGGT</u> <u>CATGCCTGGC</u> <u>GACAACGT</u>CG | | | 126 |
| *Corynebacterium genitalium* | CC<u>ACCGTTAC</u> <u>CTCCATCGAG</u> <u>ATGTT</u>CA...AG<u>ATGGT</u> <u>TATGCCGGGC</u> <u>GACAACGT</u>TG | | | 127 |
| *Corynebacterium jeikeium* | CC<u>ACCGTTAC</u> <u>CTCCATCGAG</u> <u>ATGTT</u>CA...AG<u>ATGGT</u> <u>TATGCCGGGC</u> <u>GACAACGT</u>TG | | | 128 |
| *Enterococcus faecalis* | CA<u>ACYGTTAC</u> <u>AGGTGTTGAA</u> <u>ATGTT</u>CC...AA<u>ATGGT</u> <u>AATGCCTGGT</u> <u>GATAACGT</u>TG | | | 132 |
| *Enterococcus faecium* | CA<u>ACAGTTAC</u> <u>TGGTGTTGAA</u> <u>ATGTT</u>CC...AA<u>ATGGT</u> <u>CATGCCCGGT</u> <u>GACAACGT</u>.. | | | 133 |
| *Escherichia coli* | CT<u>ACCTGTAC</u> <u>TGGCGTTGAA</u> <u>ATGTT</u>CC...AG<u>ATGGT</u> <u>AATGCCGGGC</u> <u>GACAACAT</u>CA | | | 154 |
| *Fibrobacter succinogenes* | AC<u>GTCATCAC</u> <u>CGGTGTTGAA</u> <u>ATGTT</u>CC...AA<u>ATGGT</u> <u>TACTCCGGGT</u> <u>GACACGGT</u>CA | | | 155 |
| *Flavobacterium ferrugineum* | CT<u>ACCGTTAC</u> <u>AGGTGTTGAG</u> <u>ATGTT</u>CC...AA<u>ATGGT</u> <u>TATGCCTGGT</u> <u>GATAACA</u>CCA | | | 156 |
| *Gardnerella vaginalis* | CC<u>ACCGTCAC</u> <u>CTCTATCGAG</u> <u>ACCTT</u>CC...AA<u>ATGGT</u> <u>TCAGCCAGGC</u> <u>GATCACG</u>CAA | | | 135 |
| *Haemophilus influenzae* | CT<u>ACTGTAAC</u> <u>GGGTGTTGAA</u> <u>ATGTT</u>CC...AA<u>ATGGT</u> <u>AATGCCAGGC</u> <u>GATAACAT</u>CA | | | 157 |
| *Helicobacter pylori* | CG<u>ACTGTAAC</u> <u>CGGTGTAGAA</u> <u>ATGTT</u>TA...AA<u>ATGGT</u> <u>TATGCCTGGC</u> <u>GATAATGT</u>GA | | | 158 |
| *Listeria monocytogenes* | TAGT<u>AGTAAC</u> <u>TGGAGTAGAA</u> <u>ATGTT</u>CC...AA<u>ATGGT</u> <u>AAYGCCTGGT</u> <u>GATAACAT</u>TG | | | 138 |
| *Micrococcus luteus* | CC<u>ACTGTCAC</u> <u>CGGCATCGAG</u> <u>ATGTT</u>CC...AG<u>ATGGT</u> <u>CATGCCCGGC</u> <u>GACAACA</u>CCG | | | 159 |
| *Mycobacterium tuberculosis* | CC<u>ACCGTCAC</u> <u>CGGTGTGGAG</u> <u>ATGTT</u>CC...AG<u>ATGGT</u> <u>GATGCCCGGT</u> <u>GACAACA</u>CCA | | | 160 |
| *Mycoplasma genitalium* | CA<u>GTTGTTAC</u> <u>TGGAATTGAA</u> <u>ATGTT</u>CA...AA<u>ATGGT</u> <u>TCTACCTGGT</u> GATAATGCTT | | | 161 |
| *Neisseria gonorrhoeae* | CC<u>ACCTGTAC</u> <u>CGGCGTTGAA</u> <u>ATGTT</u>CC...AA<u>ATGGT</u> <u>AATGCCGGGT</u> <u>GAGAACGT</u>AA | | | 162 |
| *Rickettsia prowazekii* | CG<u>ACTTGTAC</u> <u>AGGTGTAGAA</u> <u>ATGTT</u>CA...AG<u>ATGGT</u> <u>TATGCCTGGA</u> <u>GATAATGC</u>TA | | | 163 |
| *Salmonella typhimurium* | CT<u>ACCTGTAC</u> <u>TGGCGTTGAA</u> <u>ATGTT</u>CC...AG<u>ATGGT</u> <u>AATGCCGGGC</u> <u>GACAACAT</u>CA | | | 164 |
| *Shewanella putida* | CA<u>ACGTGTCA</u> <u>TGGTGTAGAA</u> <u>ATGTT</u>CC...AG<u>ATGGT</u> <u>AATGCCAGGC</u> <u>GATAACAT</u>CA | | | 165 |
| *Stigmatella aurantiaca* | CG<u>GTCATCAC</u> <u>GGGGTGGAG</u> <u>ATGTT</u>CC...AG<u>ATGGT</u> <u>GATGCCGGGA</u> <u>GACAACAT</u>CG | | | 166 |
| *Staphylococcus aureus* | CA<u>ACTGTTAC</u> <u>AGGTGTTGAA</u> <u>ATGTT</u>CC...AA<u>ATGGT</u> <u>AATGCCTGGT</u> <u>GATAACGT</u>TG | | | 140 |
| *Staphylococcus epidermidis* | CA<u>ACTGTTAC</u> <u>TGGTGTAGAA</u> <u>ATGTT</u>CC...AA<u>ATGGT</u> <u>TATGCCTGGC</u> <u>GACAACGT</u>TG | | | 141 |
| *Streptococcus agalactiae* | CA<u>GTTGTTAC</u> <u>TGGTGTTGAA</u> <u>ATGTT</u>CC...AA<u>ATGGT</u> <u>TATGCCTGGT</u> <u>GATAACGT</u>TA | | | 144 |
| *Streptococcus pneumoniae* | CA<u>GTTGTTAC</u> <u>TGGTGTTGAA</u> <u>ATGTT</u>CC...AA<u>ATGGT</u> <u>AATGCCTGGT</u> <u>GATAACGT</u>GA | | | 145 |

ANNEX I-continued

Strategy for the selection from tuf sequences of the universal amplification primers.

| | 491 | 517...776 | 802 | SEQ ID NO |
|---|---|---|---|---|
| Streptococcus pyogenes | CTGTTGTTAC TGGTGTTGAA ATGTTCC...AAATGGT TATGCCTGGT GATAACGTGA | | | 167 |
| Thiobacillus cuprinus | CCACCTGCAC CGGCGTGGAA ATGTTCA...AAATGGT CATGCCCGGC GATAATGTGA | | | 168 |
| Treponema pallidum | CAGTGGTTAC TGGCATTGAG ATGTTTA...ACATGGT GAAGCCGGGG GATAACACCA | | | 169 |
| Ureaplasma urealyticum | CTGTTGTTAC AGGAATTGAA ATGTTTA...ATTTGGT TATGCCAGGT GATGACGTTG | | | 170 |
| Wolniella succinogenes | CAACCGTAAC TGGCGTTGAG ATGTTCC...AGATGGT TATGCCTGGT GACAACGTTA | | | 171 |
| Candida albicans | GTGTTACCAC TGAAGTCAAR TCCGTTG...AGRAATT GGAAGAAAAT CCAAAATTCG | | | 120 |
| Schizosaccharomyces pombe | GTGTCACTAC CGAAGTCAAG TCTGTTG...AGAAGAT TGAGGAGTCC CCTAAGTTTG | | | |
| Human | TGACAGGCAT TGAGATGTTC CACAAGA...AGAAGGAGCTTGCCATG CCCGGGGAGG | | | |
| Selected[a] sequences[a] | ACIKKIAC IGGIGTIGAR ATGTT ATGGT IATGCCIGGI GAIAAYRT | | | |
| Selected universal primer sequences[a]: | SEQ ID NO: 23 ACIKKIAC IGGIGTIGAR ATGTT | SEQ ID NO: 24[b] AYRTT ITCICCIGGC ATIACCAT | | |

The sequence numbering refers to the *E. coli* tuf gene fragment. Underlined nucleotides are identical to the selected sequence or match that sequence.
[a] "I" stands for inosine which is a nucleotide analog that can bind to any of the four nucleotides A, C, G or T. "K", "R" and "Y" designate nucleotide positions which are degenerated. "K" stands for T or G; "R" stands for A or G; "Y" stands for C or T.
[b] This sequence is the reverse complement of the above tuf sequence.

ANNEX II

Strategy for the selection from tuf sequences of the amplification primers specific for the genus Enterococcus.

| | 314 | 348 | 401 | 435 | SEQ ID NO |
|---|---|---|---|---|---|
| Bacillus subtilis | CGCGACACTG AAAAACCATT CATGATGCCA GTTGA...CGCGG ACAAGTTAAA GTCGGTGACG AAGTTGAAAT | | | | 148 |
| Bacteroides fragilis | CGCGATGTTG ATAAACCTTT CTTGATGCCG GTAGA...ACTGG TGTTATCCAT GTAGGTGATG AAATCGAAAT | | | | 149 |
| Burkholderia cepacia | CGTGCAGTTG ACGGCGCGTT CCTGATGCCG GTGGA...CGCGG CATCGTGAAG GTCGGCGAAG AAATCGAAAT | | | | 152 |
| Chlamydia trachomatis | AGAGAAATTG ACAAGCCTTT CTTAATGCCT ATTGA...CGTGG AATTGTTAAA GTTTCCGATA AAGTTCAGTT | | | | 153 |
| Corynebacterium diphteriae | CGTGAGACCG ACAAGCCATT CCTCATGCCT ATCGA...CGTGG CTCCCTGAAG GTCAACGAGG ACGTCGAGAT | | | | 126 |
| Enterococcus avium | CGTGATACTG ACAAACCATT CATGATGCCA GTCGA...CGTGG ACAAGTTCGC GTTGGTGACG AAGTTGAAAT | | | | 131 |
| Enterococcus faecalis | CGTGATACTG ACAAACCATT CATGATGCCA GTCGA...CGTGG TGAAGTTCGC GTTGGTGACG AAGTTGAAAT | | | | 132 |
| Enterococcus faecium | CGTGACAACG ACAAACCATT CATGATGCCA GTTGA...CGTGG ACAAGTTCGC GTTGGTGACGAAGTTGAAGT | | | | 133 |
| Enterococcus gallinarum | CGTGATACTG ACAAACCATT CATGATGCCA GTCGA...CGTGG ACAAGTTCGC GTTGGTGATG AAGTAGAAAT | | | | 134 |

ANNEX II-continued

Strategy for the selection from tuf sequences of the amplification primers specific for the genus *Enterococcus*.

| | 314 | | | 348 | 401 | | | 435 | SEQ ID NO |
|---|---|---|---|---|---|---|---|---|---|
| *Escherichia coli* | CGTGCGATTG | ACAAGCCGTT | CCTGCTGCCG | ATCGA | ...CGCGG | TATCATCAAA | GTTGGTGAAG | AAGTTGAAAT | 154 |
| *Gardnerella vaginalis* | CACGATCTTG | ACAAGCCATT | CTTGATGCCA | ATCGA | ...CGTGG | TAAGCTCCCA | ATCAACACCC | CAGTTGAGAT | 135 |
| *Haemophilus influenzae* | CGTGCGATTG | ACCAACCGTT | CCTTCTTCCA | ATCGA | ...CGAGG | TATTATCCGT | ACAGGTGATG | AAGTAGAAAT | 157 |
| *Helicobacter pylori* | AGAGACACTG | AAAAAACTTT | CTTGATGCCG | GTTGA | ...AGAGG | CGTGGTGAAA | GTAGGCGATG | AAGTGGAAAT | 158 |
| *Listeria monocytogenes* | CGTGATACTG | ACAAACCATT | CATGATGCCA | GTTGA | ...CGTGG | ACAAGTTAAA | GTTGGTGACG | AAGTAGAAGT | 138 |
| *Micrococcus luteus* | CGCGACAAGG | ACAAGCCGTT | CCTGATGCCG | ATCGA | ...CGCGG | CACCCTGAAG | ATCAACTCCG | AGGTCGAGAT | 159 |
| *Mycobacterium tuberculosis* | CGCGAGACCG | ACAAGCCGTT | CCTGATGCCG | GTCGA | ...CGCGG | CGTGATb | CAAC GTGAACGAGG | AAGTTGAGAT | 160 |
| *Mycoplasma genitalium* | CGTGAAGTAG | ATAAACCTTT | CTTATTAGCA | ATTGA | ...AGAGG | TGAACTCAAA | GTAGGTCAAG | AAGTTGAAAT | 161 |
| *Neisseria gonorrhoeae* | CGTGCCGTGG | ACAAACCATT | CCTGCTGCCT | ATCGA | ...CGAGG | TATCATCCAC | GTTGGTGACG | AGATTGAAAT | 162 |
| *Salmonella typhimurium* | CGTGCGATTG | ACAAGCCGTT | CCTGCTGCCG | ATCGA | ...CGCGG | TATCATCAAA | GTGGGCGAAG | AAGTTGAAAT | 164 |
| *Shewanella putida* | CGTGACATCG | ATAAGCCGTT | CCTACTGCCA | ATCGA | ...CGTGG | TATTGTACGC | GTAGGCGACG | AAGTTGAAAT | 165 |
| *Staphylococcus aureus* | CGTGATTCTG | ACAAACCATT | CATGATGCCA | GTTGA | ...CGTGG | TCAAATCAAA | GTTGGTGAAG | AAGTTGAAAT | 140 |
| *Staphylococcus epidermidis* | CGTGATTCTG | ACAAACCATT | CATGATGCCA | GTTGA | ...CGTGG | TCAAATCAAA | GTWGGTGAAG | AAGTTGAAAT | 141 |
| *Staphylococcus saprophyticus* | CGTGATTCTG | ACAAACCATT | CATGATGCCA | GTTGA | ...CGTGG | TCAAATCAAA | GTCGGTGAAG | AAATCGARAT | 142 |
| *Streptococcus agalactiae* | CGTGATACTG | ACAAACCTTT | ACTTCTTCCA | GTTGA | ...CGTGG | TACTGTTCGT | GTCAACGACG10 | AAGTTGAAAT | 144 |
| *Streptococcus pneumonia* | CGTGACACTG | ACAAACCATT | GCTTCTTCCA | GTCGA | ...CGTGG | TATCGTTAAA | GTCAACGACG | AAATCGAAAT | 145 |
| *Streptococcus pyogenes* | CGCGACACTG | ACAAACCATT | GCTTCTTCCA | GTCGA | ...CGTGG | TACTGTTCGT | GTCAACGACG | AAATCGAAAT | 167 |
| *Ureaplasma urealyticum* | CGTAGTACTG | ACAAACCATT | CTTATTAGCA | ATTGA | ...CGTGG | TGTATTAAAA | GTTAATGATG | AGGTTGAAAT | 170 |
| Selected sequences | TACTG | ACAAACCATT | CATGATG | | | GTTCGC | GTTGGTGACG | AAGTT | |
| Selected genus-specific primer sequences: | SEQ ID NO: 13 TACTG ACAAACCATT CATGATG | | | | | SEQ ID NO: 14[a] AACTTC GTCACCAACG CGAAC | | | |

The sequence numbering refers to the *E. faecalis* tuf gene fragment. Underlined nucleotides are identical to the selected sequence or match that sequence.

[a]This sequence is the reverse complement of the above tuf sequence.

NOTE:
The above primers also amplify tuf sequences from *Abiotrophia* species; this genus has recently been related to the *Enterococcus* genus by 16S rRNA analysis.

ANNEX III

Strategy for the selection from tuf sequences of the amplification primers specific for the genus *Staphylococcus*.

| | 385 | 420.....579 | 611 | SEQ ID NO |
|---|---|---|---|---|
| *Bacillus subtilis* | TGG<u>CCGTGTA</u> <u>GAACGCGGAC</u> <u>AAGTTAAA</u>GT CGG.....TTG CT<u>AAACCAGG</u> <u>TACAATCACT</u> <u>CCACACA</u>GCA | | | 148 |
| *Bacteroides fragilis* | AGGT<u>CGTATC</u> <u>GAAACTGGTG</u> <u>TTATCCAT</u>GT AGG.....TTT GT<u>AAACCGGG</u> <u>TCAGATTAAA</u> <u>CCTCACT</u>CTA | | | 149 |
| *Burkholderia cepacia* | GGG<u>TCGTGTC</u> <u>GAGCGC</u> | | | 152 |
| *Chlamydia trachomatis* | TGGA<u>CGT</u> <u>ATT</u> <u>GAGCGTGGAA</u> <u>TTGTT</u>AAAGT TTC.....TTT GC<u>TTGCCAAA</u> <u>CAGTGTTAAA</u> <u>CCTCATA</u>CAC | | | 153 |
| *Corynebacterium diphteriae* | CGG<u>CCGTGTT</u> <u>GAGCGTGGCT</u> <u>CCCTGAAG</u>GT CAA.....TTG TT<u>AAGCCAGG</u> <u>CGCTTACACC</u> <u>CCTCACA</u>CCG | | | 126 |
| *Enterococcus faecalis* | AGGA<u>CGTGTT</u> <u>GAACGTGGTG</u> <u>AAGTTCG</u>CGT TGG.....TAG CT<u>AAACCAGC</u> <u>TACAATCACT</u> <u>CCACACA</u>CAA | | | 132 |
| *Enterococcus faecium* | AGGT<u>CGTGTT</u> <u>GAACGTGGAC</u> <u>AAGTTCG</u>CGT TGG.....TAG CT<u>AAACCAGG</u> <u>TACAATCACA</u> <u>CCTCRTA</u>CAA | | | 133 |
| *Escherichia coli* | CGGT<u>CGTGTA</u> <u>GAACGCGGTA</u> <u>TCATCAAA</u>GT TGG.....TGG CT<u>AAGCCGGG</u> <u>CACCATCAAG</u> <u>CCGCACA</u>CCA | | | 154 |
| *Gardnerella vaginalis* | CGGT<u>CGTGTT</u> <u>GAGCGTGGTA</u> <u>AGCTCCCA</u>AT CAA.....TGG CT<u>GCTCCAGG</u> <u>TTCTGTGACT</u> <u>CCACACA</u>CCA | | | 135 |
| *Haemophilus influenzae* | AGGT<u>CGTGTA</u> <u>GAACGAGGTA</u> <u>TTATCCGT</u>AC AGG.....TAG CG<u>AAACCAGG</u> <u>TTCAATCACA</u> <u>CCACACA</u>CTG | | | 157 |
| *Helicobacter pylori* | AGGT<u>AGGATT</u> <u>GAAAGAGGCG</u> <u>TGGTGAAA</u>GT AGG.....TAT GC<u>AAACCAGG</u> <u>TTCTATCACT</u> <u>CCGCACA</u>AGA | | | 158 |
| *Listeria monocytogenes* | TGGA<u>CGTGTT</u> <u>GAACGTGGAC</u> <u>AAGTTAAA</u>GT TGG.....TAG CT<u>AAACCAGG</u> <u>TTCGATTACT</u> <u>CCACACA</u>CTA | | | 138 |
| *Micrococcus luteus* | CGGT<u>CGCGCC</u> <u>GAGCGCGGCA</u> <u>CCCTGAAG</u>AT CAA.....TGG TG<u>GAGCCGGG</u> <u>CTCCATCACC</u> <u>CCGCACA</u>CCA | | | 159 |
| *Mycobacterium tuberculosis* | CGGA<u>CGTGTG</u> <u>GAGCGCGGCG</u> <u>TGATCAAC</u>GT GAA.....TCA CC<u>AAGCCCGG</u> <u>CACCACCACG</u> <u>CCGCACA</u>CCG | | | 160 |
| *Mycoplasma genitalium* | AGGA<u>AGAGTT</u> <u>GAAAGAGGTG</u> <u>AACTCAAA</u>GT AGG.....TAG CA<u>AAACCAGG</u> <u>CTCTATTAAA</u> <u>CCGCACA</u>AGA | | | 161 |
| *Neisseria gonorrhoeae* | CGG<u>CCGTGTA</u> <u>GAGCGAGGTA</u> <u>TCATCCAC</u>GT TGG.....TGG CC<u>AAACGGGG</u> <u>TACTATCACT</u> <u>CCTCACA</u>CCA | | | 162 |
| *Salmonella typhimurium* | CGGT<u>CGTGTA</u> <u>GAGCGCGGTA</u> <u>TCATCAAA</u>GT GGG.....TGG CT<u>AAGCCGGG</u> <u>CACCATCAAG</u> <u>CCGCACA</u>CCA | | | 164 |
| *Shewanella putida* | AGGT<u>CGTGTT</u> <u>GAGCGTGGTA</u> <u>TTGTACGC</u>GT AGG.....TAG CG<u>AAGCCAGG</u> <u>TTCAATCAAC</u> <u>CCACACA</u>CTA | | | 165 |
| <u>*Staphylococcus aureus*</u> | AGG<u>CCGTGTT</u> <u>GAACGTGGTC</u> <u>AAATCAAA</u>GT TGG.....TAG CT<u>GCTCCTGG</u> <u>TTCAATTACA</u> <u>CCACATA</u>CTG | | | 140 |
| <u>*Staphylococcus epidermidis*</u> | AGG<u>CCGTGTT</u> <u>GAACGTGGTC</u> <u>AAATCAAA</u>GT WGG.....TAG CT<u>GCTCCTGG</u> <u>TTCTATTACA</u> <u>CCACACA</u>CAA | | | 141 |
| <u>*Staphylococcus saprophyticus*</u> | AGG<u>CCGTGTT</u> <u>GAACGTGGTC</u> <u>AAATCAAA</u>GT CGG.....TAG CT<u>GCTCCTGG</u> <u>TACTATCACA</u> <u>CCACATA</u>CAA | | | 142 |
| <u>*Staphylococcus simulans*</u> | AGG<u>CCGTGTT</u> <u>GAACGTGGTC</u> <u>AAATCAAA</u>GT CGG.....TAG CA<u>GCTCCTGG</u> <u>CTCTATTACT</u> <u>CCACACA</u>CAA | | | 143 |
| *Streptococcus agalactiae* | AGGA<u>CGTATC</u> <u>GACCGTGGTA</u> <u>CTGTTCGT</u>GT CAA.....TTG CT<u>AAACCAGG</u> <u>TTCAATCAAC</u> <u>CCACACA</u>CTA | | | 144 |
| *Streptococcus pneumoniae* | AGGA<u>CGTATC</u> <u>GACCGTGGTA</u> <u>TCGTTAAA</u>GT CAA.....TCG CT<u>AAACCAGG</u> <u>TTCAATCAAC</u> <u>CCACACA</u>CTA | | | 145 |
| *Ureaplasma urealyticum* | TGGA<u>CGTGTT</u> <u>GAACGTGGTG</u> <u>TATTAAAA</u>GT TAA.....TTG TA<u>AAACCAGG</u> <u>ATCAATTAAA</u> <u>CCTCACC</u>GTA | | | 170 |

ANNEX III-continued

**Strategy for the selection from tuf sequences of the amplification primers specific for the genus *Staphylococcus*.**

| | 385 | 420.....579 | 611 | SEQ ID NO |
|---|---|---|---|---|

| | | | |
|---|---|---|---|
| Selected sequences | CCGTGTT GAACGTGGTC AAATCAAA | | GCTCCTGG YWCWATYACA CCACAYA |
| Selected genus-specific primer sequences*: | SEQ ID NO: 17<br>CCGTGTT GAACGTGGTC AAATCAAA | | SEQ ID NO: 18[b]<br>TRTGTGG GTRATWGWRC CAGGAGC |

The sequence numbering refers to the *S. aureus* tuf gene fragment. Underlined nucleotides are identical to the selected sequence or match that sequence.
[a]"R", "W" and "Y" designate nucleotide positions which are degenerated. "R" stands for A or G; "W", for A or T; "Y", for C or T.
[b]This sequence is the reverse complement of the above tuf sequence.

ANNEX IV

**Strategy for the selection from tuf sequences of the amplification primers specific for the species *Candida albicans*.**

| | 58 | 90 | 181 | 213 | SEQ ID NO |
|---|---|---|---|---|---|
| *Candida albicans* | CGTCAAGAAG GTTGGTTACA ACCCAAAGAC | TGT...CAA | ATCCGGTAAA GTTACTGGTA AGACCTTGTT | | 120 |
| *Candida glabrata* | CATCAAGAAG GTCGGTTACA ACCCAAAGAC | TGT...CAA | GGCTGGTGTC GTCAAGGGTA AGAYCTTGTT | | 121 |
| *Candida krusei* | CATCAAGAAG GTTGGTTACA ACCCAAAGAC | TGT...CAA | GGCAGGTGTT GTTAAGGGTA AGACCTTATT | | 122 |
| *Candida parapsilosis* | CGTCAAGAAG GTTGGTTACA ACCCTAAAGC | TGT...TAA | AGCTGGTAAG GTTACCGGTA AGACCTTGTT | | 123 |
| *Candida tropicalis* | CGTCAAGAAG GTTGGTTACA ACCCTAAGGC | TGT...CAA | GGCTGGTAAG GTTACCGGTA AGACTTTGTT | | 124 |
| *Schizosaccharomyces pombe* | CATCAAGAAG GTCGGTTTCA ACCCCAAGAC | CGT...CAA | GGCTGGTGTC GTCAAGGGTA AGACTCTTTT | | |
| Human | GGAGATCCGG GAGCTGCTCA CCGAGTTTGG | CTA...GTT | AGGCCTGAAG TCTGTGCAGA AGCTACTGGA | | |
| *Chlamydia trachomatis* | GGAGCTGCGC GAGCTGCTCA GCAAGTACGG | CTT...CAA | ATG........ ..TATTCTGG AGCTGATGAA | | 153 |
| *Corynebacterium diphteriae* | GGAGATCCRT GAGCTGCTCG CTGAGCAGGA | TTA...GAA | GTGGACCCAG TCCATCATCG ACCTCATGCA | | 126 |
| *Enterococcus faecalis* | GGAAGTTCGT GACTTATTAT CAGAATACGA | TTT...... ...TGAAGAA | AAAATCTTAG AATTAATGGC | | 132 |
| *Escherichia coli* | GGAAGTTCGT GAACTTCTGT CTCAGTACGA | CTT...... ..GGGAAGCG | AAAATCCTGG AACTGGCTGG | | 154 |
| *Flavobacterium ferrugineum* | CGAGGTTCGC GAAGAACTGA CTAAACGCGG | TTT...... ..GGGTTAAA GAAATTGAAA ACCTGATGGA | | 156 |
| *Gardnerella vaginalis* | AGAGGTCCGT GACCTCCTCG AAGAAAACGG | CTT...CAA | GTGGGTAGAG ACCGTCAAGG AACTCATGAA | | 135 |
| *Haemophilus influenzae* | GGAAGTTCGT GAACTTCTAT CTCAATATGA | CTT...... ..GGGAAGAA AAAATCCTTG AGTTAGCAAA | | 157 |
| *Listeria monocytogenes* | GGAAATTCGT GATCTATTAA CTGAATATGA | ATT...... ..GGGAAGCT AAAATTGACG AGTTAATGGA | | 138 |
| *Micrococcus luteus* | GGAAGTCCGT GAGTTGCTGG CTGCCCAGGA | ATT...CAA | GTGGGTCGAG TCTGTCACAC AGTTGATGGA | | 159 |
| *Neisseria gonorrhoeae* | GGAAATCCGC GACCTGCTGT CCAGCTACGA | CTT...... ..ACGAAGAA AAAATCTTCG AACTGGCTAC | | 162 |

ANNEX IV-continued

**Strategy for the selection from tuf sequences of the amplification primers specific for the species *Candida albicans*.**

| | 58 | 90 | 181 | 213 | SEQ ID NO |
|---|---|---|---|---|---|
| *Salmonella typhimurium* | GGAAGTTCGC GAACTGCTGT CTCAGTACGA CTT...... | | ..GGGAACGC AAAATCATCG AACTGGCTGG | | 164 |
| *Staphylococcus aureus* | GGAAGTTCGT GACTTATTAA GCGAATATGA CTT...... | | ...CGAAGAA AAAATCTTAG AATTAATGGA | | 140 |
| *Streptococcus pneumoniae* | GGAAATCCGT GACCTATTGT CAGAATACGA CTT...... | | ...CGAAGAC ATCGTTATGG AATTGATGAA | | 145 |
| *Treponema pallidum* | AGAGGTGCGT GATGCGCTTG CTGGATATGG GTT...GGA | | GGATGCAGCT TGTATTGAGG AACTGCTTGC | | 169 |
| Selected sequences | CAAGAAG GTTGGTTACA ACCCAAGA | | ATCCGGTAAA GTTACTGGTA AGACCT | | |
| Selected species-specific primer sequences: | SEQ ID NO: 11 CAAGAAG GTTGGTTACA ACCCAAAGA | | SEQ ID NO: 12ᵃ AGGTCTTACC AGTAACTTTAC CGGAT | | |

The sequence numbering refers to the *Candida albicans* tuf gene fragment. Underlined nucleotides are identical to the selected sequence or match that sequence.
ᵃThis sequence is the reverse-complement of the above tuf sequence.

ANNEX V

**Strategy for the selection from the recA gene of the amplification primers specific for the genus *Streptococcus*.**

| | 415 | 449...540 | 574 | SEQ ID NO |
|---|---|---|---|---|
| *Bordetella pertussis* | CTCGAGATCA CCGACGCGCT GGTGCGCTCG | GGCTC...GGCCC | GCCTGATGAG CCAGGCGCTG CGCAAGCTGA | |
| *Burkholderia cepacia* | CTCGAAATCA CCGATGCGCT GGTGCGCTCG | GGCTC...GGCCC | GCCTGATGTC GCAGGCGCTG CGCAAGCTGA | |
| *Campylobacter jejuni* | TTAGAAATTG TAGAAACTAT AGCAAGAAGT | GGCGC...AGCAA | GACTTATGTC TCAAGCTCTA AGAAAACTTA | |
| *Chlamydia trachomatis* | TTGAGTATTG CAGAGCTCTT AGCGCGTTCT | GGACG...AGCTC | GCATGATGTC GCAGGCTCTA CGCAAATTAA | |
| *Clostridium perfringens* | TTAGAAATAA CAGAAGCTTT AGTTAGATCA | GGAGC...AGCTA | GATTAATGTC ACAAGCCTTA AGAAAGTTAA | |
| *Corynebacterium pseudotuberculosis* | CTGGAGATTG CAGATATGCT TGTTCGCTCT | GGAGC...AGCGC | GTTTGATGAG TCAGGCGCTG CGTAAGCTTG | |
| *Enterobacter agglomerans* | CTGGAAATCT GTGATGCGCT GACCCGTTCA | GGCGC...AGCTC | GTATGATGAG CCAGGCGATG CGTAAGCTTG | |
| *Enterococcus faecium* | TTAGAGATTG CCGATGCCTT AGTTTCAAGT | GGTGC...AGCTC | GACTAATGTC TCAAGCACTA CGTAAATTAT | |
| *Escherichia coli* | CTGGAAATCT GTGACGCCCT GGCGCGTTCT | GGCGC...GGCAC | GTATGATGAG CCAGGCGATG CGTAAGCTGG | |
| *Haemophilus influenzae* | GCGAACAGAA GAATAGAATT TTAATGCATT | ACCGC...GACCT | GTGAGTTTAC GCAAAGCTTG AGACATTAAA | |
| *Helicobacter pylori* | TTAGAAATTT TAGAAACGAT CACCAGAAGC | GGAGG...AGCAA | GGCTTATGAG CCATGCGTTA AGAAAAATCA | |
| *Lactococcus lactis* | CTTCAAATTG CTGAAAAATT GATTACTTCT | GGAGC...AGCAC | GTATGATGTC ACAAGCCATG CGTAAACTTG | |
| *Legionella pneumophila* | CTGGAAATTA CTGATATGCT GGTGCGTTCT | GCAGC...GGCAA | GATTGATGTC GCAAGCCCTG CGTAAATTGA | |

ANNEX V-continued

Strategy for the selection from the recA gene of the amplification primers specific for the genus *Streptococcus*.

| | 415 | 449...540 | 574 | SEQ ID NO |
|---|---|---|---|---|
| *Mycoplasma genitalium* | TTTGCTCTTA TCGAATCATT AATTAAAACA AACAA...TGCAA GAATGATGTC AAAAGGTTTG CGAAGAATAC | | | |
| *Neisseria gonorrhoeae* | TTGGAAATCT GCGACACGCT CGTCCGTTCG GGCGG...GGCGC GCCTGATGAG TCAGGCTTTG CGCAAACTGA | | | |
| *Proteus mirabilis* | CTGGAAATTT GTGATGCATT ATCTCGCTCT GGTGC...CGCAC GTATGATGAG CCAAGCTATG CGTAAACTAG | | | |
| *Pseudomonas aeruginosa* | CTGGAAATCA CCGACATGCT GGTGCGCTCC AACGC...GGCAC GCCTGATGTC CCAGGCGCTG CGCAAGATCA | | | |
| *Serratia marcescens* | CTGGAAATCT GTGATGCGCT GACCCGCTCC GGCGC...GGCGC GCATGATGAG CCAGGCGATG CGTAAGCTGG | | | |
| *Shigella flexneri* | CTGGAAATCT GTGACGCCCT GGCGCGTTCT GGCGC...GGCAC GTATGATGAG CCAGGCGATG CGTAAGCTGG | | | |
| *Staphylococcus aureus* | CTTGAAATCG CCGAAGCATT TGTTAGAAGT GGTGC...AGCTC GTTAATGTC ACAAGCGTTA CGTAAACTTT | | | |
| *Streptococcus gordonii* | TTAGAAATTG CAGGAAAATT GATTGACTCT GGGGC........ .......... .......... .......... | | | 32 |
| *Streptococcus mutans* | CTTGAAATTG CAGGGAAATT GATTGATTCT GGCGC...AGCAC GCATGATGAG TCAAGCGATG CGTAAATTAT | | | 33 |
| *Streptococcus pneumoniae* | CTTGAGATTG CGGGAAAATT GATTGACTCA GGTGC...GGCTC GTATGATGAG CCAGGCCATG CGTAAACTTG | | | 34 |
| *Streptococcus pyogenes* | CTTGAAATTG CAGGTAAATT GATTGATTCT GGTGC...AGCAC GTATGATGAG TCAGGCCATG CGTAAATTAT | | | 35 |
| *Streptococcus salivarius* | CTCAAATTG CAGGTAAGCT GATTGACTCT GGTGC...AGCGC GTATGATGAG TCAAGCCATG CGTAAACTTT | | | 36 |
| *Vibrio cholerae* | CTGGAAATTT GTGATGCACT GGCTCGCTCT GGTGC...AGCGC GTATGTTGTC GCAAGCAATG CGTAAACTGA | | | |
| *Yersinia pestis* | CTGGAAATTT GTGATGCGCT GACTCGCTCT GGTGC...CGCGC GTATGATGAG CCAGGCTATG CGTAAGCTGG | | | |
| Selected sequences[a] | GAAATGG CAGGIAAATT GATTGA | | ATGATGAG TCAIGCCATG CGTAA | |
| Selected genus-specific primer sequences[a]: | SEQ ID NO: 21<br>GAAATTG CAGGIAAATT GATTGA | | SEQ ID NO: 22[b]<br>TTACGCAT GGCITGACTC ATCAT | |

The sequence numbering refers to the *S. pneumoniae* recA sequence. Underlined nucleotides are identical to the selected sequence or match that sequence.
[a]"I" stands for inosine which is a nucleotide analog that can bind to any of the four nucleotides A, C, G or T.
[b]This sequence is the reverse complement of the above recA sequence.

Annex VI

Specific and ubiquitous primers for DNA amplification

| | | Originating DNA fragment | |
|---|---|---|---|
| SEQ ID NO | Nucleotide sequence | SEQ ID NO | Nucleotide position |
| Bacterial species: *Enterococcus faecium* | | | |
| 1 | 5'-TGC TTT AGC AAC AGC CTA TCA G | 26[a] | 273-294 |
| 2[b] | 5'-TAA ACT TCT TCC GGC ACT TCG | 26[a] | 468-488 |
| Bacterial species: *Listeria monocytogenes* | | | |
| 3 | 5'-TGC GGC TAT AAA TGA AGA GGC | 27[a] | 339-359 |

Annex VI-continued

Specific and ubiquitous primers for DNA amplification

| | | | |
|---|---|---|---|
| 4[b] | 5'-ATC CGA TGA TGC TAT GGC TTT | 27[a] | 448-468 |

Bacterial species: *Neisseria meningitidis*

| | | | |
|---|---|---|---|
| 5 | 5'-CCA GCG GTA TTG TTT GGT GGT | 28[a] | 56-76 |
| 6[b] | 5'-CAG GCG GCC TTT AAT AAT TTC | 28[a] | 212-232 |

Bacterial species: *Staphylococcus saprophyticus*

| | | | |
|---|---|---|---|
| 7 | 5'-AGA TCG AAT TCC ACA TGA AGG TTA TTA TGA | 29[c] | 290-319 |
| 8[b] | 5'-TCG CTT CTC CCT CAA CAA TCA AAC TAT CCT | 29[c] | 409-438 |

Bacterial species: *Streptococcus agalactiae*

| | | | |
|---|---|---|---|
| 9 | 5'-TTT CAC CAG CTG TAT TAG AAG TA | 30[a] | 59-81 |
| 10[b] | 5'-GTT CCC TGA ACA TTA TCT TTG AT | 30[a] | 190-212 |

Fungal species: *Candida albicans*

| | | | |
|---|---|---|---|
| 11 | 5'-CAA GAA GGT TGG TTA CAA CCC AAA GA | 120[c] | 61-86 |
| 12[b] | 5'-AGG TCT TAC CAG TAA CTT TAC CGG AT | 120[c] | 184-209 |

[a] Sequences from databases.
[b] These sequences are from the opposite DNA strand of the sequence of the originating fragment given in the Sequence Listing.
[c] Sequences determined by our group.

| | | Originating DNA fragment | |
|---|---|---|---|
| SEQ ID NO | Nucleotide sequence | SEQ ID NO | Nucleotide position |

Bacterial genus: Enterococcus

| | | | |
|---|---|---|---|
| 13 | 5'-TAC TGA CAA ACC ATT CAT GAT G | 131-134[a,b] | 319-340[c] |
| 14[d] | 5'-AAC TTC GTC ACC AAC GCG AAC | 131-134[a,b] | 410-430[c] |

Bacterial genus: Neisseria

| | | | |
|---|---|---|---|
| 15 | 5'-CTG GCG CGG TAT GGT CGG TT | 31[e] | 21-40[f] |
| 16[d] | 5'-GCC GAC GTT GGA AGT GGT AAA G | 31[e] | 102-123[f] |

Bacterial genus: Staphylococcus

| | | | |
|---|---|---|---|
| 17 | 5'-CCG TGT TGA ACG TGG TCA AAT CAA A | 140-143[a,b] | 391-415[g] |
| 18[d] | 5'-TRT GTG GTG TRA TWG WRC CAG GAG C | 140-143[a,b] | 584-608[g] |
| 19 | 5'-ACA ACG TGG WCA AGT WTT AGC WGC T | 140-143[a,b] | 562-583[g] |
| 20[d] | 5'-ACC ATT TCW GTA CCT TCT GGT AAG T | 140-143[a,b] | 729-753[g] |

Bacterial genus: Streptococcus

| | | | |
|---|---|---|---|
| 21 | 5'-GAA ATT GCA GGI AAA TTG ATT GA | 32-36[e] | 418-440[h] |
| 22[d] | 5'-TTA CGC ATG GCI TGA CTC ATC AT | 32-36[e] | 547-569[h] |

Universal primers

| | | | |
|---|---|---|---|
| 23 | 5'-ACI KKI ACI GGI GTI GAR ARG TT | 118-146[a,b] | 493-515[i] |
| | | 147-171[a,e] | |
| 24[d] | 5'-AYR TTI TCI CCI GGC ATI ACC AT | 118-146[a,b] | 778-800[i] |
| | | 147-171[a,e] | |

[a] These sequences were aligned to derive the corresponding primer.
[b] tuf sequences determined by our group.
[c] The nucleotide positions refer to the *E. faecalis* tuf gene fragment (SEQ ID NO: 132).
[d] These sequences are from the opposite DNA strand of the sequence of the originating fragment given in the Sequence Listing.
[e] Sequences from databases.
[f] The nucleotide positions refer to the *N. meningitidis* asd gene fragment (SEQ ID NO: 31).
[g] The nucleotide positions refer to the *S. aureus* tuf gene fragment (SEQ ID NO: 140).
[h] The nucleotide positions refer to the *S. pneumoniae* recA gene (SEQ Annex VI-continued Specific and ubiquitous primers for DNA amplification ID NO: 34).
$^i$The nucleotide positions refer to the *E. coli* tuf gene fragment (SEQ ID NO: 154).

| SEQ ID NO | Nucleotide sequence | Originating DNA fragment SEQ ID NO | Nucleotide position |
|---|---|---|---|
| Antibiotic resistance gene: bla$_{tem}$ | | | |
| 37 | 5'-CTA TGT GGC GCG GTA TTA TC | — | — |
| 38 | 5'-CGC AGT GTT ATC ACT CAT GG | — | — |
| 39 | 5'-CTG AAT GAA GCC ATA CCA AA | — | — |
| 40 | 5'-ATC AGC AAT AAA CCA GCC AG | — | — |
| Antibiotic resistance gene: bla$_{shv}$ | | | |
| 41 | 5'-TTA CCA TGA GCG ATA ACA GC | — | — |
| 42 | 5'-CTC ATT CAG TTC CGT TTC CC | — | — |
| 43 | 5'-CAG CTG CTG CAG TGG ATG GT | — | — |
| 44 | 5'-CGC TCT GCT TTG TTA TTC GG | — | — |
| Antibiotic resistance gene: bla$_{rob}$ | | | |
| 45 | 5'-TAC GCC AAC ATC GTG GAA AG | — | — |
| 46 | 5'-TTG AAT TTG GCT TCT TCG GT | — | — |
| 47 | 5'-GGG ATA CAG AAA CGG GAC AT | — | — |
| 48 | 5'-TAA ATC TTT TTC AGG CAG CG | — | — |
| Antibiotic resistance gene: bla$_{oxa}$ | | | |
| 49 | 5'-GAT GGT TTG AAG GGT TTA TTA TAA G | 110$^a$ | 686-710 |
| 50$^b$ | 5'-AAT TTA GTG TGT TTA GAA TGG TGA T | 110$^a$ | 802-826 |
| Antibiotic resistance gene: blaZ | | | |
| 51 | 5'-ACT TCA ACA CCT GCT GCT TTC | 111$^a$ | 511-531 |
| 52$^b$ | 5'-TGA CCA CTT TTA TCA GCA ACC | 111$^a$ | 663-683 |
| Antibiotic resistance gene: aadB | | | |
| 53 | 5'-GGC AAT AGT TGA AAT GCT CG | — | — |
| 54 | 5'-CAG CTG TTA CAA CGG ACT GG | — | — |
| Antibiotic resistance gene: aacC1 | | | |
| 55 | 5'-TCT ATG ATC TCG CAG TCT CC | — | — |
| 56 | 5'-ATC GTC ACC GTA ATC TGC TT | — | — |

$^a$Sequences from databases.
$^b$These sequences are from the opposite DNA strand of the sequence of the originating fragment given in the Sequence Listing.

| SEQ ID NO | Nucleotide sequence | Originating DNA fragment SEQ ID NO | Nucleotide position |
|---|---|---|---|
| Antibiotic resistance gene: aacC2 | | | |
| 57 | 5'-CAT TCT CGA TTG CTT TGC TA | — | — |
| 58 | 5'-CCG AAA TGC TTC TCA AGA TA | — | — |
| Antibiotic resistance gene: aacC3 | | | |
| 59 | 5'-CTG GAT TAT GGC TAC GGA GT | — | — |
| 60 | 5'-AGC AGT GTG ATG GTA TCC AG | — | — |

Annex VI-continued

Specific and ubiquitous primers for DNA amplification

| SEQ ID NO | Nucleotide sequence | Originating DNA fragment SEQ ID NO | Nucleotide position |
|---|---|---|---|
| Antibiotic resistance gene: aac6'-IIa | | | |
| 61 | 5'-GAC TCT TGA TGA AGT GCT GG | 112[a] | 123-142 |
| 62[b] | 5'-CTG GTC TAT TCC TCG CAC TC | 112[a] | 284-303 |
| 63 | 5'-TAT GAG AAG GCA GGA TTC GT | 112[a] | 445-464 |
| 64[b] | 5'-GCT TTC TCT CGA AGG CTT GT | 112[a] | 522-541 |
| Antibiotic resistance gene: aacA4 | | | |
| 65 | 5'-GAG TTG CTG TTC AAT GAT CC | — | — |
| 66 | 5'-GTG TTT GAA CCA TGT ACA CG | — | — |
| Antibiotic resistance gene: aad(6') | | | |
| 173 | 5'-TCT TTA GCA GAA CAG GAT GAA | — | — |
| 174 | 5'-GAA TAA TTC ATA TCC TCC G | — | — |
| Antibiotic resistance gene: vanA | | | |
| 67 | 5'-TGT AGA GGT CTA GCC CGT GT | — | — |
| 68 | 5'-ACG GGG ATA ACG ACT GTA TG | — | — |
| 69 | 5'-ATA AAG ATG ATA GGC CGG TG | — | — |
| 70 | 5'-TGC TGT CAT ATT GTC TTG CC | — | — |
| Antibiotic resistance gene: vanB | | | |
| 71 | 5'-ATT ATC TTC GGC GGT TGC TC | 116[a] | 22-41 |
| 72[b] | 5'-GAC TAT CGG CTT CCC ATT CC | 116[a] | 171-190 |
| 73 | 5'-CGA TAG AAG CAG CAG GAC AA | 116[a] | 575-594 |
| 74[b] | 5'-CTG ATG GAT GCG GAA GAT AC | 116[a] | 713-732 |

[a]Sequences from databases.
[b]These sequences are from the opposite DNA strand of the sequence of the originating fragment given in the Sequence Listing.

| SEQ ID NO | Nucleotide sequence | Originating DNA fragment SEQ ID NO | Nucleotide position |
|---|---|---|---|
| Antibiotic resistance gene: vanC | | | |
| 75 | 5'-GCC TTA TGT ATG AAC AAA TGG | 117[a] | 373-393 |
| 76[b] | 5'-GTG ACT TTW GTG ATC CCT TTT GA | 117[a] | 541-563 |
| Antibiotic resistance gene: msrA | | | |
| 77 | 5'-TCC AAT CAT TGC ACA AAA TC | — | — |
| 78 | 5'-AAT TCC CTC TAT TTG GTG GT | — | — |
| 79 | 5'-TCC CAA GCC AGT AAA GCT AA | — | — |
| 80 | 5'-TGG TTT TTC AAC TTC TTC CA | — | — |
| Antibiotic resistance gene: satA | | | |
| 81 | 5'-TCA TAG AAT GGA TGG CTC AA | — | — |
| 82 | 5'-AGC TAC TAT TGC ACC ATC CC | — | — |
| Antibiotic resistance gene: aac(6')-aph(2") | | | |
| 83 | 5'-CAA TAA GGG CAT ACC AAA AAT C | — | — |
| 84 | 5'-CCT TAA CAT TTG TGG CAT TAT C | — | — |
| 85 | 5'-TTG GGA AGA TGA AGT TTT TAG A | — | — |
| 86 | 5'-CCT TTA CTC CAA TAA TTT GGC T | — | — |

Annex VI-continued

Specific and ubiquitous primers for DNA amplification

Antibiotic resistance gene: vat
87   5'-TTT CAT CTA TTC AGG ATG GG            —        —

88   5'-GGA GCA ACA TTC TTT GTG AC           —        —

Antibiotic resistance gene: vga
89   5'-TGT GCC TGA AGA AGG TAT TG           —        —

90   5'-CGT GTT ACT TCA CCA CCA CT           —        —

Antibiotic resistance gene: ermA
91   5'-TAT CTT ATC GTT GAG AAG GGA TT       113[a]   370-392

92[b] 5'-CTA CAC TTG GCT TAG GAT GAA A       113[a]   487-508

[a]Sequences from databases.
[b]These sequences are from the opposite DNA strand of the sequence of the originating fragment given in the Sequence Listing.

|  |  | Originating DNA fragment | |
|---|---|---|---|
| SEQ ID NO | Nucleotide sequence | SEQ ID NO | Nucleotide position |

Antibiotic resistance gene: ermB
93   5'-CTA TCT GAT TGT TGA AGA AGG ATT      114[a]   366-389

94[b] 5'-GTT TAC TCT TGG TTT AGG ATG AAA     114[a]   484-507

Antibiotic resistance gene: ermC
95   5'-CTT GTT GAT CAC GAT AAT TTC C        115[a]   214-235

96[b] 5'-ATC TTT TAG CAA ACC CGT ATT C       115[a]   382-403

Antibiotic resistance gene: mecA
97   5'-AAC AGG TGA ATT ATT AGC ACT TGT AAG  —        —

98   5'-ATT GCT GTT AAT ATT TTT TGA GTT GAA  —        —

Antibiotic resistance gene: int
99   5'-GTG ATC GAA ATC CAG ATC C            —        —
100  5'-ATC CTC GGT TTT CTG GAA G            —        —

101  5'-CTG GTC ATA CAT GTG ATG G            —        —

102  5'-GAT GTT ACC CGA GAG CTT G            —        —

Antibiotic resistance gene: sul
103  5'-TTA AGC GTG CAT AAT AAG CC           —        —

104  5'-TTG CGA TTA CTT CGC CAA CT           —        —

105  5'-TTT ACT AAG CTT GCC CCT TC           —        —

106  5'-AAA AGG CAG CAA TTA TGA GC           —        —

[a]Sequences from databases.
[b]These sequences are from the opposite DNA strand of the sequence of the originating fragment given in the Sequence Listing.

---

What is claimed is:

1. A method for detecting whether bacterial species *Streptococcus agalactiae* is present in a test sample containing nucleic acids which comprises the following steps:
   a) contacting said sample with an amplification primer pair, said amplification primer pair consisting of a first primer and a second primer, wherein each of said first primer and said second primer of the pair is at least 18 nucleotides in length, wherein the first primer of the amplification primer pair hybridizes under conditions of 50 mM KCl, 10 mM Tris-HCl (pH 9.0), 2.5 mM $MgCl_2$, at 55° C. to nucleic acids containing at least 18 consecutive nucleotides of SEQ ID NO:9 or the full complement thereof, and wherein the second primer of the amplification primer pair hybridizes under conditions of 50 mM KCl, 10 mM Tris-HCl (pH 9.0), 2.5 mM $MgCl_2$, at 55° C. to nucleic acids containing at least 18 consecutive nucleotides of or SEQ ID NO:10 or the full complements thereof;
   b) performing an amplification reaction in the presence of said sample and said amplification primer pair at a condition such that the nucleic acid sequence between SEQ ID NO:9 and SEQ ID NO:10 in the genome of strains of *Streptococcus agalactiae* (*S. agalactiae*) is specifically and ubiquitously amplified and an amplicon comprising the nucleic acid sequence between SEQ ID NO:9 and SEQ ID NO:10 in the genome of strains of *S. agalactiae* is generated; and
   c) testing for the presence and/or amount of said amplicon, wherein the presence of said amplicon is indicative of the presence *S. agalactiae* in said test sample, and wherein the absence of said amplicon is indicative of the absence of *S. agalacitae* in said test sample.

2. The method of claim 1, wherein the step c) comprises detecting said amplicon with a probe complementary to said amplicon.

3. The method of claim 1, further comprising a step of detecting other microbial species in said test sample.

4. The method of claim 1, further comprising a step of detecting one or more antibiotic resistance genes associated with bacterial resistance in said test sample.

5. The method of claim 1, wherein said amplification reaction is a method selected from the group consisting of:
   a) polymerase chain reaction (PCR);
   b) ligase chain reaction (LCR);
   c) nucleic acid sequence-based amplification (NASBA);
   d) self-sustained sequence replication (3SR);
   e) strand displacement amplification (SDA);
   f) branched DNA signal amplification (bDNA);
   g) transcription-mediated amplification (TMA);
   h) cycling probe technology (CPT); and
   i) nested PCR.

6. The method of claim 5, wherein said amplification reaction is PCR.

7. A diagnostic kit for detecting and/or quantifying nucleic acids from cells of *Streptococcus agalactiae*, comprising an amplification primer pair, said amplification primer pair consisting of a first primer and a second primer, wherein of said first primer and second primer is at least 18 nucleotides in length, wherein the first primer of the amplification primer pair hybridizes under conditions of 50 mM KCl, 10 mM Tris-HCl (pH 9.0), 2.5 mM $MgCl_2$, at 55° C. to nucleic acids containing at least 18 consecutive nucleotides of SEQ ID NO:9 or the full complement thereof, wherein the second primer of the amplification primer pair hybridizes under conditions of 50 mM KCl, 10 mM Tris-HCl (pH 9.0), 2.5 mM $MgCl_2$ at 55° C. to nucleic acids containing at least 18 consecutive nucleotides of SEQ ID NO:10 or the full complements thereof, and wherein said amplification primer pair specifically and ubiquitously amplifies the nucleic acid sequence between SEQ ID NO:9 and SEQ ID NO: 10 in the genome of strains of *Streptococcus agalactiae*.

8. The diagnostic kit of claim 7, wherein said first primer comprises the nucleic acid of SEQ ID NO: 9.

9. The diagnostic kit of claim 8, wherein said second primer comprises the nucleic acid of SEQ ID NO: 10.

10. The diagnostic kit of claim 7, wherein said first primer consists of SEQ ID NO: 9.

11. The diagnostic kit of claim 7, wherein said second primer consists of SEQ ID NO: 10.

12. The diagnostic kit of claim 7, for further detecting and/or quantifying one more or bacterial antibiotic resistance genes, further comprising at least one probe and/or primer having at least 18 nucleotides in length, wherein said probe and/or primer hybridizes with a bacterial antibiotic resistance gene selected from the group consisting of $bla_{tem}$, $bla_{shv}$, $bla_{rob}$, $bla_{oxa}$, blaZ, aadB, aacC1, aacC2, aacC3, aac6'-IIa, aacA4, aad(6'), vanA, vanB, vanC, msrA, satA, aac(6')-aph (2'), vat, vga, ermA, ermB, ermC, mecA, int and sul.

13. The diagnostic kit of claim 12, wherein said first primer comprises the nucleic acid of SEQ ID NO: 9.

14. The diagnostic kit of claim 13, wherein said second primer comprises the nucleic acid of SEQ ID NO: 10.

15. The diagnostic kit of claim 12, wherein the kit further comprises a nucleic acid selected from the group consisting of SEQ ID NOs: 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 173, 174, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101,102, 103,104, 105, and 106.

16. The diagnostic kit of claim 12, wherein said first primer consists of SEQ ID NO: 9.

17. The diagnostic kit of claim 12, wherein said second primer consists of SEQ ID NO: 10.

* * * * *